(12) United States Patent
Vidlund et al.

(10) Patent No.: US 11,464,628 B2
(45) Date of Patent: Oct. 11, 2022

(54) EXPANDABLE EPICARDIAL PADS AND DEVICES AND METHODS FOR DELIVERY OF SAME

(71) Applicant: Tendyne Holdings, Inc., St. Paul, MN (US)

(72) Inventors: Robert M. Vidlund, Forest Lake, MN (US); Igor Kovalsky, Minnetonka, MN (US); Zachary J. Tegels, Minneapolis, MN (US); Craig A. Ekvall, East Bethel, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 463 days.

(21) Appl. No.: 16/788,382

(22) Filed: Feb. 12, 2020

(65) Prior Publication Data
US 2020/0179111 A1 Jun. 11, 2020

Related U.S. Application Data

(60) Division of application No. 15/654,374, filed on Jul. 19, 2017, now Pat. No. 10,610,356, which is a (Continued)

(51) Int. Cl.
*A61F 2/24* (2006.01)
*A61B 17/04* (2006.01)
*A61B 17/34* (2006.01)

(52) U.S. Cl.
CPC ........ *A61F 2/2418* (2013.01); *A61B 17/0401* (2013.01); *A61F 2/2433* (2013.01); (Continued)

(58) Field of Classification Search
CPC .... A61F 2/2418; A61F 2/2433; A61F 2/2439; A61F 2/2436; A61F 2250/0098; (Continued)

(56) References Cited

U.S. PATENT DOCUMENTS 2,697,008 A 12/1954 Ross
3,409,013 A 11/1968 Berry
(Continued)

FOREIGN PATENT DOCUMENTS

CN 1486161 A 3/2004
CN 1961845 A 5/2007
(Continued)

OTHER PUBLICATIONS

US 9,155,620 B2, 10/2015, Gross et al. (withdrawn)
(Continued)

*Primary Examiner* — Julian W Woo
(74) *Attorney, Agent, or Firm* — Wei & Sleman LLP

(57) ABSTRACT

Apparatus and methods are described herein for use in the delivery of a prosthetic mitral valve. In some embodiments, an apparatus includes an epicardial pad configured to engage an outside surface of a heart to secure a prosthetic heart valve in position within the heart. The epicardial pad defines a lumen configured to receive therethrough a tether extending from the prosthetic valve. The epicardial pad is movable between a first configuration in which the epicardial pad has a first outer perimeter and is configured to be disposed within a lumen of a delivery sheath and a second configuration in which the epicardial pad has a second outer perimeter greater than the first outer perimeter. The epicardial pad can be disposed against the outside surface of the heart when in the second configuration to secure the prosthetic valve and tether in a desired position within the heart.

6 Claims, 61 Drawing Sheets

Related U.S. Application Data continuation of application No. PCT/US2016/016567, filed on Feb. 4, 2016, which is a continuation-in-part of application No. PCT/US2015/014572, filed on Feb. 5, 2015.

(60) Provisional application No. 62/212,803, filed on Sep. 1, 2015, provisional application No. 62/100,548, filed on Jan. 7, 2015, provisional application No. 61/935,899, filed on Feb. 5, 2014.

(52) U.S. Cl.
CPC .......... *A61F 2/2436* (2013.01); *A61F 2/2439* (2013.01); *A61B 2017/0443* (2013.01); *A61B 2017/3425* (2013.01); *A61F 2/2457* (2013.01); *A61F 2220/0016* (2013.01); *A61F 2220/0041* (2013.01); *A61F 2220/0075* (2013.01); *A61F 2220/0083* (2013.01); *A61F 2230/0093* (2013.01); *A61F 2250/0039* (2013.01); *A61F 2250/0063* (2013.01); *A61F 2250/0098* (2013.01)

(58) Field of Classification Search
CPC ...... A61F 2250/0063; A61F 2250/0039; A61F 2230/0093; A61F 2220/0083; A61F 2220/0075; A61F 2220/0041; A61F 2220/0016; A61F 2/2457; A61B 17/0401; A61B 2017/3425; A61B 2017/0443
See application file for complete search history.

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |

(56) References Cited

U.S. PATENT DOCUMENTS

| | | |
|---|---|---|
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,361,137 B2 | 4/2008 | Taylor et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,618,449 B2 | 11/2009 | Tremulis et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |

(56) References Cited

U.S. PATENT DOCUMENTS

| | | |
|---|---|---|
| 7,708,775 B2 | 5/2010 | Rowe et al. |
| 7,748,389 B2 | 7/2010 | Salahieh et al. |
| 7,766,961 B2 | 8/2010 | Patel et al. |
| 7,783,366 B1 | 8/2010 | Morgan et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,556,963 B2 | 10/2013 | Tremulis et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,961,597 B2 | 2/2015 | Subramanian et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,468,526 B2 | 10/2016 | Subramanian et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,848,880 B2 | 12/2017 | Coleman et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 10,016,271 B2 | 7/2018 | Morriss et al. |
| 10,226,334 B2 | 3/2019 | Rowe et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0069593 A1 | 4/2003 | Tremulis et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049211 A1 | 3/2004 | Tremulis et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |

(56) References Cited

U.S. PATENT DOCUMENTS

| | | |
|---|---|---|
| 2004/0210304 A1 | 10/2004 | Seguin et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Altieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251157 A1 | 11/2005 | Saadat et al. |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0074397 A1 | 4/2006 | Shimada |
| 2006/0074484 A1 | 4/2006 | Huber |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0196137 A1 | 9/2006 | Brenzel et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0173931 A1 | 7/2007 | Tremulis et al. |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0109069 A1 | 5/2008 | Coleman et al. |
| 2008/0114442 A1 | 5/2008 | Mitchell et al. |
| 2008/0125861 A1 | 5/2008 | Webler et al. |
| 2008/0140189 A1 | 6/2008 | Nguyen et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0228263 A1 | 9/2008 | Ryan |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2008/0300678 A1 | 12/2008 | Eidenschink et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |

(56) References Cited

U.S. PATENT DOCUMENTS

| | | |
|---|---|---|
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0182417 A1 | 7/2009 | Tremulis et al. |
| 2009/0192601 A1 | 7/2009 | Rafiee et al. |
| 2009/0210047 A1 | 8/2009 | Amplatz et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276038 A1 | 11/2009 | Tremulis et al. |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0004740 A1 | 1/2010 | Seguin et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0121435 A1 | 5/2010 | Subramanian et al. |
| 2010/0121437 A1 | 5/2010 | Subramanian et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280589 A1 | 11/2010 | Styrc |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0022157 A1 | 1/2011 | Essinger et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0213459 A1 | 9/2011 | Garrison et al. |
| 2011/0218619 A1 | 9/2011 | Benichou et al. |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0010700 A1 | 1/2012 | Spenser |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0109079 A1 | 5/2012 | Asleson et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0245678 A1 | 9/2012 | Solem |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0103140 A1 | 4/2013 | Subramanian et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0226290 A1 | 8/2013 | Yellin et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0304200 A1 | 11/2013 | McLean et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2013/0338764 A1 | 12/2013 | Thornton et al. |
| 2014/0005778 A1 | 1/2014 | Buchbinder et al. |
| 2014/0031924 A1 | 1/2014 | Bruchman et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243857 A1 | 8/2014 | Miller et al. |
| 2014/0243965 A1 | 8/2014 | Benson et al. |
| 2014/0243966 A1 | 8/2014 | Garde et al. |
| 2014/0257466 A1 | 9/2014 | Board et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358222 A1 | 12/2014 | Gorman, III et al. |

(56) References Cited

U.S. PATENT DOCUMENTS

| | | |
|---|---|---|
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Mdlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |
| 2015/0216660 A1 | 8/2015 | Pintor |
| 2015/0223820 A1 | 8/2015 | Olson |
| 2015/0223934 A1 | 8/2015 | Vidlund et al. |
| 2015/0223935 A1 | 8/2015 | Subramanian et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean |
| 2015/0335424 A1 | 11/2015 | McLean |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan |
| 2016/0120673 A1 | 5/2016 | Siegel et al. |
| 2016/0143736 A1 | 5/2016 | Vidlund |
| 2016/0151155 A1 | 6/2016 | Lutter et al. |
| 2016/0206280 A1 | 7/2016 | Vidlund et al. |
| 2016/0242902 A1 | 8/2016 | Morriss |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0071733 A1 | 3/2017 | Ghione et al. |
| 2017/0079790 A1 | 3/2017 | Vidlund et al. |
| 2017/0100245 A1 | 4/2017 | Subramanian et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2017/0325842 A1 | 11/2017 | Siegel |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |
| 2018/0193138 A1 | 7/2018 | Vidlund |
| 2018/0296212 A1 | 10/2018 | Jimenez et al. |
| 2019/0167407 A1 | 6/2019 | Schaer et al. |
| 2020/0179111 A1 | 6/2020 | Vidlund et al. |

FOREIGN PATENT DOCUMENTS

| | | |
|---|---|---|
| CN | 2902226 Y | 5/2007 |
| CN | 101146484 A | 3/2008 |
| CN | 101180010 A | 5/2008 |
| CN | 101484093 | 7/2009 |
| CN | 101180010 | 12/2010 |
| CN | 101984938 A | 3/2011 |
| CN | 102639179 A | 8/2012 |
| CN | 102791223 A | 11/2012 |
| CN | 102869317 A | 1/2013 |
| CN | 102869318 A | 1/2013 |
| CN | 102869321 A | 1/2013 |
| CN | 103220993 A | 7/2013 |
| CN | 103974674 A | 8/2014 |
| CN | 102639179 B | 10/2014 |
| CN | 104941016 | 9/2015 |
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043830 A1 | 4/2009 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 | 10/2004 |
| EP | 1469797 B1 | 11/2005 |
| EP | 2111800 A1 | 10/2009 |
| EP | 2193762 A1 | 6/2010 |
| EP | 2278944 A2 | 2/2011 |
| EP | 2747707 A1 | 7/2014 |
| EP | 2918248 A1 | 9/2015 |
| FR | 2788217 A1 | 7/2000 |
| FR | 2815844 A1 | 5/2002 |
| FR | 2815844 A1 | 5/2002 |
| JP | 2003505146 A | 2/2003 |
| JP | 2005515836 A | 6/2005 |
| JP | 2009514628 A | 4/2009 |
| JP | 2009519783 A | 5/2009 |
| JP | 2010517623 A | 5/2010 |
| JP | 2013512765 A | 4/2013 |
| JP | 2014532457 A | 12/2014 |
| NL | 1017275 C2 | 8/2002 |
| SU | 1271508 A1 | 11/1986 |
| WO | 9217118 A1 | 10/1992 |
| WO | 9301768 A1 | 2/1993 |
| WO | 9829057 | 7/1998 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 2000041652 | 7/2000 |
| WO | 2000047139 A1 | 8/2000 |
| WO | 2001035878 A2 | 5/2001 |
| WO | 2001049213 A2 | 7/2001 |
| WO | 2001054624 A1 | 8/2001 |
| WO | 2001054625 A1 | 8/2001 |
| WO | 2001056512 A1 | 8/2001 |
| WO | 2001061289 A1 | 8/2001 |
| WO | 0176510 A2 | 10/2001 |

(56) References Cited

FOREIGN PATENT DOCUMENTS

| | | |
|---|---|---|
| WO | 2001076510 A2 | 10/2001 |
| WO | 0182840 | 11/2001 |
| WO | 2001082840 A1 | 11/2001 |
| WO | 2002004757 A1 | 1/2002 |
| WO | 0222054 A1 | 3/2002 |
| WO | 2002022054 A1 | 3/2002 |
| WO | 2002028321 A2 | 4/2002 |
| WO | 0236048 A1 | 5/2002 |
| WO | 2002036048 A1 | 5/2002 |
| WO | 2002041789 A2 | 5/2002 |
| WO | 0243620 A1 | 6/2002 |
| WO | 0249540 A2 | 6/2002 |
| WO | 2002043620 A1 | 6/2002 |
| WO | 2002049540 A2 | 6/2002 |
| WO | 2002076348 A1 | 10/2002 |
| WO | 2003003943 A2 | 1/2003 |
| WO | 2003030776 A2 | 4/2003 |
| WO | 2003047468 A1 | 6/2003 |
| WO | 2003049619 A2 | 6/2003 |
| WO | 2004019825 A1 | 3/2004 |
| WO | 2005102181 A1 | 11/2005 |
| WO | 2006014233 A2 | 2/2006 |
| WO | 2006034008 A2 | 3/2006 |
| WO | 2006064490 A1 | 6/2006 |
| WO | 2006070372 A2 | 7/2006 |
| WO | 2006105009 A1 | 10/2006 |
| WO | 2006113906 A1 | 10/2006 |
| WO | 2006127756 A2 | 11/2006 |
| WO | 2007081412 A1 | 7/2007 |
| WO | 2007100408 A2 | 9/2007 |
| WO | 2008005405 A2 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2009024859 A2 | 2/2009 |
| WO | 2009026563 A2 | 2/2009 |
| WO | 2009045338 A1 | 4/2009 |
| WO | 2009132187 A1 | 10/2009 |
| WO | 2010090878 A2 | 8/2010 |
| WO | 2010098857 A1 | 9/2010 |
| WO | 2010121076 A2 | 10/2010 |
| WO | 2011017440 A2 | 2/2011 |
| WO | 2011022658 A1 | 2/2011 |
| WO | 2011069048 A2 | 6/2011 |
| WO | 2011072084 A2 | 6/2011 |
| WO | 2011106735 A1 | 9/2011 |
| WO | 2011109813 A2 | 9/2011 |
| WO | 2011159342 A1 | 12/2011 |
| WO | 2011163275 A2 | 12/2011 |
| WO | 2012027487 A2 | 3/2012 |
| WO | 2012036742 A2 | 3/2012 |
| WO | 2012095116 A1 | 7/2012 |
| WO | 2012177942 A2 | 12/2012 |
| WO | 2013028387 A2 | 2/2013 |
| WO | 2013045262 A1 | 4/2013 |
| WO | 2013059747 A1 | 4/2013 |
| WO | 2013028387 | 5/2013 |
| WO | 2013096411 A1 | 6/2013 |
| WO | 2013096757 A1 | 6/2013 |
| WO | 2013116785 A1 | 8/2013 |
| WO | 2013175468 A2 | 11/2013 |
| WO | 2014121280 A2 | 8/2014 |
| WO | 2014138284 A1 | 9/2014 |
| WO | 2014144020 A1 | 9/2014 |
| WO | 2014144937 A2 | 9/2014 |
| WO | 2014162306 A2 | 10/2014 |
| WO | 2014189974 A1 | 11/2014 |
| WO | 2014194178 A1 | 12/2014 |
| WO | 2014210124 A1 | 12/2014 |
| WO | 2015051430 A1 | 4/2015 |
| WO | 2015058039 A1 | 4/2015 |
| WO | 2015063580 A2 | 5/2015 |
| WO | 2015065646 A1 | 5/2015 |
| WO | 2015120122 A2 | 8/2015 |
| WO | 2015138306 A2 | 9/2015 |
| WO | 2015173609 A1 | 11/2015 |
| WO | 2016112085 A2 | 7/2016 |
| WO | 2016126942 A2 | 8/2016 |
| WO | 2016168609 A1 | 10/2016 |
| WO | 2016196933 A1 | 12/2016 |
| WO | 2017096157 A1 | 6/2017 |
| WO | 2017132008 A1 | 8/2017 |
| WO | 2017218375 A1 | 12/2017 |
| WO | 2018005779 A1 | 1/2018 |
| WO | 2018013515 A1 | 1/2018 |

OTHER PUBLICATIONS

"Shape Memory Alloys," Retrieved from the Internet: <http://webdocs.cs.ualberta.ca/.about.database/MEMS/sma.html>, Nov. 14, 2012, 3 pages.

Australian Search Report for Application No. AU 2016215197 dated Sep. 12, 2019.

Chinese Search Report for CN Application No. 201680013223.9, dated Oct. 29, 2018.

International Search Report and Written Opinion for International Application No. PCT/US2016/012305, dated Aug. 3, 2016, 18 pages.

US 9,155,620, 10/2015, Gross et al. (withdrawn).

"Shape Memory Alloys," Retrieved from the Internet: <http://webdocs.cs.ualberta.ca/~database/MEMS/sma.html>, Feb. 5, 2016, 3 pages.

Al Zaibag, Muayed, et al., "Percutaneous Balloon Valvotomy in Tricuspid Stenos's," British Heart Journal, Jan. 1987, vol. 57, No. 1, pp. 51-53.

Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.

Almagor, Y. et al., "Balloon Expandable Stent Implantation in Stenotic Right Heart Valved Conduits," Journal of the American College of Cardiology, Nov. 1, 1990, 16(6):1310-1314.

Andersen, H. R., "History of Percutaneous Aortic Valve Prosthesis," Herz, Aug. 2009, 34(5):343-346.

Andersen, H. R., "Transluminal catheter implanted prosthetic heart valves," International Journal of Angiology, 1998, 7(2):102-106.

Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.

Boudjemline, Y. et al., "Steps Toward the Percutaneous Replacement of Atrioventricular Valves: An Experimental Study," Journal of the American College of Cardiology, Jul. 2005, 46(2):360-365.

Buckberg, G. et al., "Restoring Papillary Muscle Dimensions During Restoration in Dilated Hearts," Interactive Cardiovascular and Thoracic Surgery, 2005, 4:475-477.

Chamberlain, G., "Ceramics Replace Body Parts," Design News, Jun. 9, 1997, Issue 11, vol. 52, 5 pages.

Choo, S. J. et al., "Aortic Root Geometry: Pattern of Differences Between Leaflets and Sinuses of Valsava," The Journal of Heart Valve Disease, Jul. 1999, 8:407-415.

Cullen, et al., "Transvenous, Antegrade Melody Valve-in-Valve Implantation for Bioprosthetic Mitral and Tricuspid Valve Dysfunction", JACC: Cardiovascular Interventions, vol. 6, No. 6, Jun. 2013, pp. 598-605.

Declaration of Malcolm J. R. Dalrymple-Hay, Nov. 9, 2012, pp. 1-11; with Curriculum Vitae, Oct. 4, 2012.

Dotter, C. T. et al., "Transluminal Treatment of Arteriosclerotic Obstruction. Description of a New Technic and a Preliminary Report of its Application," Circulation, Nov. 1964, 30:654-670.

Drawbaugh, K., "Feature—Heart Surgeons Explore Minimally Invasive Methods," Reuters Limited, Jul. 16, 1996, 3 pages.

G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.

(56) References Cited

OTHER PUBLICATIONS

Gray, H., The Aorta, Anatomy of the Human Body, 1918, Retrieved from the Internet <http://www.bartleby.com/107/142.html>, Dec. 10, 2012, 5 pages.

Gray, H., The Heart, Anatomy of the Human Body, 1918, Retrieved from the Internet <http://education.yahoo.com/reference/gray/subjects/subject/138>, Aug. 10, 2012, 9 pages.

Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.

H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.

Inoue, K. et al., "Clinical Application of Transvenous Mitral Commissurotomy by a New Balloon Catheter," The Journal of Thoracic and Cardiovascular Surgery, 1984, 87:394-402.

International Search Report and Written Opinion for International Application No. PCT/US2016/016567, dated Aug. 3, 2016, 17 pages.

Jin, X. Y. et al., "Aortic Root Geometry and Stentless Porcine Valve Competence," Seminars in Thoracic and Cardiovascular Surgery, Oct. 1999, 11(4):145-150.

Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.

Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili ...,>, published Jan. 3, 1991,retrieved from the Internet on Feb. 5, 2016, 3 pages.

Lawrence, D. D., "Percutaneous Endovascular Graft: Experimental Evaluation," Radiology, 1987, 163:357-360.

Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.

Lutter, G. et al., "Mitral Valved Stent Implantation," European Journal of Cardia-Thoracic Surgery, 2010, 38:350-355, 2 pages.

Ma, L. et al., "Double-crowned valved stents for off-pump mitral valve replacement," European Journal of Cardio-Thoracic Surgery, Aug. 2005, 28(2): 194-198.

Moazami, N. et al., "Transluminal aortic valve placement: A feasibility study with a newly designed collapsible aortic valve," ASAIO Journal, Sep./ Oct. 1996, 42(5):M381-M385.

Orton, C., "Mitralseal: Hybrid Transcatheter Mitral Valve Replacement," Symposium: Small Animal Proceedings, 2011, pp. 311-312.

Pavcnik, D. et al. "Development and Initial Experimental Evaluation of a Prosthetic Aortic Valve for Transcatheter Placement," Radiology, 1992; 183:151-154.

Porstmann, W. et al., "Der Verschlul?. des Ductus Arteriosus Persistens ohne Thorakotomie," Thoraxchirurgie Vaskulare Chirurgie, Band 15, Heft 2, Stuttgart, Apr. 1967, pp. 199-203.

Rashkind, W. J., "Creation of an Atrial Septal Defect Without Thoracotomy," The Journal of the American Medical Association, Jun. 13, 1966, 196( 11 ): 173-174.

Rashkind, W. J., "Historical Aspects of Interventional Cardiology: Past, Present, Future," Texas Heart Institute Journal, Dec. 1986, 13(4):363-367.

Reul, H. et al., "The Geomety of the Aortic Root in Health, at Valve Disease and After Valve Replacement," J. Biomechanics, 1990, 23(2):181-191.

Robert C. Ashton Jr., "Development of an Intraluminal Device for the Treatment of Aortic Regurgitation: Prototype and in Vitro Testing System," Journal of Thoracic and Cardiovascular Surgery, 1996, Issue/vol. 112, pp. 979-983.

Rosch, J. et al., "The Birth, Early Years and Future of Interventional Radiology," J Vase Interv Radiol., Jul. 2003, 4:841-853.

Ross, D. N., "Aortic Valve Surgery," Guy's Hospital, London, 1968, pp. 192-197.

Rousseau, E. P. M. et al., "A Mechanical Analysis of the Closed Hancock Heart Valve Prosthesis," Journal of Biomechanics, 1998, 21(7):545-562.

Sabbah, A. N. et al., "Mechanical Factors in the Degeneration of Porcine Bioprosthetic Valves: An Overview," Dec. 1989, Journal of Cardiac Surgery, 4(4):302-309.

Selby, M.D., J. Bayne, "Experience with New Retrieval Forceps for Foreign Body Removal in the Vascular, Urinary, and Biliary Systems," Radiology 1990; 176:535-538.

Serruys, P.W., et al., "Stenting of Coronary Arteries. Are we the Sorcerer's Apprentice?," European Heart Journal (1989) 10, 774-782, pp. 37-45, Jun. 13, 1989.

Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.

Tofeig, M. et al., "Transcatheter Closure of a Mid-Muscular Ventricular Septal Defect with an Amplatzer VSD Occluder Device," Heart, 1999, 81:438-440.

Uchida, Barry T., et al., "Modifications of Gianturco Expandable Wire Stents," AJR:150, May 1988, Dec. 3, 1987, pp. 1185-1187.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.

Webb, J. G. et al., "Percutaneous Aortic Valve Implantation Retrograde from the Femoral Artery," Circulation, 2006, 113:842-850.

Wheatley, M.D., David J., "Valve Prostheses," Rob & Smith's Operative Surgery, Fourth Edition, pp. 415-424, ButtenNorths 1986.

Yoganathan, A. P. et al., "The Current Status of Prosthetic Heart Valves," In Polymetric Materials and Artificial Organs, Mar. 20, 1983, pp. 111-150, American Chemical Society.

A. P. Yoganathan et al., "The Current Status of Prosthetic Heart Valves, Polymetric Materials and Artificial Organs," American Chemical Society , Mar. 20, 1983 pp. 111-150.

Al Zaibag, M. et al., "Percutaneous Balloon Valvotomy in Tricuspid Stenosis," British Heart Journal, Jan. 1987, 57(1):51-53.

Bernacca, G. M. et al., "Polyurethane heart valves: Fatigue failure, calcification, and polyurethane structure," Journal of Biomedical Materials Research, Mar. 5, 1997, 34(3):371-379.

Henning Rud Andersen, "Transluminal Catheter Implanted Prosthetic Heart Valves," International Journal of Angiology, 1998, Issue 2, vol. 7 pp. 102-106.

Lutter, Georg, et al., "Mitral Valved Stent Implantation," European Journal of Cardio-Thoracic Surgery, 2010, vol. 38pp. 350-355.

Rousseau, E. P. M. et al., "A mechanical analysis of the closed Hancock heart valve prosthesis," Journal of Biomechanics, 1988, 21(7):545-562.

International Search Report for Appln. No. PCT/US2021/040996 dated Oct. 21, 2021. (3 pages).

EXPANDABLE EPICARDIAL PADS AND DEVICES AND METHODS FOR DELIVERY OF SAME

This application is a divisional of U.S. patent application Ser. No. 15/654,374, filed Jul. 19, 2017, which is a continuation of International PCT Application No. PCT/US2016/016567, entitled "Expandable Epicardial Pads and Devices and Methods for Delivery of Same," filed Feb. 4, 2016, which claims priority to and is a continuation-in-part of International PCT Application No. PCT/US2015/014572, entitled "Apparatus and Methods for Transfemoral Delivery of Prosthetic Mitral Valve," filed Feb. 5, 2015, which claims priority to and the benefit of U.S. Provisional Patent Application Ser. No. 61/935,899, entitled "Transfemoral Delivery of Prosthetic Mitral Valve," filed Feb. 5, 2014, and U.S. Provisional Patent Application No. 62/100,548, entitled "Apparatus and Methods for Transfemoral Delivery of Prosthetic Mitral Valve," filed Jan. 7, 2015. The disclosure of each of the above applications is incorporated herein by reference in its entirety.

International PCT Application No. PCT/US2016/016567 also claims priority to and the benefit of U.S. Provisional Patent Application No. 62/212,803, entitled "Dilator Devices and Methods for Epicardial Pad Delivery," filed Sep. 1, 2015, the disclosure of which is incorporated herein by reference in its entirety.

International PCT Application No. PCT/US2016/016567 is also related to International PCT Application No. PCT/US2014/0049218, entitled "Epicardial Anchor Devices and Methods," filed Jul. 31, 2014, the disclosure of which is incorporated herein by reference in its entirety.

BACKGROUND

Embodiments are described herein that relate to devices and methods for delivery and deployment of prosthetic valves and epicardial pads.

Prosthetic heart valves can pose particular challenges for delivery and deployment within a heart. Valvular heart disease, and specifically, aortic and mitral valve disease is a significant health issue in the United States (US); annually approximately 90,000 valve replacements are conducted in the US. Traditional valve replacement surgery involving the orthotopic replacement of a heart valve is considered an "open heart" surgical procedure. Briefly, the procedure necessitates surgical opening of the thorax, the initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated to the procedure largely due to the necessity for extra-corporeal circulation. Further, open heart surgery is often poorly tolerated in elderly patients. Thus elimination of the extra-corporeal component of the procedure could result in reduction in morbidities and cost of valve replacement therapies could be significantly reduced.

While replacement of the aortic valve in a transcatheter manner is the subject of intense investigation, lesser attention has been focused on the mitral valve. This is in part reflective of the greater level of complexity associated to the native mitral valve apparatus, and thus, a greater level of difficulty with regards to inserting and anchoring the replacement prosthesis. A need exists for delivery devices and methods for transcatheter mitral valve replacements.

SUMMARY

Devices and methods for use in the delivery and deployment of a prosthetic valve and an epicardial pad are described herein. As described herein, in some embodiments, a method includes delivering and deploying an expandable tissue dilator device. The expandable tissue dilator device can be used to dilate tissue or otherwise create space near an apex of a heart. In some embodiments, after a prosthetic mitral valve has been deployed within the heart via a transfemoral, transapical or other suitable delivery approach, a tether attached to the prosthetic valve can extend outside the apex of the heart. The tissue dilator can be used to dilate tissue or otherwise create space for delivery and/or deployment of an epicardial pad device near the apex of the heart to secure the tether and the prosthetic valve in a desired position. In some embodiments, the epicardial pad can be an expandable epicardial pad.

DETAILED DESCRIPTION

Figure 1:
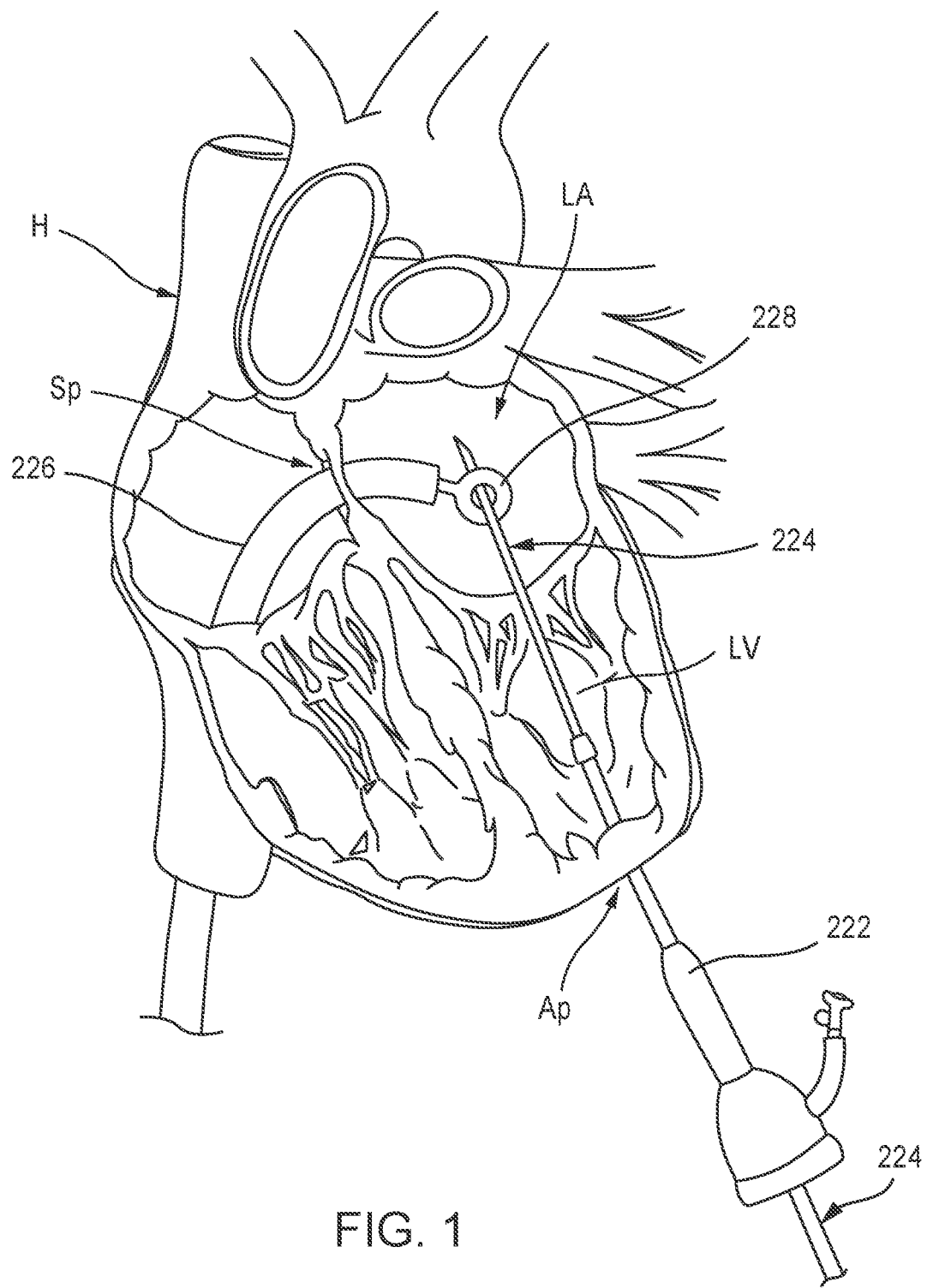
FIGS. 1-6 are each a cross-sectional illustration of a heart with devices used during various stages in a procedure to transfemorally deliver and deploy a prosthetic mitral valve.

Devices and methods for use in the delivery and deployment of prosthetic mitral valves and epicardial pads are described herein. As described herein, in some embodiments, a method includes delivering and deploying an expandable tissue dilator device. The expandable tissue dilator device can be used to dilate tissue or otherwise create space near an apex region of a heart. In some embodiments, after a prosthetic mitral valve has been deployed within the heart via a transcatheter or other suitable delivery approach, a tether attached to the prosthetic valve can extend outside the apex of the heart. The tissue dilator device can be used to dilate tissue or otherwise create space for delivery and/or deployment of an epicardial pad device at the apex region of the heart to secure the tether and the prosthetic valve in a desired position.

The prosthetic valve can be delivered to within a patient's heart using a variety of different delivery approaches for delivering a prosthetic heart valve (e.g., prosthetic mitral valve). For example, the prosthetic valves described herein can be delivered using a transfemoral delivery approach as described in International Application No. PCT/US15/14572 (the '572 PCT application) incorporated by reference above, or via a transatrial approach, such as described in U.S. Provisional Patent Application Ser. No. 62/220,704, entitled "Apparatus and Methods for Transatrial Delivery of Prosthetic Mitral Valve," filed Sep. 18, 2015 ("the '704 provisional application"), which is incorporated herein by reference in its entirety. In another example, a prosthetic mitral valve as described herein can be delivered via a transjugular approach, via the right atrium and through the atrial septum and into the left atrium. The prosthetic valves described herein can also be delivered apically if desired.

In some embodiments, an apparatus includes an epicardial pad configured to engage an outside surface of a heart to secure a prosthetic heart valve in position within the heart. The prosthetic heart valve has a tether extending therefrom and outside the heart when the prosthetic heart valve is disposed within the heart. The epicardial pad defines a lumen configured to receive the tether therethrough. The epicardial pad is movable between a first configuration in which the epicardial pad has a first outer perimeter and is configured to be disposed within a lumen of a delivery sheath and a second configuration in which the epicardial pad has a second outer perimeter greater than the first outer perimeter. The epicardial pad can be disposed against the outside surface of the heart when in the second configuration to secure the prosthetic valve and tether in a desired position within the heart.

In some embodiments, an apparatus includes a delivery sheath that defines a first lumen and a dilator device that defines a second lumen and is movably disposed within the first lumen of the delivery sheath. The dilator device includes an elongate member and an expandable member disposed at a distal end of the elongate member. The expandable member has a collapsed configuration and an expanded configuration. The dilator device is in the collapsed configuration when disposed within the first lumen. An epicardial pad having a collapsed configuration and an expanded configuration is configured to be disposed within the second lumen when in the collapsed configuration. The epicardial pad is configured to be disposed against an outside surface of a heart when in the expanded configuration. The dilator member of the dilator device is configured to dilate tissue associated with the outside surface of the heart when moved from its collapsed configuration to its expanded configuration such that a space is formed in which the epicardial pad can be disposed.

In some embodiments, a method includes disposing a distal end portion of a delivery sheath outside a surface of a heart near an apex of the heart. The delivery sheath has a dilator device movably disposed within a lumen of the delivery sheath. The dilator device includes an elongate member and a dilator member disposed at a distal end portion of the elongate member, and is movable from a collapsed configuration when disposed within the lumen of the delivery sheath and an expanded configuration. After disposing the delivery sheath outside a surface of the heart, the dilator member of the dilator device is disposed outside a distal end of the delivery sheath, and is moved to the expanded configuration such that tissue associated with the surface of the heart is dilated from pressure exerted on the tissue by the dilator member and a space is formed to receive an epicardial pad device.

In some embodiments, a method includes disposing a distal end portion of a delivery sheath outside a surface of a heart near an apex of the heart. The delivery sheath has an epicardial pad disposed within a lumen of the delivery sheath. The epicardial pad has a collapsed configuration when disposed within the lumen of the delivery sheath and an expanded configuration. The epicardial pad defines an opening and has a tether extending through the opening. The tether is coupled to a prosthetic heart valve implanted within the heart. The epicardial pad is disposed outside a distal end of the delivery sheath and outside the surface of the heart near the apex of the heart. The epicardial pad is secured in the expanded configuration to the outside surface of the heart to secure the prosthetic heart valve and the tether in a desired position.

Figure 2:
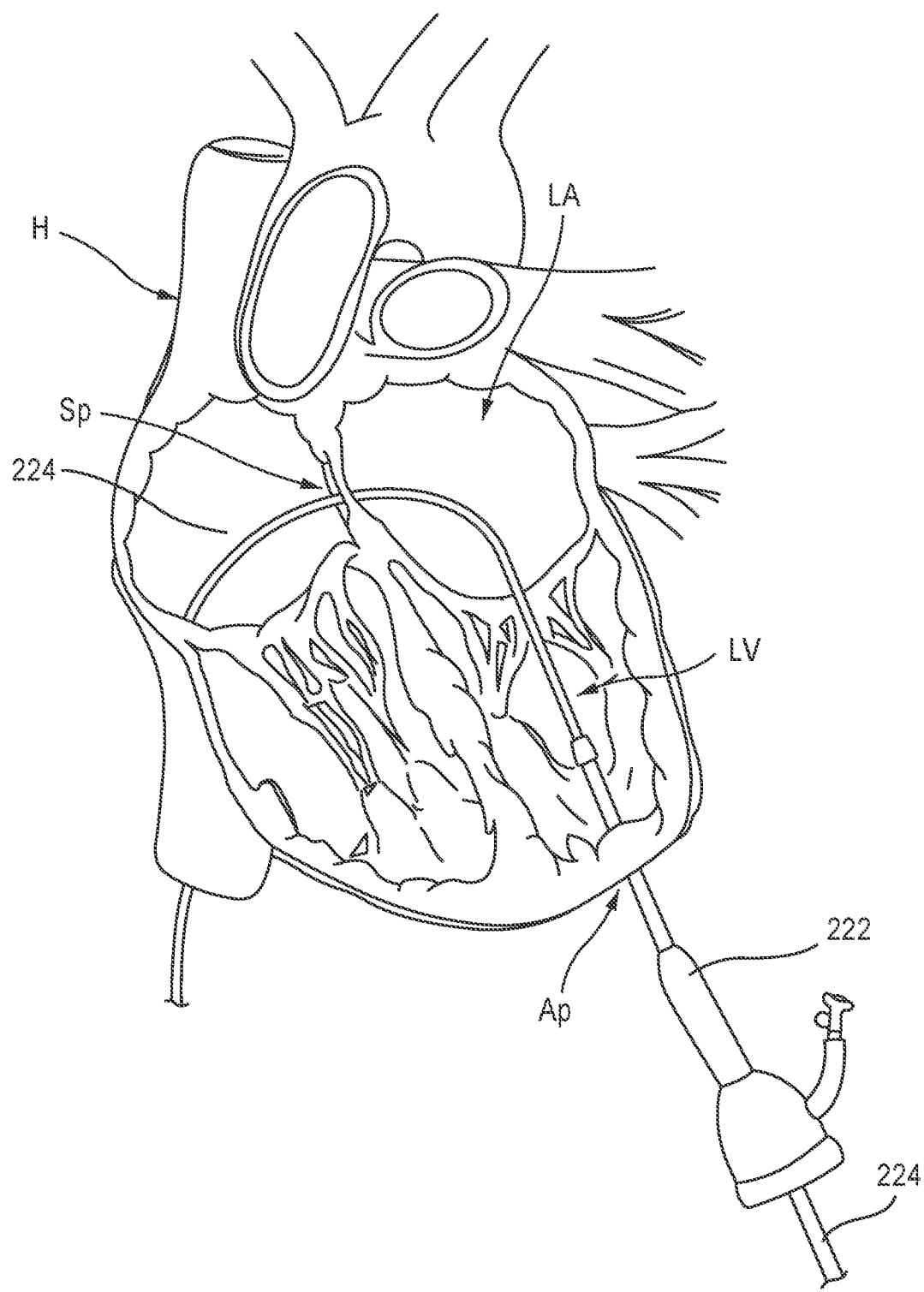

FIGS. 1-6 illustrate one example method of delivering a prosthetic mitral valve 200 (shown in FIGS. 3-6) to a left atrium LA of a heart H via introduction through a femoral vein. As shown in FIG. 1, a procedural catheter 222 is inserted through an apical puncture (e.g., a 5F apical puncture) in a ventricular wall at the apex Ap of the heart H. A leader tube 224 is inserted through a lumen (not shown) of the procedural catheter 222 and extended through the left ventricle LV, through a mitral valve gap and into the left atrium LA. A delivery sheath 226 is introduced through a femoral vein puncture and extended through the inferior vena cava, into the right atrium, and then through a transseptal puncture of the septum Sp of the heart H, and into the left atrium LA of the heart H. A snare device 228 is movably disposed within the delivery sheath 226 and used to grab or snare a distal end portion of the leader tube 224, as shown in FIG. 1. The snare device 228 can be used to pull the leader tube 224 through the delivery sheath 226 such that the distal end portion of the leader tube 224 extends outside the femoral vein and a proximal end of the leader tube 224 is disposed through the ventricular wall at the apex Ap of the heart H, as shown in FIG. 2. The leader tube 224 allows for back-loading of the prosthetic mitral valve 200 starting in the femoral vein and exiting the heart H at the apex Ap. Although not shown in FIGS. 1 and 2, the procedural catheter 224 is disposed outside the patient's body, the distal end of the leader tube 224 extends outside the femoral vein and outside the patient's body, and the proximal end of the leader tube 224 extends outside the apex Ap and outside the patient's body. Although the above described snare process describes delivering the leader tube 224 to the left atrium of the heart and then snaring the leader tube 224 using the snare device 228, in alternative embodiments, the leader tube 224 can be delivered to the left ventricle LV and the snare device 228 and delivery sheath 226 can be inserted through the mitral annulus and into the left ventricle LV to grab or snare the leader tube 224 as described above.

After the leader tube 224 has been extended between the apex Ap and the access site to the femoral vein, a valve leader member 234 attached to the prosthetic mitral valve 200 (also referred to as "valve") can be inserted into the leader tube 224 at the femoral end of the leader tube 224 and extended through the leader tube 224 until the valve leader member 234 exits the leader tube at the apex end of the leader tube 224. After the valve leader member 234 is inserted and extended outside the apex Ap, the leader tube 224 can be removed from the patient. For example, the leader tube 224 can be pulled out through the apex puncture site, or through the femoral vein puncture site. Thus, only the valve leader member 234 remains disposed within the body, as shown in FIG. 3.

Figure 26:
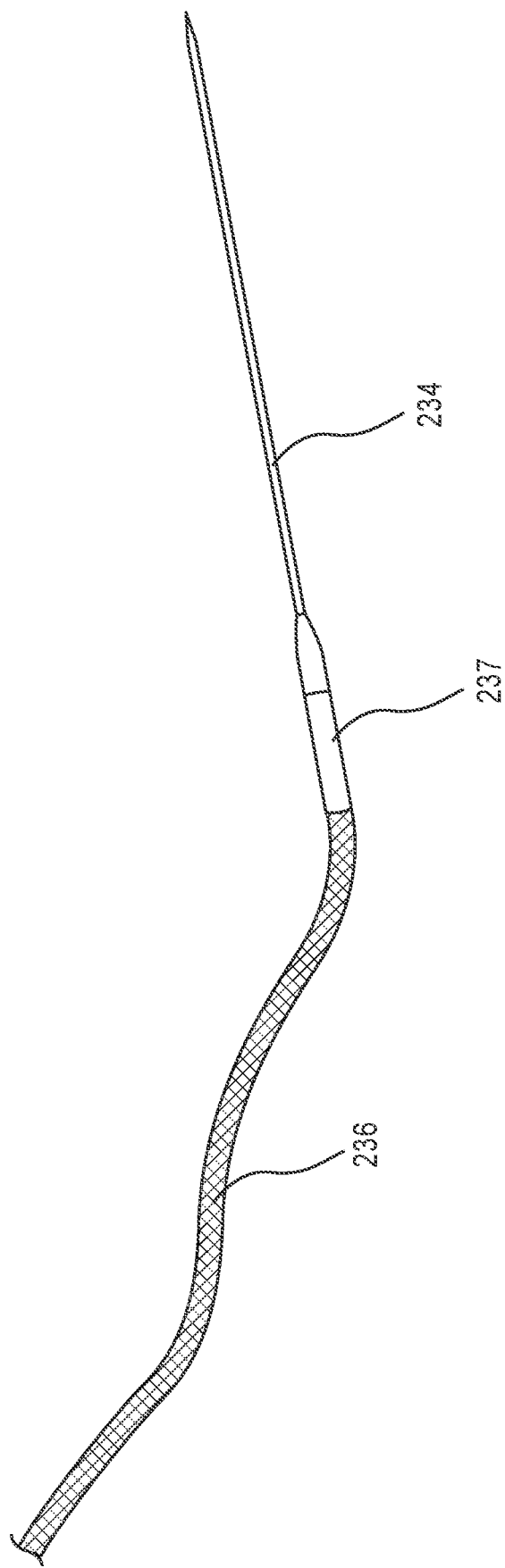
FIG. 26 is a side view illustrating a portion of a tether coupled to a portion of a valve leader member, according to an embodiment.

The valve leader member 234 can have a tapered distal end 235 to aid in the insertion and maneuvering of the valve leader member 234 through the leader tube 224. The valve leader member 234 is attached at a proximal end portion 237 to a tether line 236 (also referred to herein as "tether"), which is attached to the valve 200. FIG. 26 illustrates an enlarged view of the attachment of the proximal end portion 237 to tether 236. The tether 236 can be formed, for example, as a braided rope or cord as shown, for example, in FIG. 26.

Figure 3:
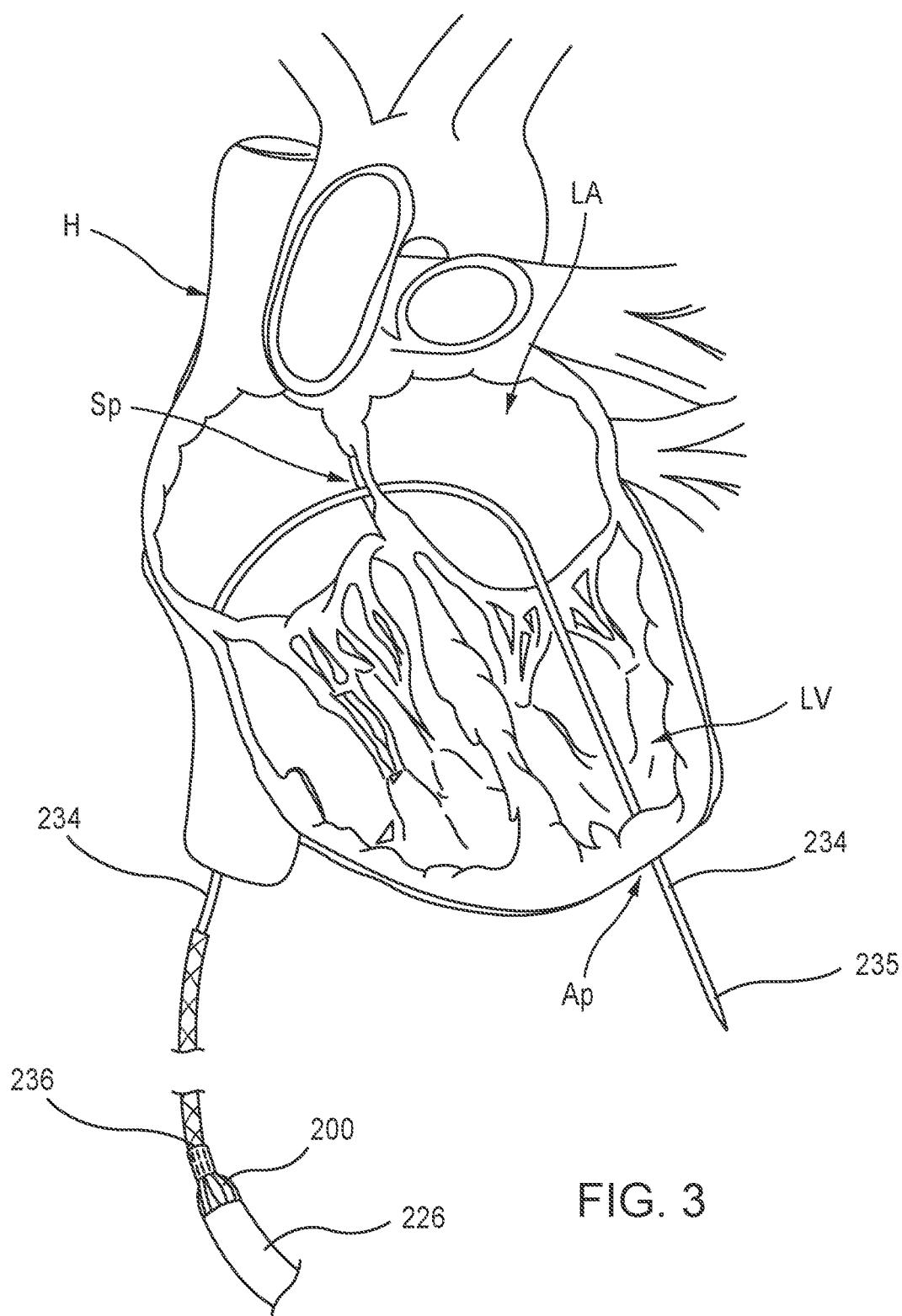

As shown in FIG. 3, the valve 200 is partially disposed within a lumen of the delivery sheath 226. Although the delivery sheath 226 is used to deliver both the snare device 228 and the valve 200, in other embodiments, a different delivery sheath can be used to deliver the snare device 228 than is used to deliver the valve 200. As shown in FIG. 3, prior to inserting the valve leader member 234 into the leader tube 224, the procedural catheter 222 can be removed. Alternatively, the procedural catheter 222 can be removed after inserting the valve leader member 234.

Also as shown in FIG. 3, in this embodiment, a portion of the valve 200 is allowed to partially deploy outside a distal end of the delivery sheath 226. The partially deployed portion of the valve 200 can be used as a lead-in to the delivery sheath 226 as the valve 200 is inserted through the femoral vein. For example, the valve 200 can be formed with a shape-memory material (as described in more detail below) and can have a biased undeformed shape and can be manipulated and/or deformed (e.g., compressed and/or expanded) and, when released, return to its original undeformed shape. In some embodiments, the valve 200 can have a biased expanded or undeformed configuration when deployed within a heart, and can be moved to a collapsed or deformed configuration when placed within the lumen of the delivery sheath 226 for delivery through the femoral vein. The valve can be, for example, a valve constructed the same as or similar to, and function in the same or similar manner as, the prosthetic heart valve 500, described in detail below.

Figure 4:
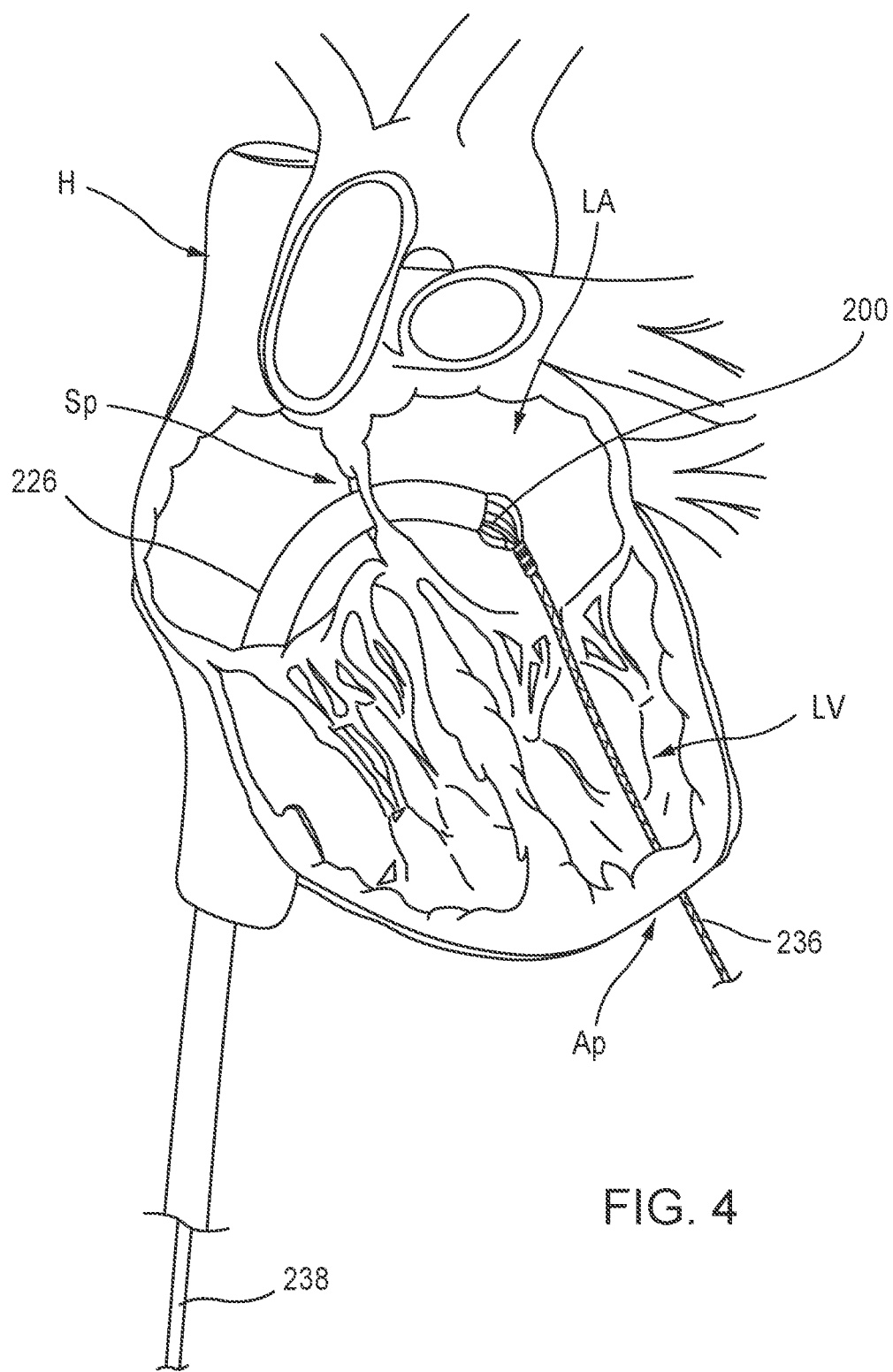

After the valve leader member 234 has been placed in position between the femoral puncture site and the apical puncture site, as described above, the delivery sheath 226 with the valve 200 can be inserted through the femoral puncture site and moved through the femoral vein, through the inferior vena cava, into the right atrium, and then through the septum Sp until a distal end portion of the delivery sheath 226 (with the valve 200) is disposed within the left atrium LA, as shown in FIG. 4. As shown in FIG. 4, the tether 236 extends from the valve 200 through the apical puncture and outside the patient's body. As the delivery sheath 226 is advanced, the tether 236 can optionally be pulled at the apex end to help move the delivery sheath 226, with the valve 200 disposed therein, through the femoral vein, through the septal puncture and into the left atrium LA. The valve 200 can then be fully deployed within the left atrium LA (see, e.g., FIG. 5) by pulling the apex end portion of the tether 236 until the valve 200 is pulled out of the lumen of the delivery sheath 226 and disposed within the left atrium LA. Alternatively, pusher device 238 (see, e.g., FIG. 4) can be inserted within the delivery sheath 226 and used to push the valve 200 outside a distal end of the delivery sheath 226. In yet other embodiments, the pusher device 238 can be used to push the valve 200 while the tether 236 is pulled. In other words, the valve 200 can be deployed by pushing the valve 200 with the pusher device 238, by pulling the valve 200 with the tether 236, or both. The pusher 238 can also be used to aid in positioning the valve 200 in a desired radial orientation within the left atrium LA. For example, the pusher device 238 can define an internal lumen (not shown) that can be placed over an inner frame portion of the valve 200 to hold the inner frame portion in a small diameter, which can help enable the valve 200 to be positioned in a desired radial orientation and be seated within the annulus of the mitral valve. Further examples of such a valve assist device are described below with reference to FIGS. 29-31.

Figure 5:
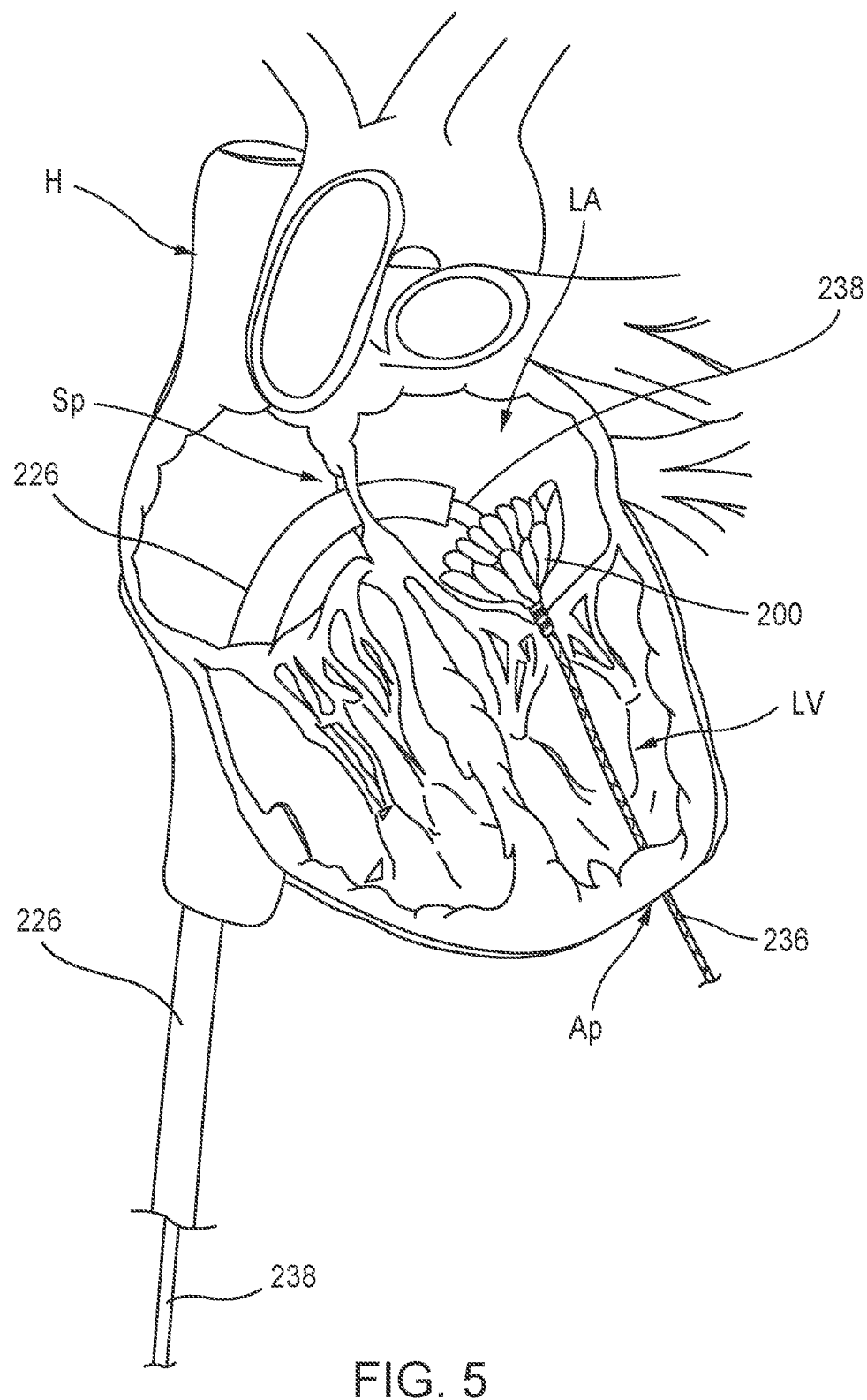
Figure 6:
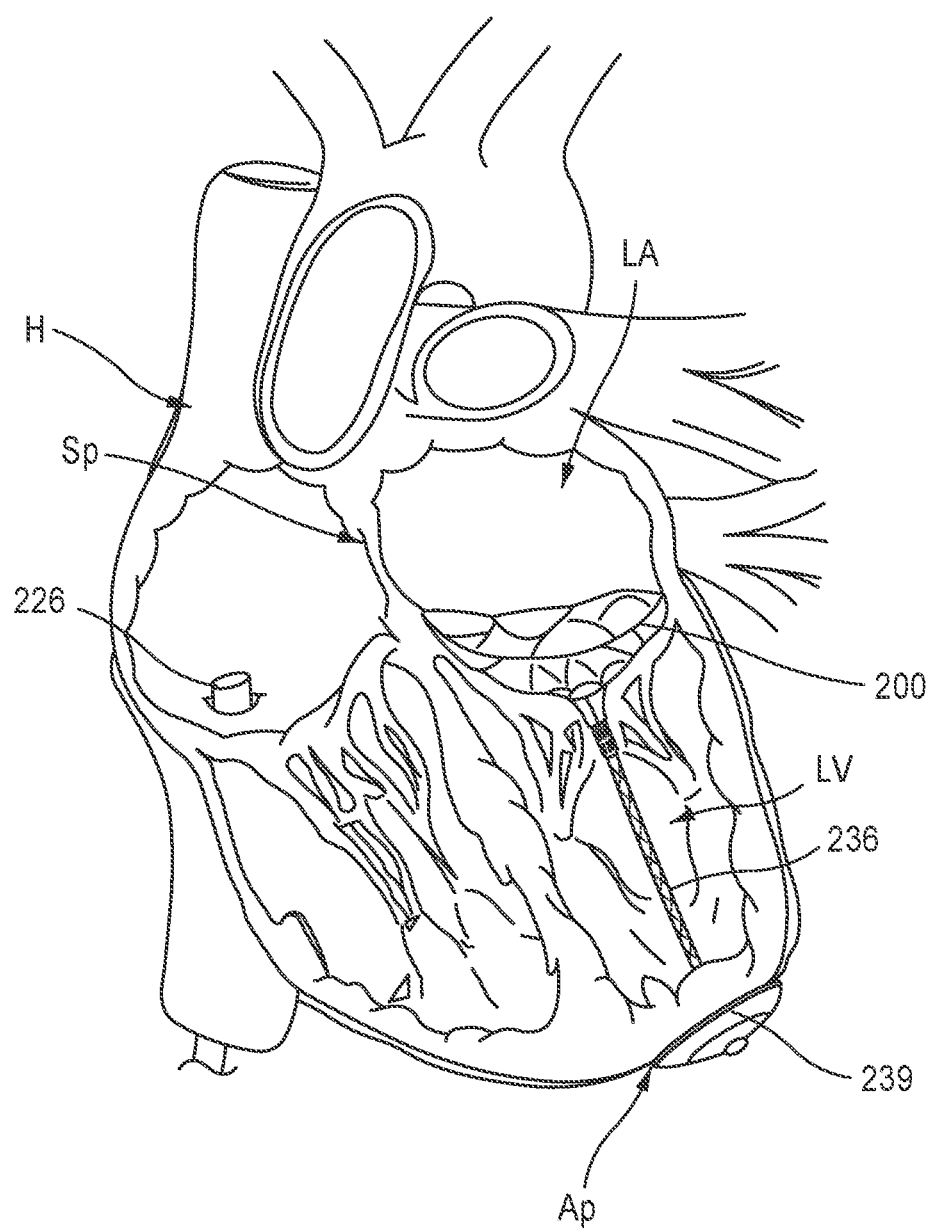

As shown in FIGS. 5 and 6, as the valve 200 is deployed within the left atrium LA, the valve 200 is allowed to assume its biased expanded or deployed configuration. The delivery sheath 226 can then be removed from the patient and the valve 200 can be positioned and tensioned using the tether 236 to obtain the desired or optimal location in the native mitral annulus and minimize perivalvular leaks. An epicardial pad device 239 can be used to secure the tether 236 and valve 200 in position within the mitral annulus as shown in FIG. 6. For example, an epicardial pad device as described in International Patent Application No. PCT/US14/49218 ("the '218 PCT application"), the disclosure of which is incorporated herein by reference in its entirety, can be used. In some embodiments, an expandable epicardial pad can be used to secure the tether and valve in position. Example embodiments of expandable pads that can be used are described herein with reference to FIGS. 33-47. Such a pad can be smaller in size such that the pad can be delivered to the heart via a small incision and small catheter or delivery sheath. In some embodiments, a positioning device (not shown) can be used to help position the valve 200 and deploy the epicardial pad device. For example, a positioning device as described in the '218 PCT application incorporated by reference above, or devices described in International Patent Application No. PCT/US14/61046, the disclosure of which is incorporated herein by reference in its entirety, can be used. In some embodiments, rather than securing the prosthetic mitral valve with a tether and epicardial pad, the prosthetic mitral valve can be secured with clips or other coupling methods to a portion(s) of the mitral valve apparatus and/or the ventricular wall of the heart. For example, such coupling methods are described in International Patent Application No. PCT/US14/58826 ("the '826 PCT application"), the disclosure of which is incorporated herein by reference in its entirety.

Figure 7:
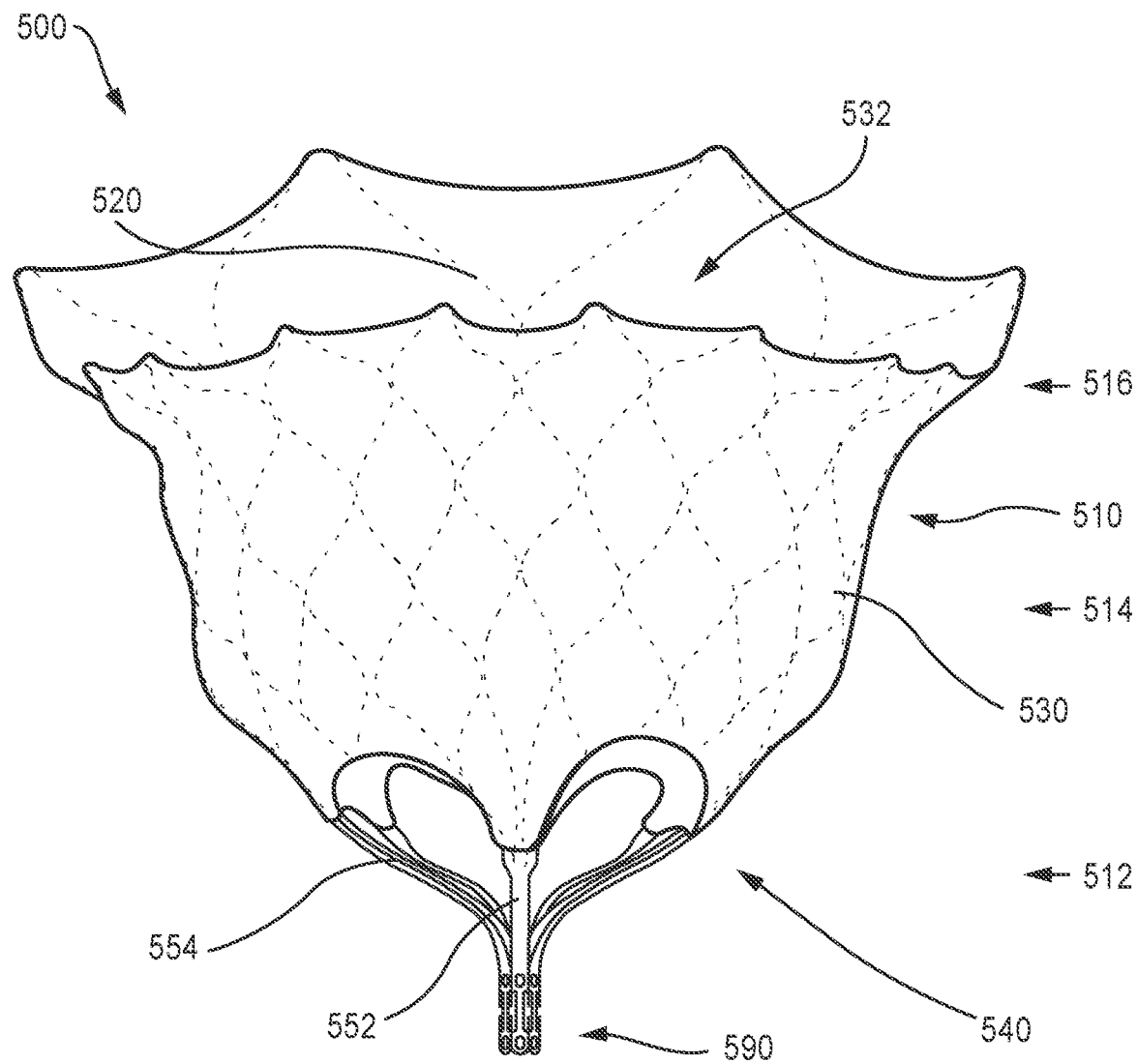
FIGS. 7-9 are front, bottom, and top views of a prosthetic heart valve according to an embodiment.
Figure 8:
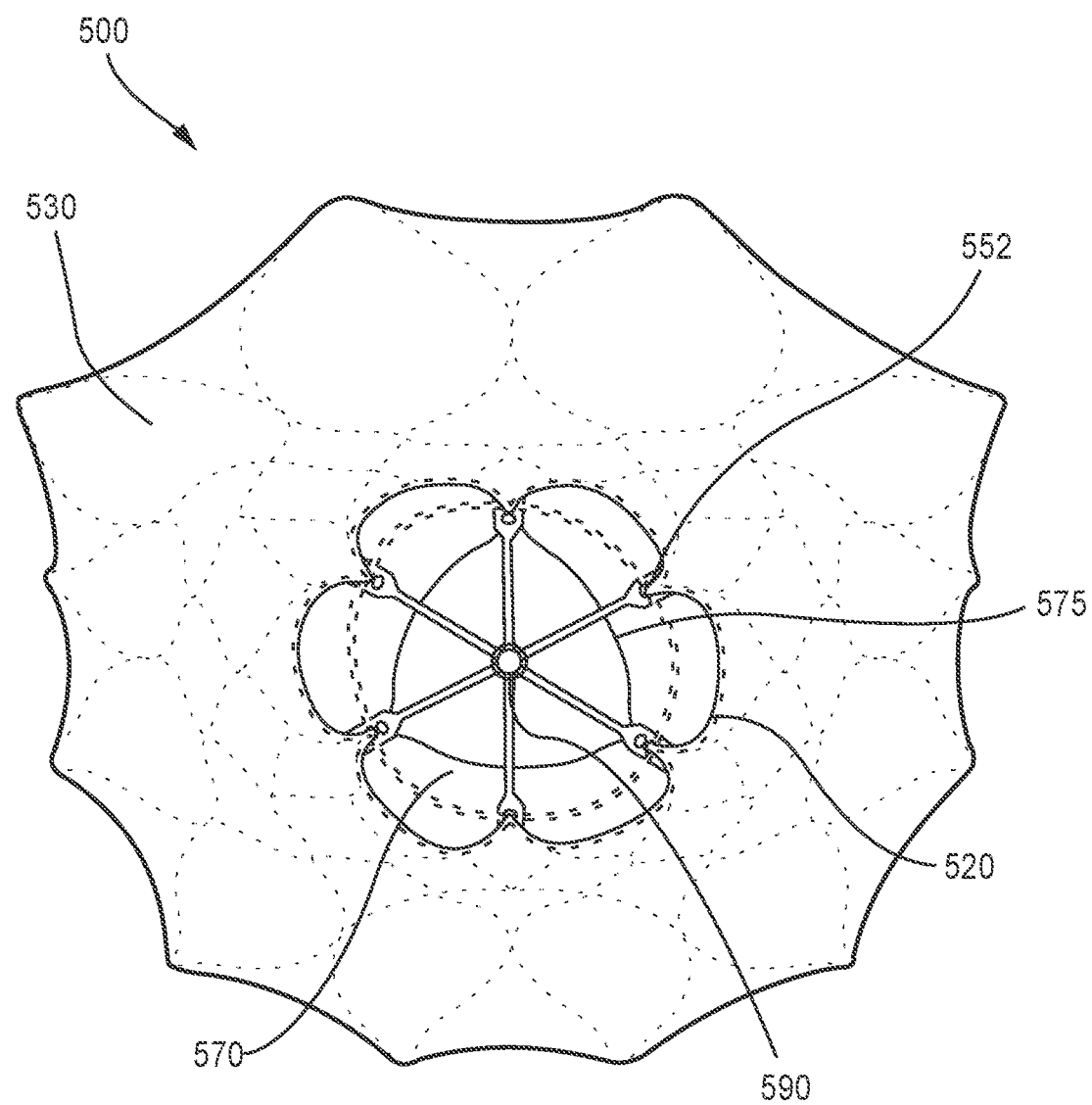
Figure 9:
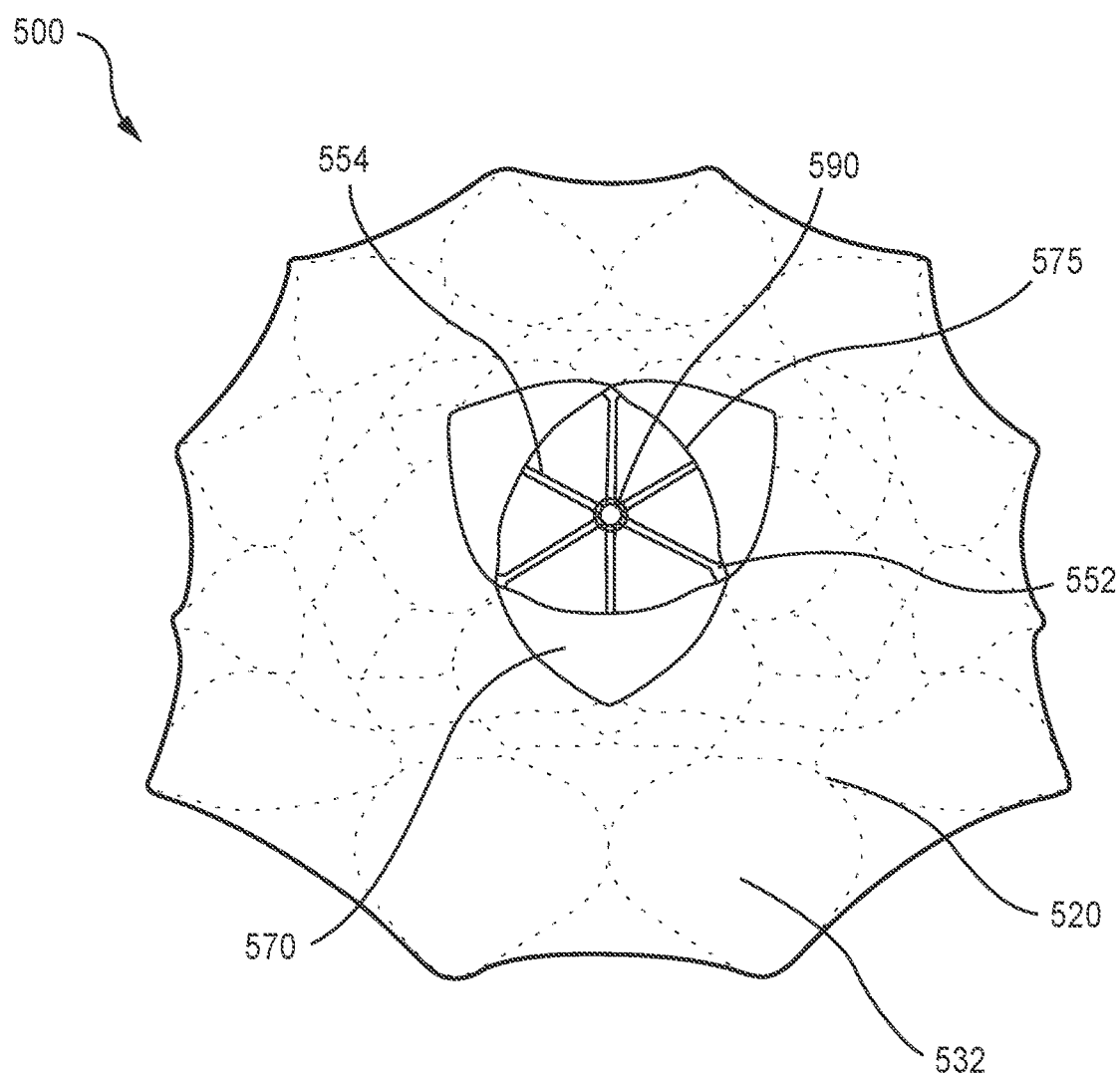

FIGS. 7-9 illustrate an embodiment of a prosthetic heart valve that can be delivered and deployed within a left atrium of a heart using a transfemoral delivery approach as described above. FIGS. 7-9 are front, bottom, and top views, respectively, of a prosthetic heart valve 500 according to an embodiment. Prosthetic heart valve 500 (also referred to herein as "valve") is designed to replace a damaged or diseased native heart valve such as a mitral valve. Valve 500 includes an outer frame assembly 510 and an inner valve assembly 540 coupled to the outer frame assembly 510.

As shown, outer frame assembly 510 includes an outer frame 520, covered on all or a portion of its outer face with an outer covering 530, and covered on all or a portion of its inner face by an inner covering 532. Outer frame 520 can provide several functions for prosthetic heart valve 500, including serving as the primary structure, as an anchoring mechanism and/or an attachment point for a separate anchoring mechanism to anchor the valve to the native heart valve apparatus, a support to carry inner valve assembly 540, and/or a seal to inhibit paravalvular leakage between prosthetic heart valve 500 and the native heart valve apparatus.

Outer frame 520 is configured to be manipulated and/or deformed (e.g., compressed and/or expanded) and, when released, return to its original (undeformed) shape. To achieve this, outer frame 520 can be formed of materials, such as metals or plastics, that have shape memory properties. With regards to metals, Nitinol has been found to be especially useful since it can be processed to be austenitic, martensitic or super elastic. Other shape memory alloys, such as Cu—Zn—Al—Ni alloys, and Cu—Al—Ni alloys, may also be used.

As best shown in FIG. 7, outer frame assembly 510 has an upper end (e.g., at the atrium portion 516), a lower end (e.g., at the ventricle portion 512), and a medial portion (e.g., at the annulus portion 514) therebetween. The medial portion of the outer frame assembly 510 has a perimeter that is configured (e.g., sized, shaped) to fit into an annulus of a native atrioventricular valve. The upper end of the outer frame assembly 510 has a perimeter that is larger than the perimeter of the medial portion. In some embodiments, the perimeter of the upper end of the outer frame assembly 510 has a perimeter that is substantially larger than the perimeter of the medial portion. As shown best in FIG. 9, the upper end and the medial portion of the outer frame assembly 510 has a D-shaped cross-section. In this manner, the outer frame assembly 510 promotes a suitable fit into the annulus of the native atrioventricular valve.

Inner valve assembly 540 includes an inner frame 550, an outer covering 560, and leaflets 570. As shown, the inner valve assembly 540 includes an upper portion having a periphery formed with multiple arches. The inner frame 550 includes six axial posts or frame members that support outer covering 560 and leaflets 570. Leaflets 570 are attached along three of the posts, shown as commissure posts 552 (best illustrated in FIG. 8), and outer covering 560 is attached to the other three posts, 554 (best illustrated in FIG. 8), and optionally to commissure posts 552. Each of outer covering 560 and leaflets 570 are formed of approximately rectangular sheets of material, which are joined together at their upper, or atrium end. The lower, ventricle end of outer covering 560 may be joined to inner covering 532 of outer frame assembly 510, and the lower, ventricle end of leaflets 570 may form free edges 575, though coupled to the lower ends of commissure posts 552.

Although inner valve assembly 540 is shown as having three leaflets, in other embodiments, an inner valve assembly can include any suitable number of leaflets. The leaflets 570 are movable between an open configuration and a closed configuration in which the leaflets 570 coapt, or meet in a sealing abutment.

Outer covering 530 of the outer frame assembly 510 and inner covering 532 of outer frame assembly 510, outer covering 560 of the inner valve assembly 540 and leaflets 570 of the inner valve assembly 540 may be formed of any suitable material, or combination of materials, such as those discussed above. In this embodiment, the inner covering 532 of the outer frame assembly 510, the outer covering 560 of the inner valve assembly 540, and the leaflets 570 of the inner valve assembly 540 are formed, at least in part, of porcine pericardium. Moreover, in this embodiment, the outer covering 530 of the outer frame assembly 510 is formed, at least in part, of polyester.

Figure 10:
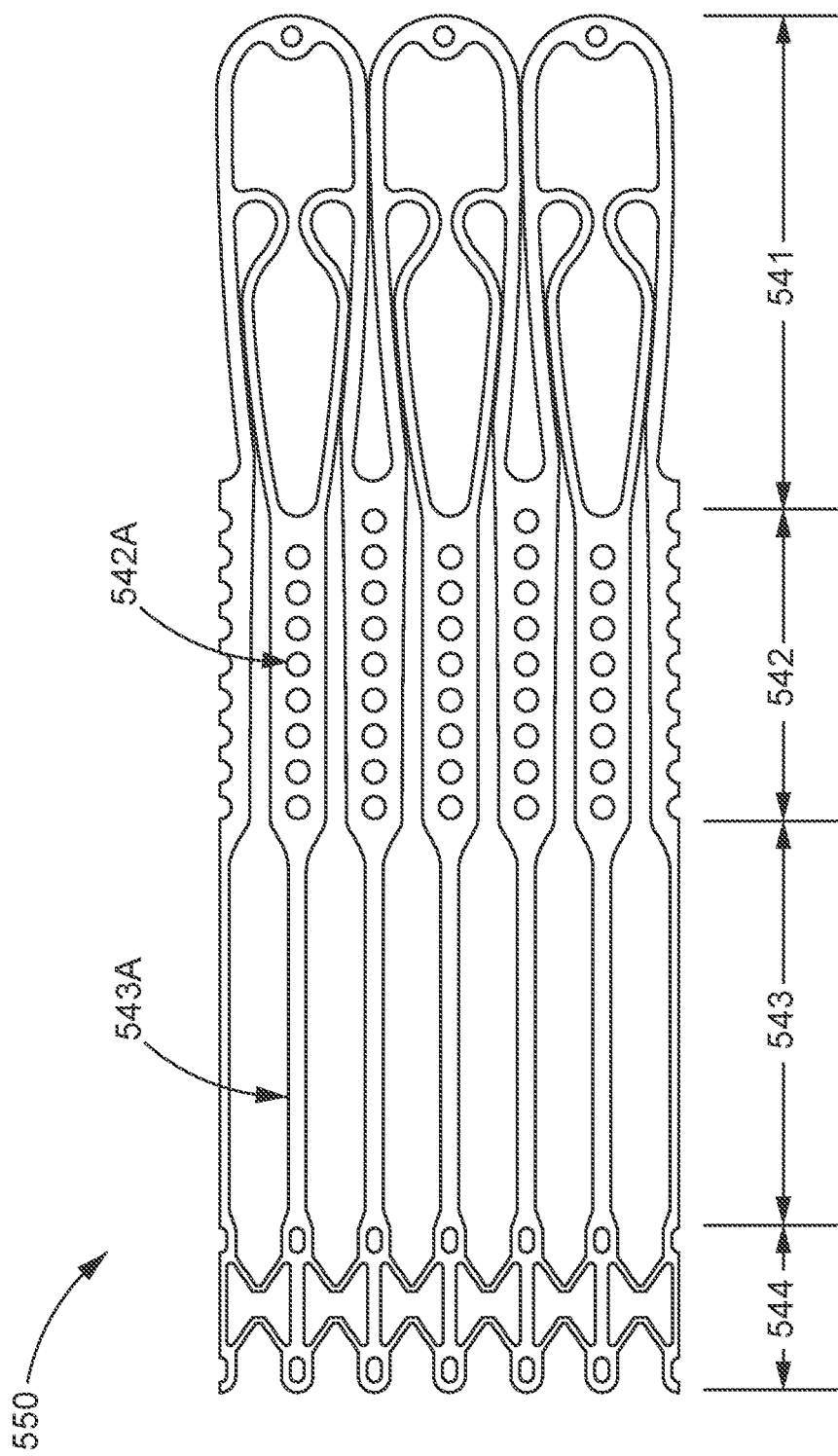
FIG. 10 is an opened and flattened view of the inner frame of the prosthetic heart valve of FIGS. 7-9, in an unexpanded configuration.
Figure 11:
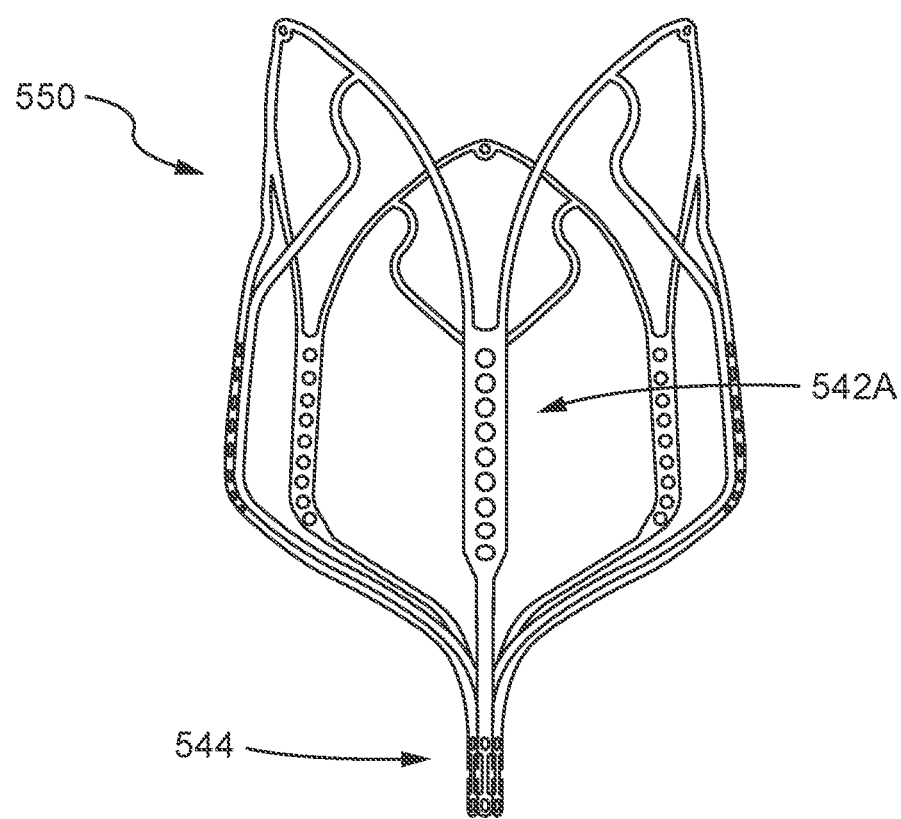
FIGS. 11 and 12 are side and bottom views, respectively, of the inner frame of FIG. 10 in an expanded configuration.
Figure 12:
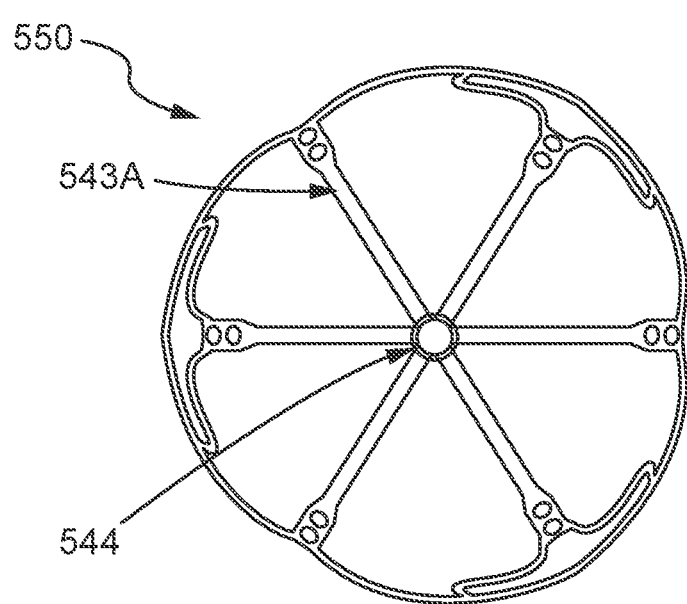

Inner frame 550 is shown in more detail in FIGS. 10-12. Specifically, FIGS. 10-12 show inner frame 550 in an undeformed, initial state (FIG. 10), a side view of the inner frame 550 in a deployed configuration (FIG. 11), and a bottom view of the inner frame 550 in a deployed configuration (FIG. 12), respectively, according to an embodiment.

In this embodiment, inner frame 550 is formed from a laser-cut tube of Nitinol®. Inner frame 550 is illustrated in FIG. 10 in an undeformed, initial state, i.e. as laser-cut, but cut and unrolled into a flat sheet for ease of illustration. Inner frame 550 can be divided into four portions, corresponding to functionally different portions of the inner frame 550 in final form: atrial portion 541, body portion 542, strut portion 543, and tether clamp or connecting portion 544. Strut portion 543 includes six struts, such as strut 543A, which connect body portion 542 to tether clamp portion 544.

Connecting portion 544 includes longitudinal extensions of the struts, connected circumferentially by pairs of opposed, slightly V-shaped connecting members (or "micro-Vs"). Connecting portion 544 is configured to be radially collapsed by application of a compressive force, which causes the micro-Vs to become more deeply V-shaped, with the vertices moving closer together longitudinally and the open ends of the V shapes moving closer together circumferentially. Thus, connecting portion 544 can be configured to compressively clamp or grip one end of a tether, either connecting directly onto a tether line (e.g. braided filament line) or onto an intermediate structure, such as a polymer or metal piece that is in turn firmly fixed to the tether line.

In contrast to connecting portion 544, atrial portion 541 and body portion 542 are configured to be expanded radially. Strut portion 543 forms a longitudinal connection, and radial transition, between the expanded body portion and the compressed connecting portion 544.

Body portion 542 includes six longitudinal posts, such as post 542A. The posts can be used to attach leaflets 570 to inner frame 540, and/or can be used to attach inner assembly 540 to outer assembly 510, such as by connecting inner frame 550 to outer frame 520. In the illustrated embodiment, the posts include openings through which connecting members (such as suture filaments and/or wires) can be passed to couple the posts to other structures.

Inner frame 550 is shown in a fully deformed, i.e. the final, deployed configuration, in side view and bottom view in FIGS. 11 and 12, respectively.

Figure 13:
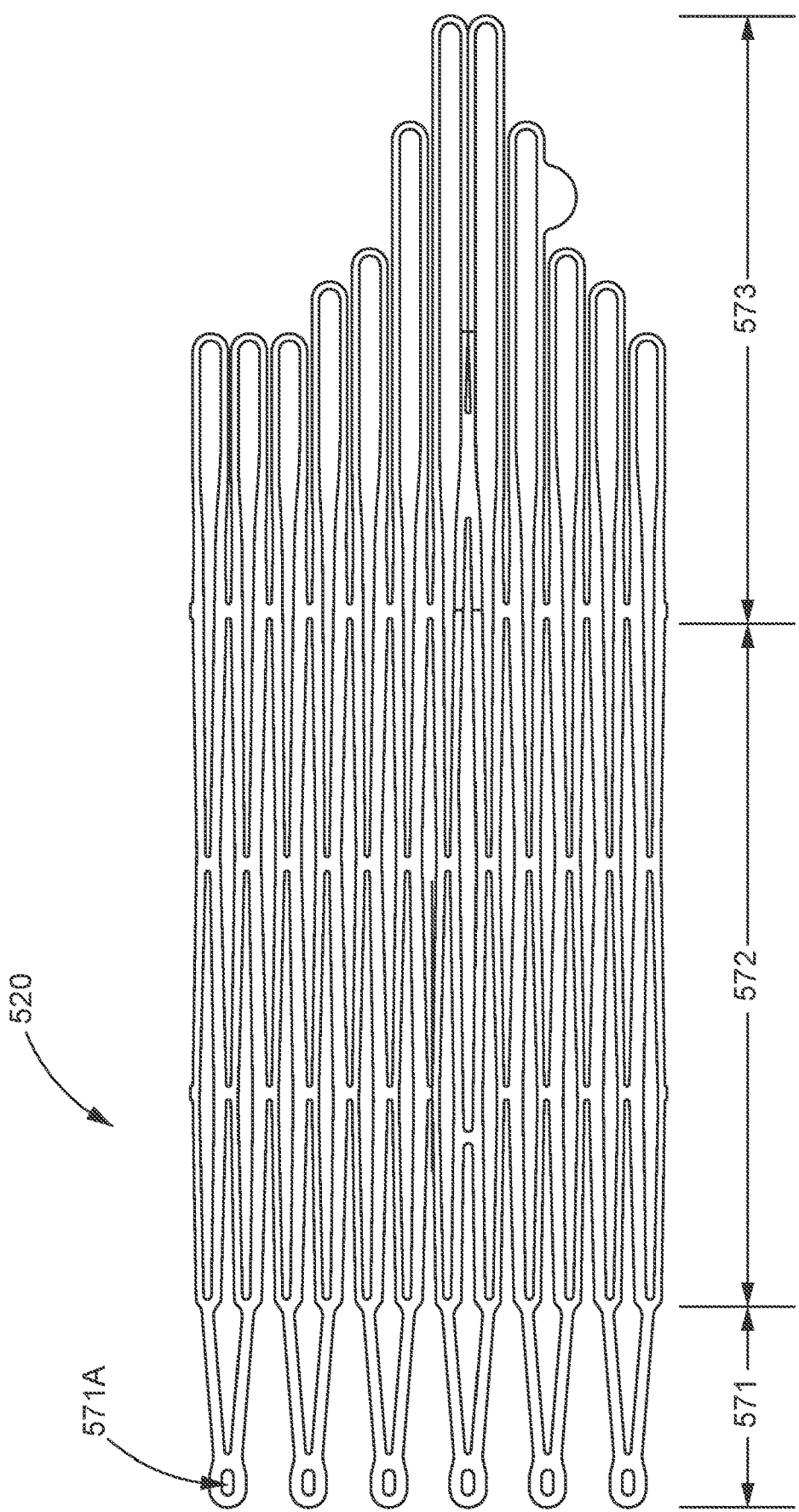
FIG. 13 is an opened and flattened view of the outer frame of the valve of FIGS. 7-9, in an unexpanded configuration.
Figure 14:
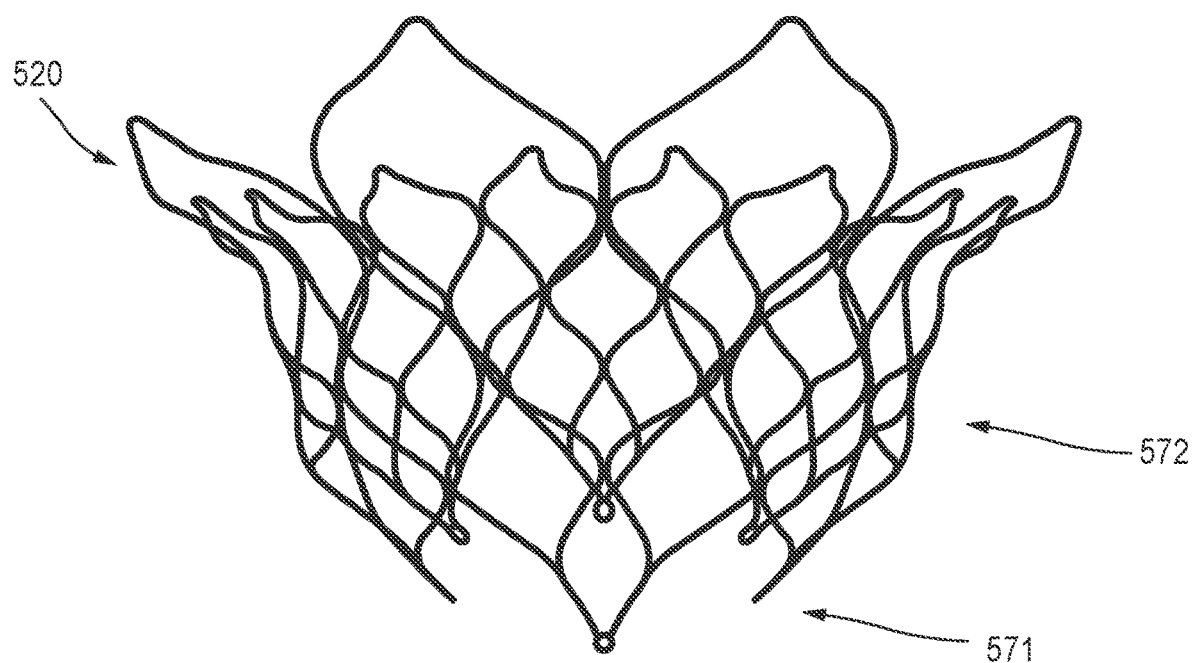
FIGS. 14 and 15 are side and top views, respectively, of the outer frame of FIG. 13 in an expanded configuration.
Figure 15:
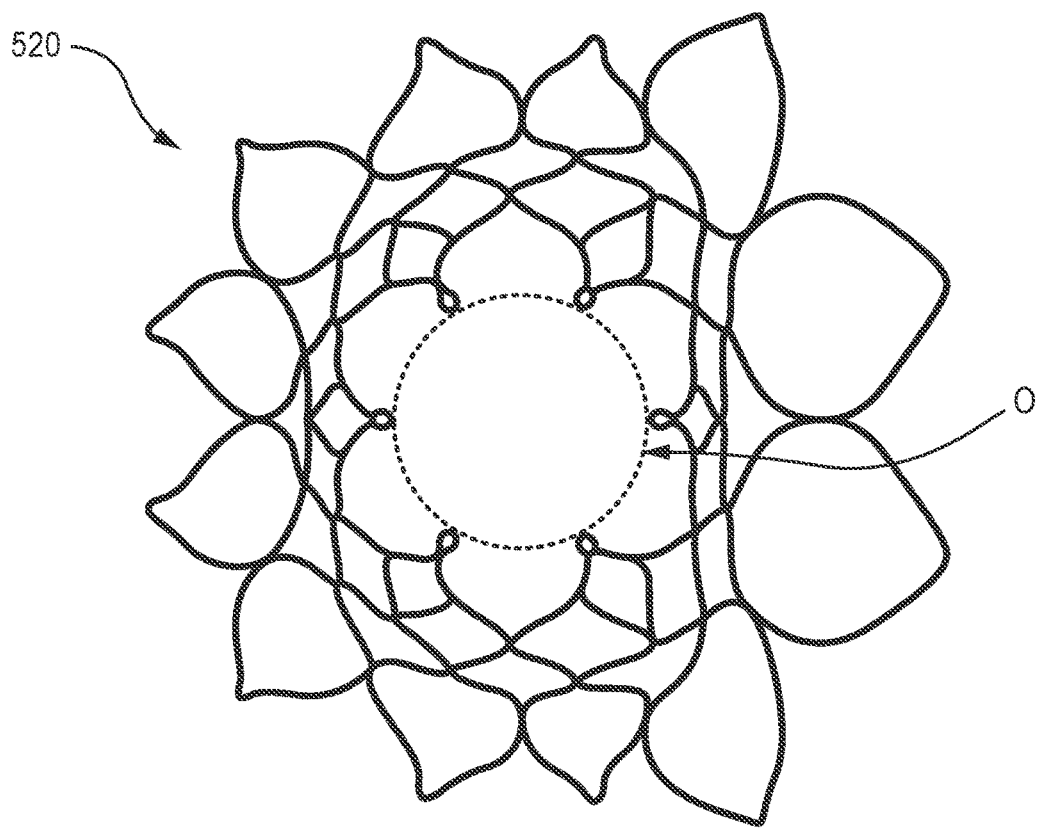

Outer frame 520 of valve 500 is shown in more detail in FIGS. 13-15. In this embodiment, outer frame 520 is also formed from a laser-cut tube of Nitinol®. Outer frame 520 is illustrated in FIG. 13 in an undeformed, initial state, i.e. as laser-cut, but cut and unrolled into a flat sheet for ease of illustration. Outer frame 520 can be divided into a coupling portion 571, a body portion 572, and a cuff portion 573, as shown in FIG. 13. Coupling portion 571 includes multiple openings or apertures, such as 571A, by which outer frame 520 can be coupled to inner frame 550, as discussed in more detail below.

Outer frame 520 is shown in a fully deformed, i.e. the final, deployed configuration, in side view and top view in FIGS. 14 and 15, respectively. As best seen in FIG. 15, the lower end of coupling portion 571 forms a roughly circular opening (identified by "0" in FIG. 15). The diameter of this opening preferably corresponds approximately to the diameter of body portion 542 of inner frame 550, to facilitate coupling of the two components of valve 500.

Figure 16:
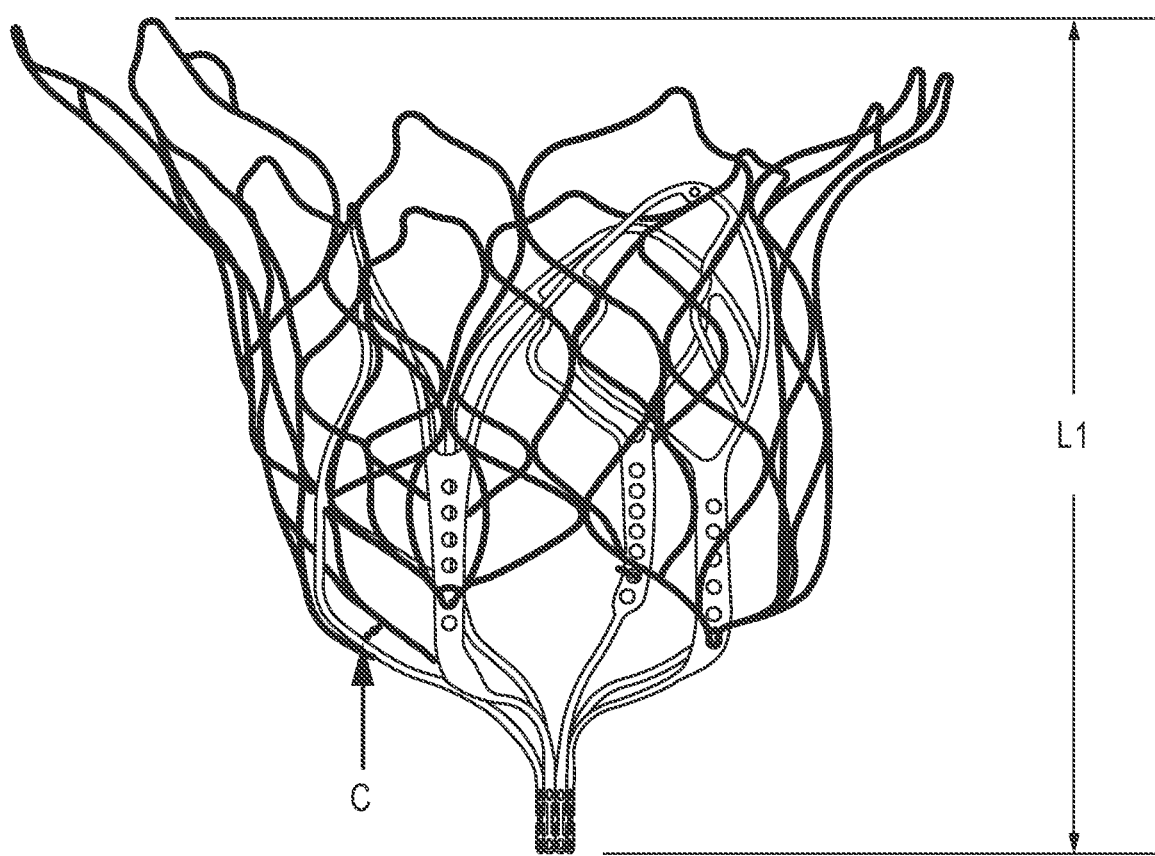
FIGS. 16-18 are side, front, and top views of an assembly of the inner frame of FIGS. 10-12 and the outer frame of FIGS. 13-15.
Figure 17:
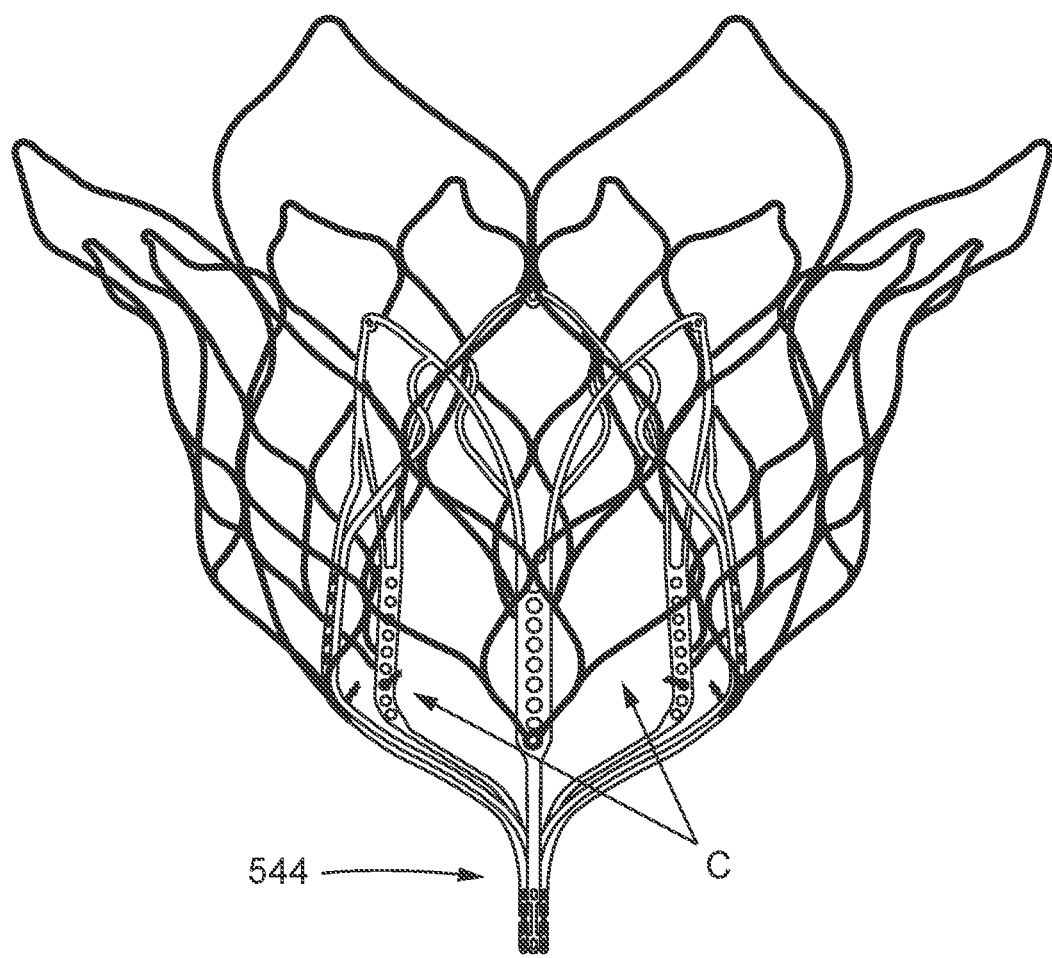
Figure 18:
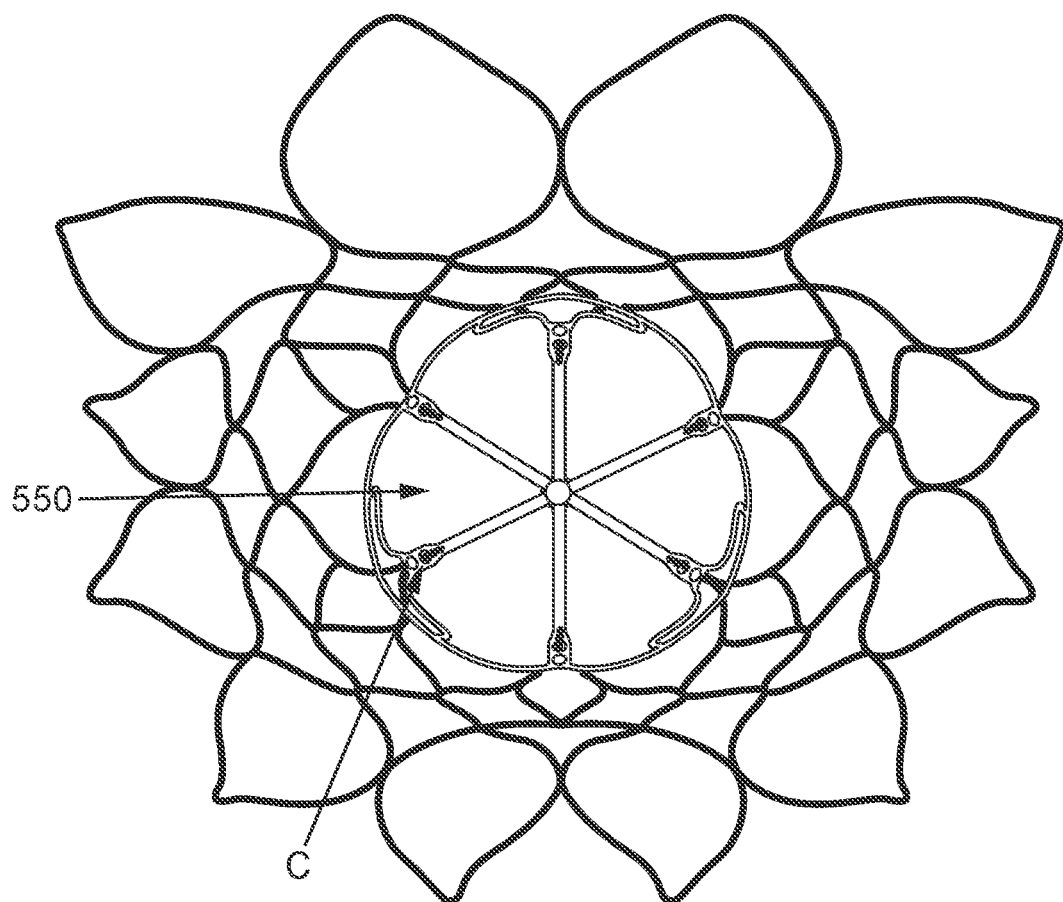

Outer frame 520 and inner frame 550 are shown coupled together in FIGS. 16-18, in front, side, and top views, respectively. The two frames collectively form a structural support for a prosthetic valve such as valve 500. The frames support the valve leaflet structure (e.g., leaflets 570) in the desired relationship to the native valve annulus, support the coverings (e.g., outer covering 530, inner covering 532, outer covering 560) for the two frames to provide a barrier to blood leakage between the atrium and ventricle, and couple to the tether (e.g., tether assembly 590) (by the inner frame 550) to aid in holding the prosthetic valve in place in the native valve annulus by the tether connection to the ventricle wall. The outer frame 520 and the inner frame 550 are connected at six coupling points (representative points are identified as "C"). In this embodiment, the coupling points are implemented with a mechanical fastener, such as a short length of wire, passed through an aperture (such as aperture 571A) in coupling portion 571 of outer frame 520 and corresponding openings in longitudinal posts (such as post 542A) in body portion 542 of inner frame 550. Inner frame 550 is thus disposed within the outer frame 520 and securely coupled to it.

FIGS. 19-25 illustrate a method of reconfiguring a prosthetic heart valve 300 (e.g., prosthetic mitral valve) prior to inserting the prosthetic heart valve 300 into a delivery sheath 326 (see, e.g., FIGS. 21-25) for delivery into the heart via the femoral vein. The prosthetic heart valve 300 (also referred to herein as "valve") can be constructed the same as or similar to, and function the same as or similar to the valve 500 described above. Thus, some details regarding the valve 300 are not described below. It should be understood that for features and functions not specifically discussed, those features and functions can be the same as or similar to the valve 500.

Figure 19:
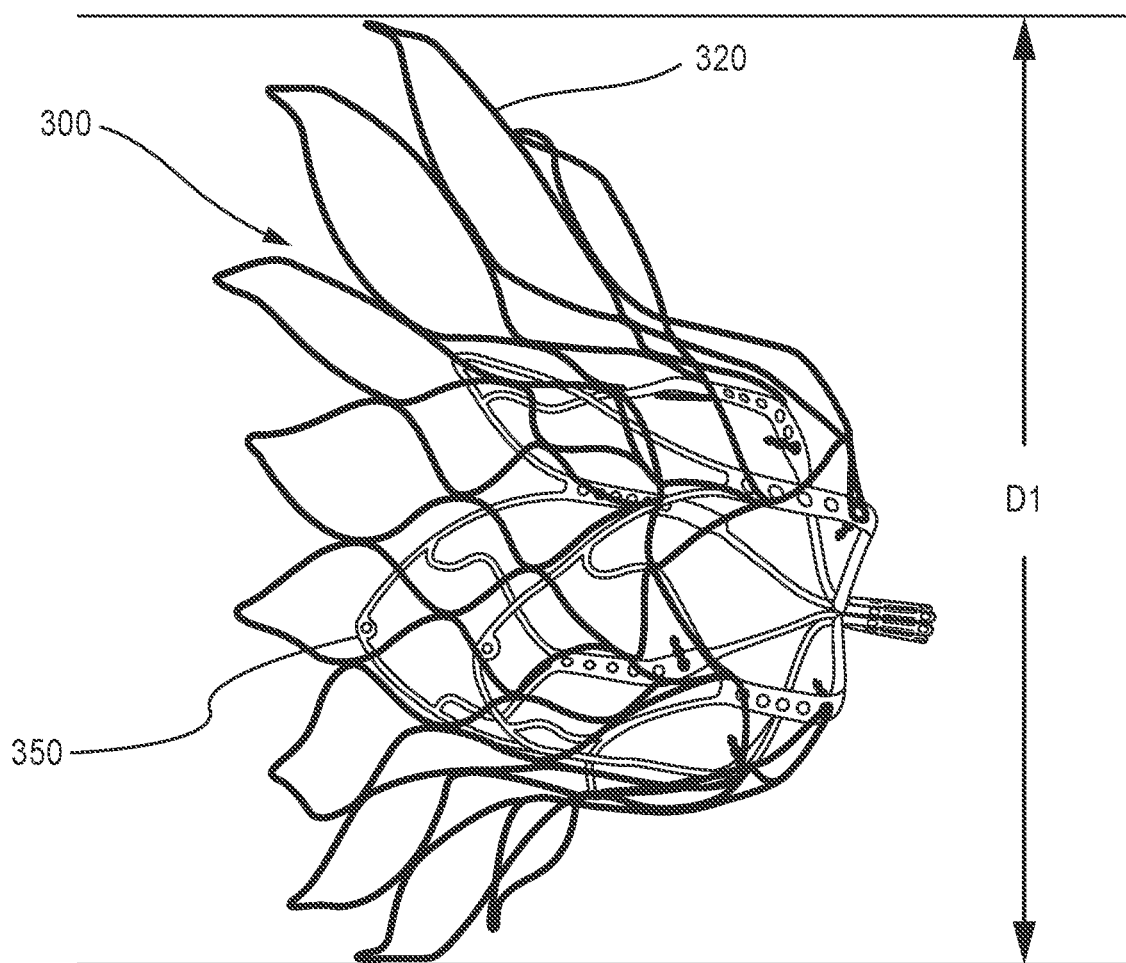
FIG. 19 is a side perspective view of the assembly of the inner frame of FIGS. 10-12 and the outer frame of FIGS. 13-15 shown in a biased expanded configuration.
Figure 20:
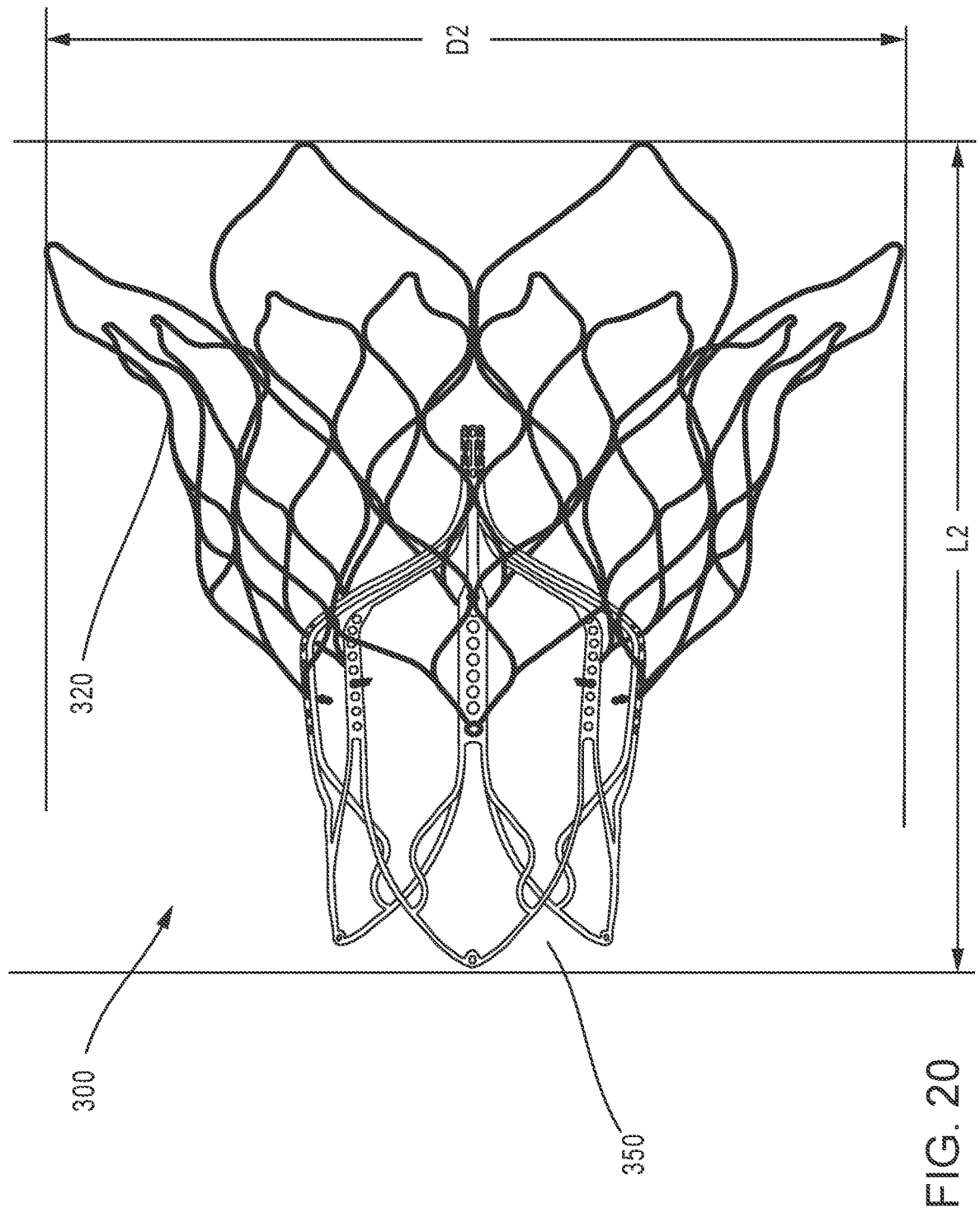
FIG. 20 is a side perspective view of the assembly of FIG. 19 with the outer frame shown inverted.
Figure 21:
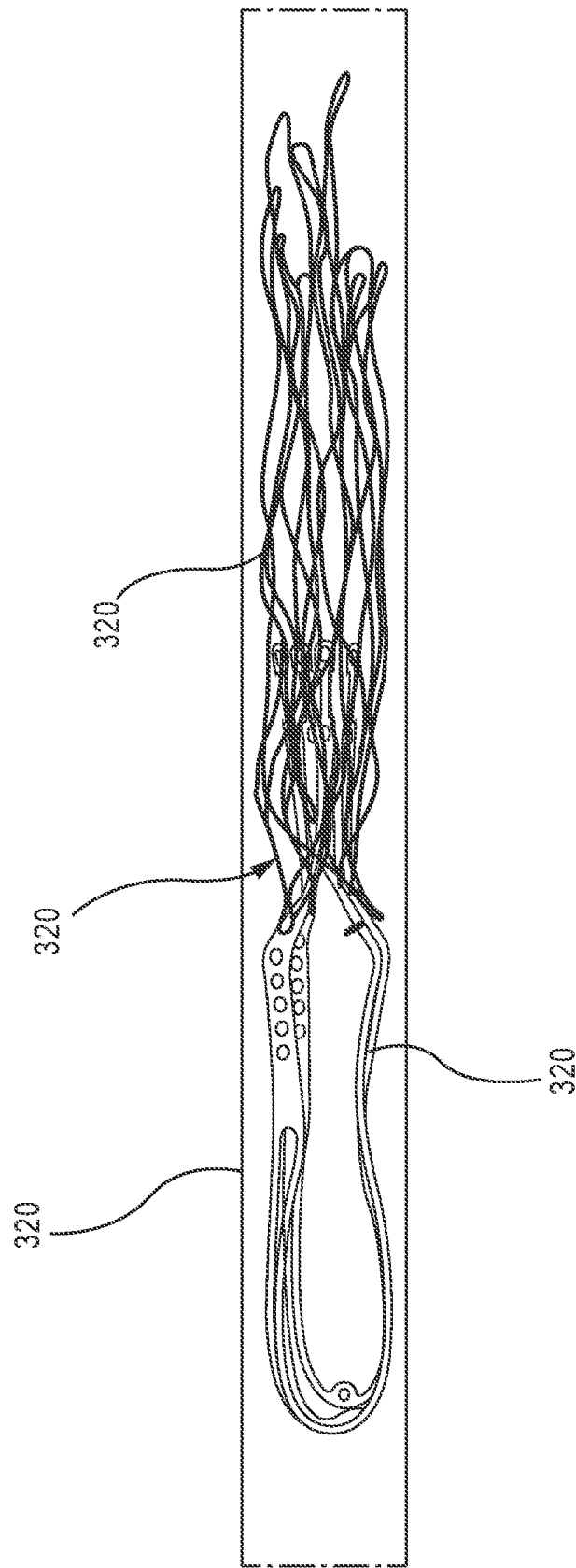
FIG. 21 is a side view of the assembly of FIG. 20 shown in a collapsed configuration within a lumen of a delivery sheath.

As shown in FIG. 19, the valve 300 has an outer frame 320 and an inner frame 350. As discussed above for valves 200 and 500, the outer frame 320 and the inner frame 350 of valve 300 can each be formed with a shape-memory material and have a biased expanded or deployed configuration. The outer frame 320 and the inner frame 350 can be moved to a collapsed or undeployed configuration for delivery of the valve 300 to the heart. In this example method of preparing the valve 300 for delivery to the heart, the outer frame 320 of the valve 300 is first disposed in a prolapsed or inverted configuration as shown in FIG. 20. Specifically, the elastic or superelastic structure of outer frame 320 of valve 300 allows the outer frame 320 to be disposed in the prolapsed or inverted configuration prior to the valve 300 being inserted into the lumen of the delivery sheath 326. As shown in FIG. 20, to dispose the outer frame 320 in the inverted configuration, the outer frame 320 is folded or inverted distally such that the outer frame 320 is pointed away from the inner frame 350. In this inverted configuration, the overall outer perimeter or outer diameter of the valve 300 is reduced and the overall length is increased. For example, the diameter D1 shown in FIG. 19 is greater than the diameter D2 shown in FIG. 20, and the length L1 in FIG. 16 is less than the length L2 in FIG. 20. With the outer frame 320 in the inverted configuration, the valve 300 can be placed within a lumen of a delivery sheath 326 as shown in FIG. 21 for delivery of the valve 300 to the left atrium of the heart. By disposing the outer frame 320 in the inverted configuration, the valve 300 can be collapsed into a smaller overall diameter, i.e. placed in a smaller diameter delivery sheath, than would be possible if the valve 300 in the configuration shown in FIG. 19 were collapsed radially. This is because in the configuration shown in FIG. 19, the two frames are concentric, and thus the outer frame 320 must be collapsed around the inner frame 350, whereas in the configuration shown in FIG. 20, the two frames are coaxial but not concentric, such that the outer frame 320 can be collapsed without needing to accommodate the inner frame 350 inside it.

The procedure to deliver the valve 300 to the heart can be the same as or similar to the procedure described with reference to FIGS. 1-6. In this embodiment, the valve 300 is not partially deployed outside of the lumen of the delivery sheath 326 prior to being inserted into a femoral puncture, through the femoral vein, through the inferior vena cava, into the right atrium, through the septum Sp and into the left atrium LA of the heart. With the distal end portion of the delivery sheath 326 disposed within the left atrium of the heart, the valve 300 can be deployed outside of the delivery sheath 326. For example, although not shown, a tether such as tether 236 described above for valve 200 can be attached to the valve 300 and used to pull the valve 300 out of the lumen of the delivery sheath 326. Alternatively, or in addition to, a pusher device (not shown) can be used to deploy the valve 300. Thus, as described above for valve 200, the valve 300 can be deployed by pushing with the pusher device, pulling with the tether, or both.

Figure 22:
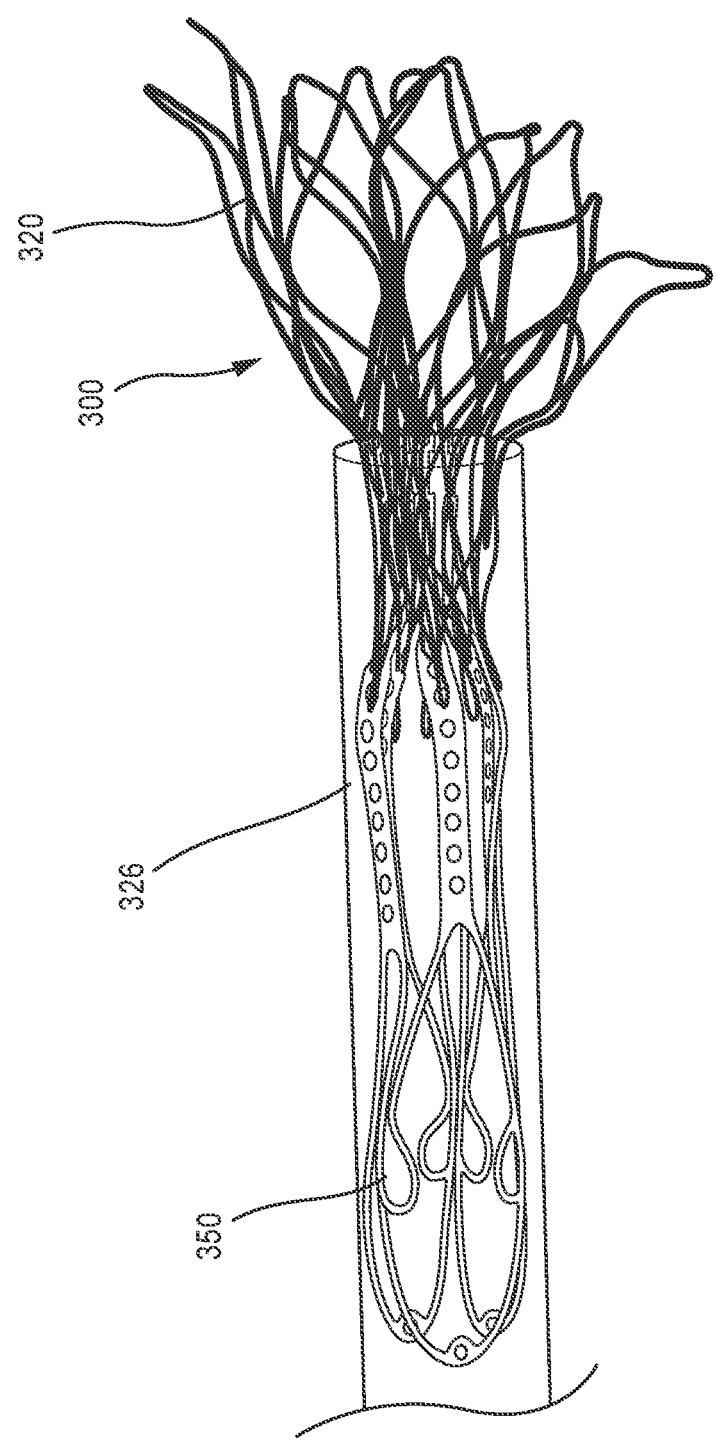
FIG. 22 is a side view of the assembly of FIG. 21 shown in a first partially deployed configuration.
Figure 23:
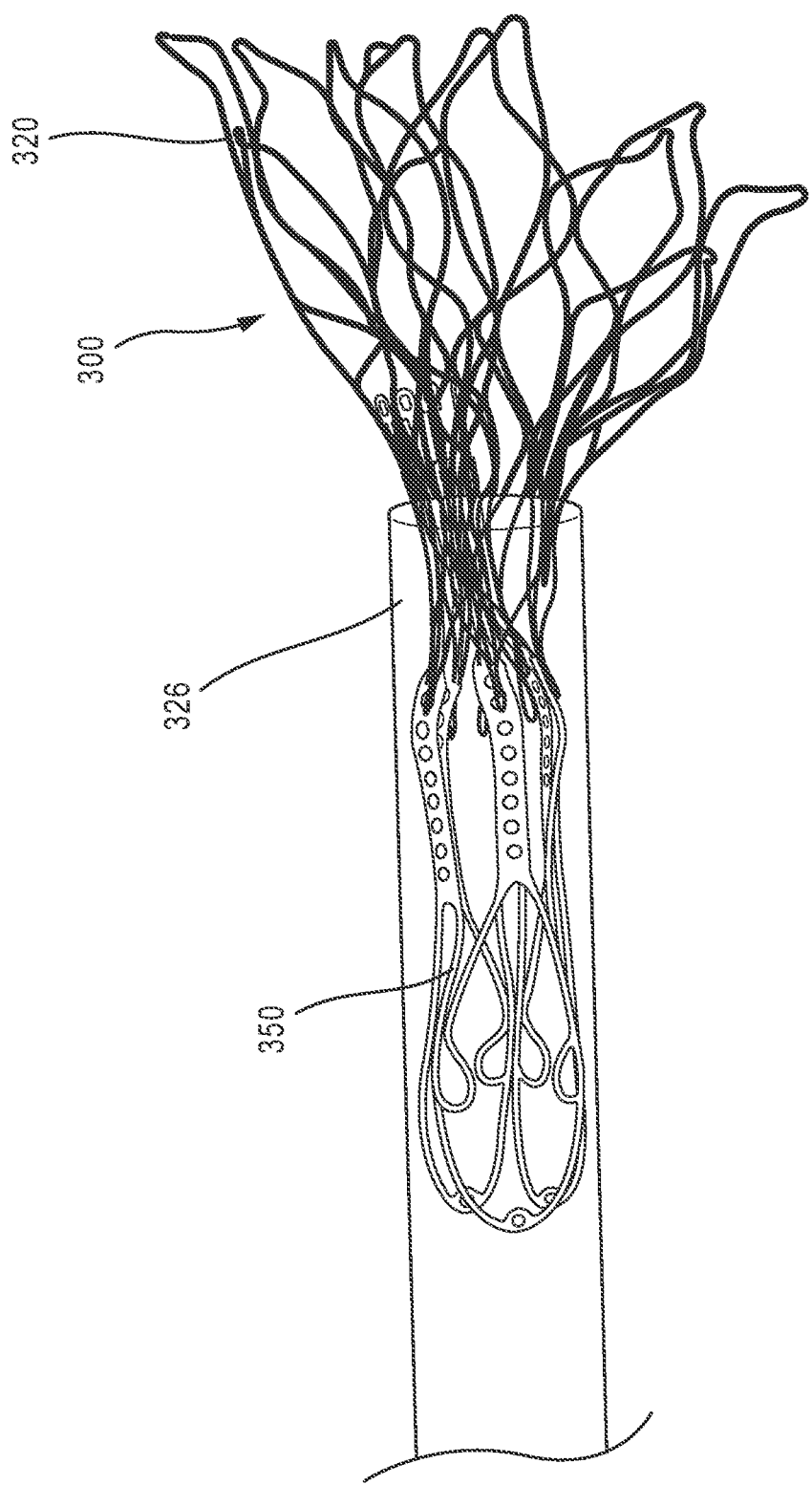
FIG. 23 is a side view of the assembly of FIG. 21 shown in a second partially deployed configuration.
Figure 24:
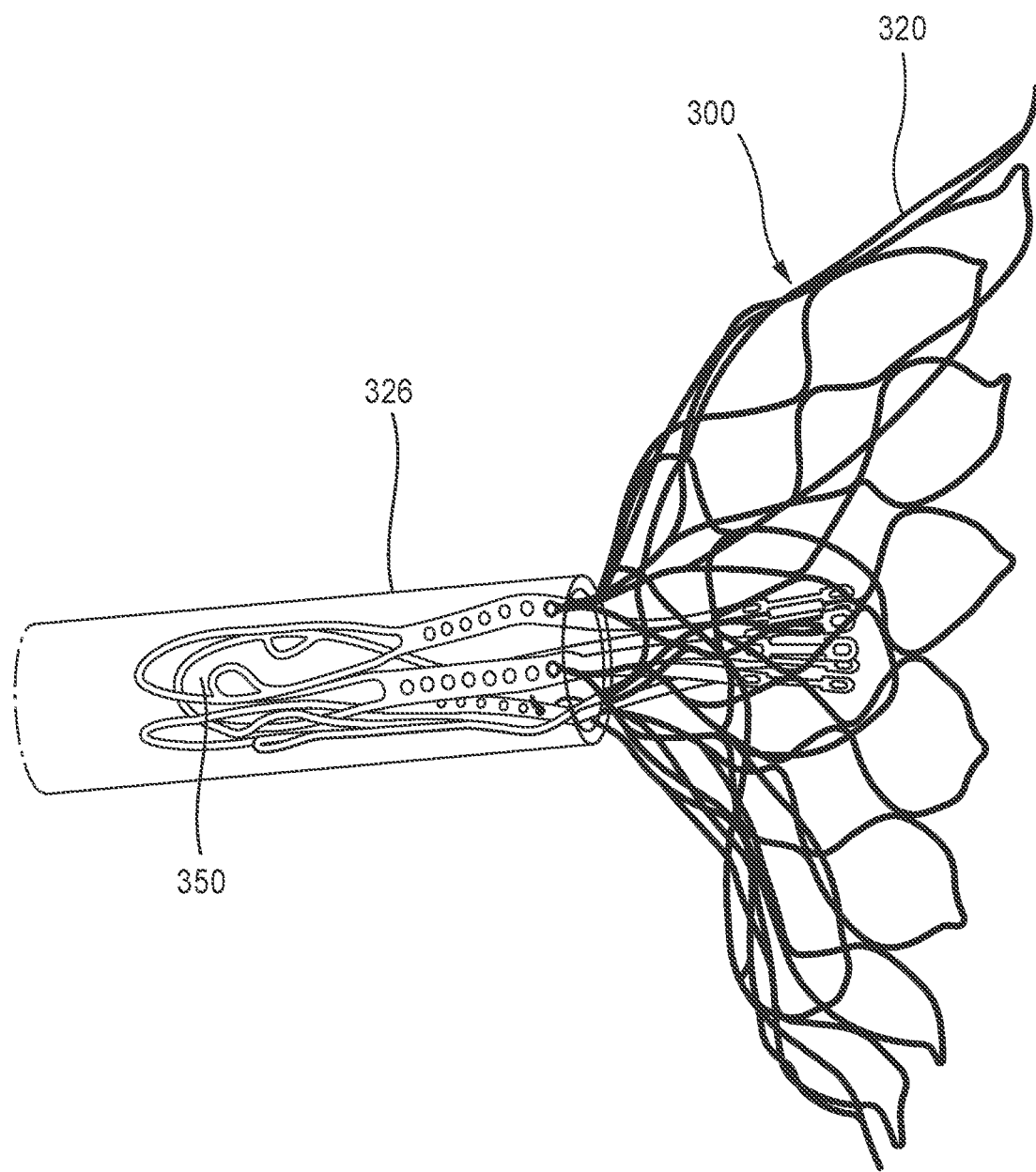
FIG. 24 is a side view of the assembly of FIG. 21 shown in a third partially deployed configuration in which the inverted outer frame is substantially deployed outside of the delivery sheath.
Figure 25:
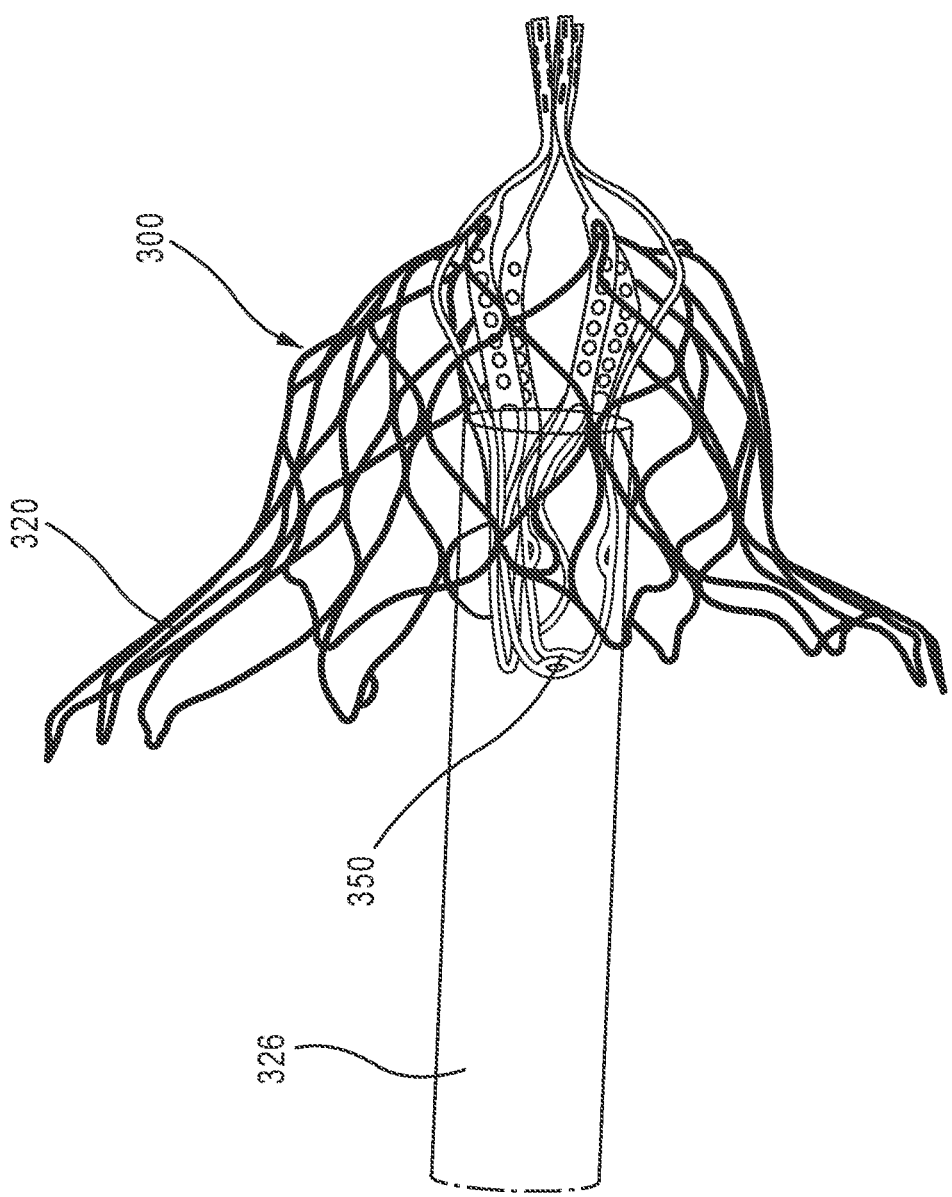
FIG. 25 is a side view of the assembly of FIG. 21 shown in a fourth partially deployed configuration in which the outer frame has reverted and assumed a biased expanded configuration.

As the valve 300 exits the lumen of the delivery sheath 326, the outer frame assembly 310 exits first in its inverted configuration as shown in the progression of FIGS. 22-24. After the outer frame assembly 310 is fully outside of the lumen of the delivery sheath 326, the outer frame 320 can revert to its expanded or deployed configuration as shown in FIG. 25. In some embodiments, the pusher device and/or the tether can be used to aid in the reversion of the outer frame assembly 310. The valve 300 can continue to be deployed until the inner frame 350 is fully deployed with the left atrium and the valve 300 is in the expanded or deployed configuration (as shown in FIG. 19).

Figure 27:
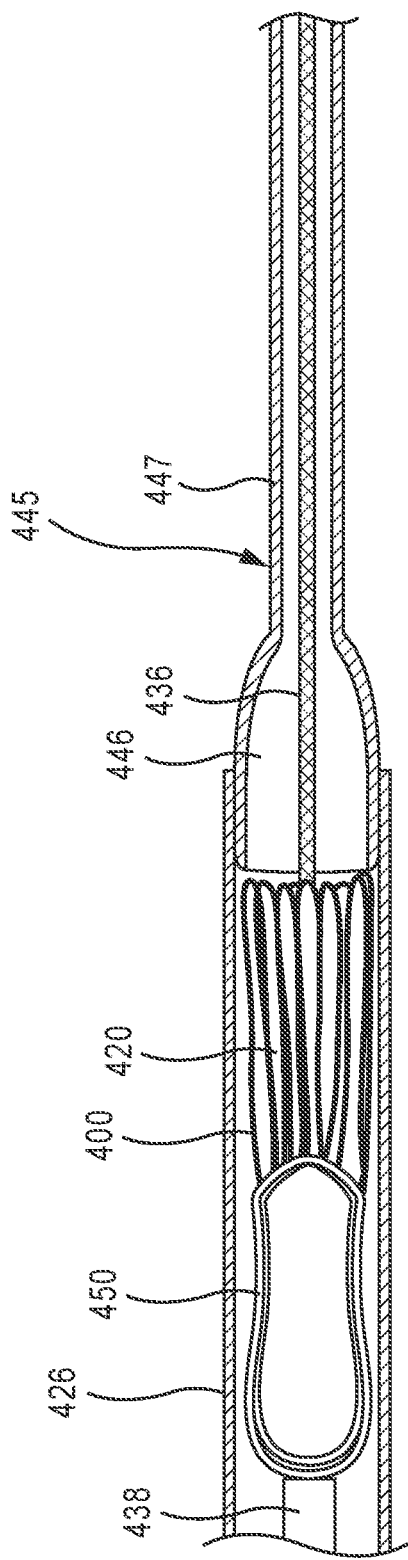
FIG. 27 is a side view of a prosthetic mitral valve in a collapsed configuration within a lumen of a portion of a delivery sheath and a balloon dilator device coupled to the delivery sheath.
Figure 28:
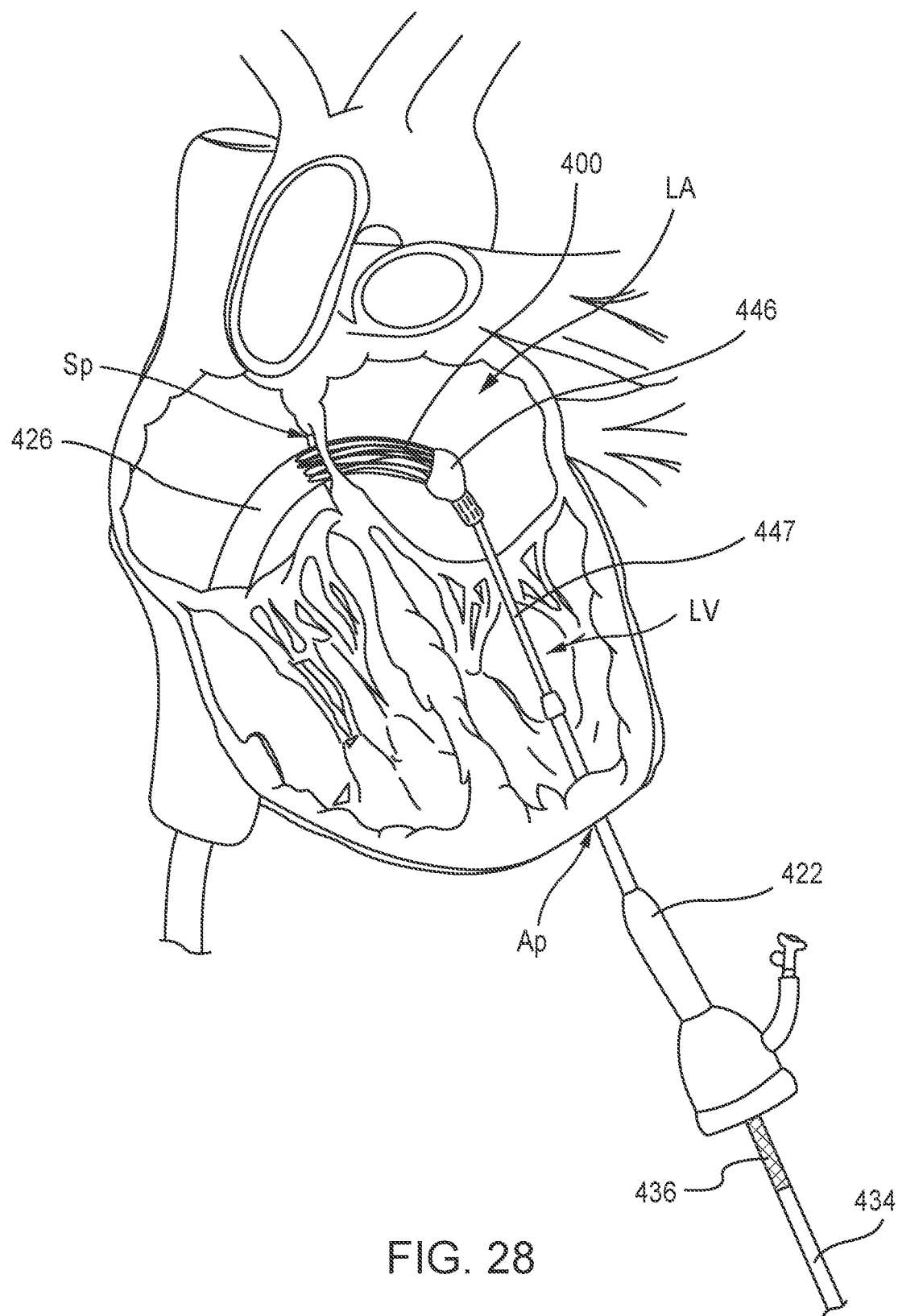
FIG. 28 is a cross-sectional illustration of a heart with the delivery sheath and balloon dilator device of FIG. 27 at a stage of a procedure to deliver and deploy the prosthetic mitral valve disposed within the delivery sheath.

FIGS. 27 and 28 illustrate an optional balloon dilator device that can be used during a procedure for transfemoral delivery of a prosthetic heart valve to the heart. FIG. 27 illustrates a valve 400 disposed within a lumen of a delivery sheath 426. The valve 400 can be constructed the same as or similar to, and function the same as or similar to, the valves 200, 500 and 300 described above. For example, the valve 400 can include an outer frame 420 and an inner frame 450 as described above for previous embodiments. A tether 436 can be coupled to the valve 400 and a valve leader member 434 (see FIG. 28) can be coupled to the tether 436.

In this embodiment, to deliver the valve 400, a leader tube (not shown) can be inserted through an apical puncture and extended through the heart and out through a femoral vein access site. A valve leader member 434 coupled to a tether 436 can be inserted through the femoral end of the leader tube and extended out the apical end of the leader tube, as described above with respect to FIGS. 1-6. The valve 400 can be loaded into the distal end of a lumen of a delivery sheath 426 either before or after the tether 436 and valve leader member 434 are looped through the patient. A balloon dilator device 445 can then be advanced along the valve leader member 434 from the apical end, through the heart, through the femoral vein and out the femoral access site.

The balloon dilator device 445 includes a balloon member 446 that can be disposed at least partially within the distal end portion of the lumen of the delivery device 426, and distal of the valve 400, as shown in FIG. 27. The balloon dilator device 445 also includes an elongate member 447 coupled to the balloon member 446 and that defines an inflation lumen in fluid communication with an interior of the balloon member 446. The elongate member 447 can be coupled to a source of an inflation medium (not shown) configured to supply the inflation medium to the balloon member 446. With the balloon dilator device 445 coupled to the delivery sheath 426 as shown in FIG. 27, the balloon member 446 can be inflated. The delivery sheath 426 can then be inserted through the femoral access site and advanced through the femoral vein, through the inferior vena cava, into the right atrium, through the septum Sp and into the left atrium LA as shown in FIG. 28. The balloon member 446 provides a smooth surface to aid in maneuvering the delivery sheath 426 through the femoral vein and the septum and into the heart. With the distal end portion of the delivery sheath 426 disposed within the left atrium LA, the balloon member 446 can be deflated and removed through the apical access site. The valve 400 can then be deployed and positioned within the mitral annulus as described above for FIGS. 1-6. For example, a pusher device 438 (see FIG. 27) can be used to push the valve 400 out of the lumen of the delivery sheath 426 and/or the tether 436 coupled to the valve 400 can be pulled.

Figure 29:
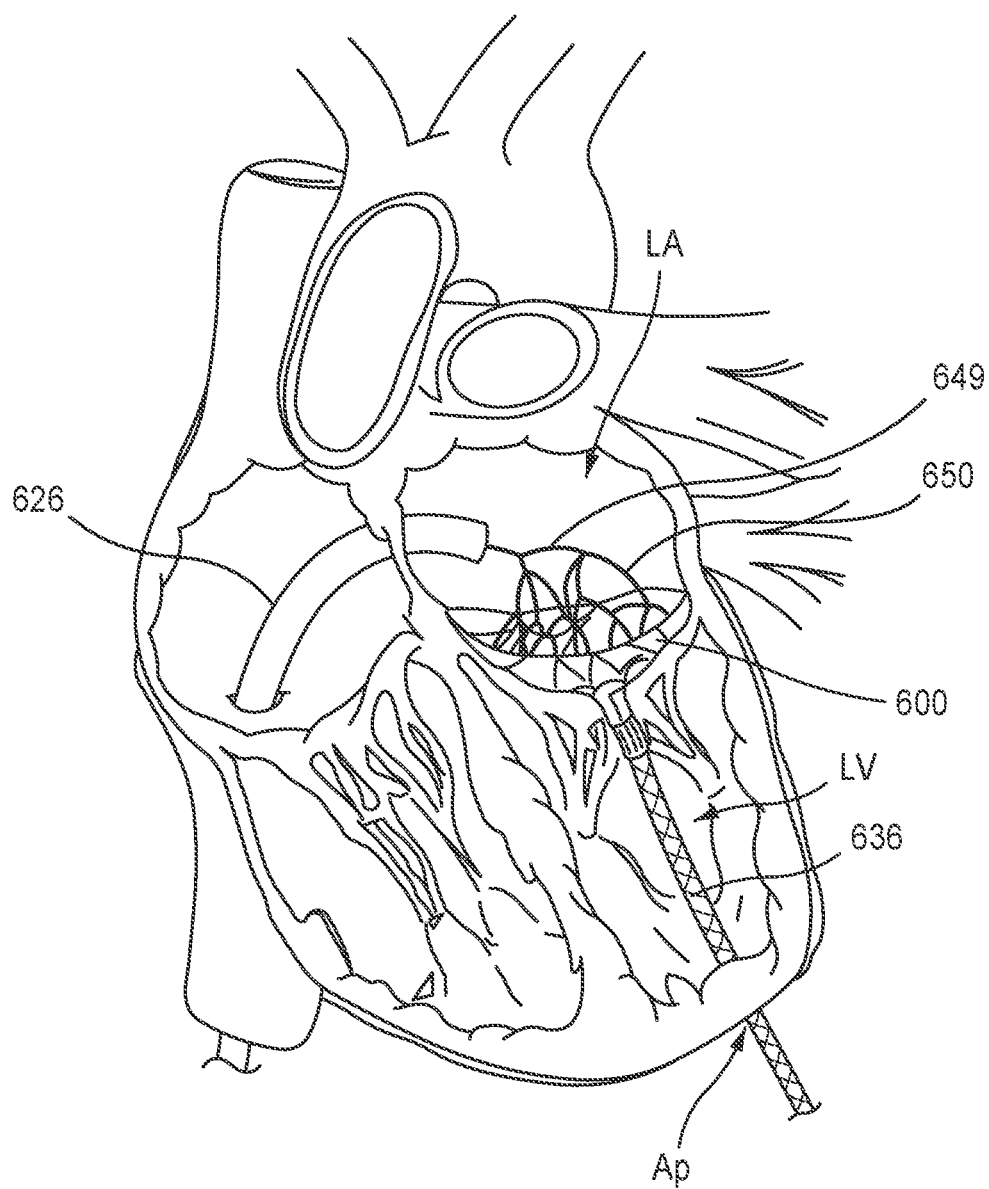
FIG. 29 is a cross-sectional illustration of a heart with a portion of a delivery sheath shown after deploying a prosthetic mitral valve with the assistance of a wire assist structure, according to an embodiment.
Figure 30:
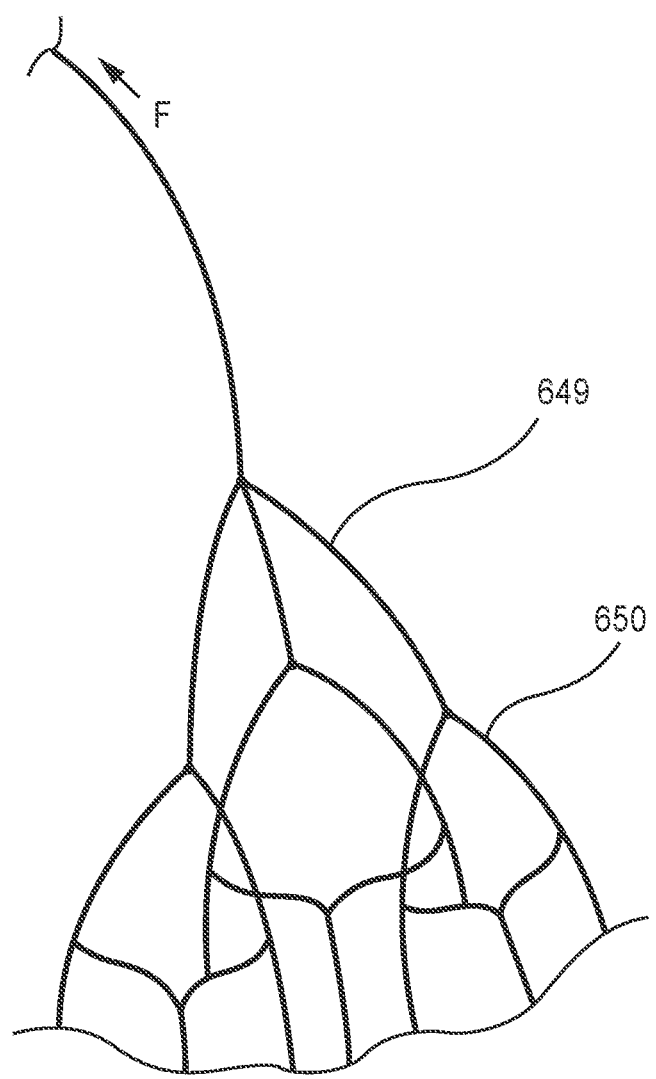
FIG. 30 is a perspective view of the wire assist structure of FIG. 29 coupled to a portion of a prosthetic mitral valve, according to an embodiment.

FIGS. 29 and 30 illustrate an optional wire assist structure that can be used during a procedure to deliver a prosthetic heart valve transfemorally as described above for previous embodiments. A wire assist structure 649 can be releasably coupled to a valve 600 as shown in FIG. 29. The valve 600 can be constructed the same as or similar to, and function the same as or similar to, the valves described above for previous embodiments. For example, the valve 600 can include an outer frame 620 and an inner frame 650. The wire assist structure 649 can be releasably coupled to the inner frame 650 as best shown in FIG. 30. For example, releasable connectors (not shown) can be used to couple the wire assist structure 649 to the inner frame 650.

In use, the wire assist structure 649 can be movably disposed within a delivery sheath 626 used to deliver the valve 600 to the heart. The wire assist structure 649 can hold the inner frame 650 and allow for positioning control of the valve 600 (i.e., clocking and advancement) while the outer frame 650 of the valve 600 is fully expanded, which allows the valve 600 to be functioning during the positioning phase. When the valve 600 is in the desired final position, the wire assist structure 649 can be released from the inner frame 650 and removed with the delivery sheath 626.

Figure 31:
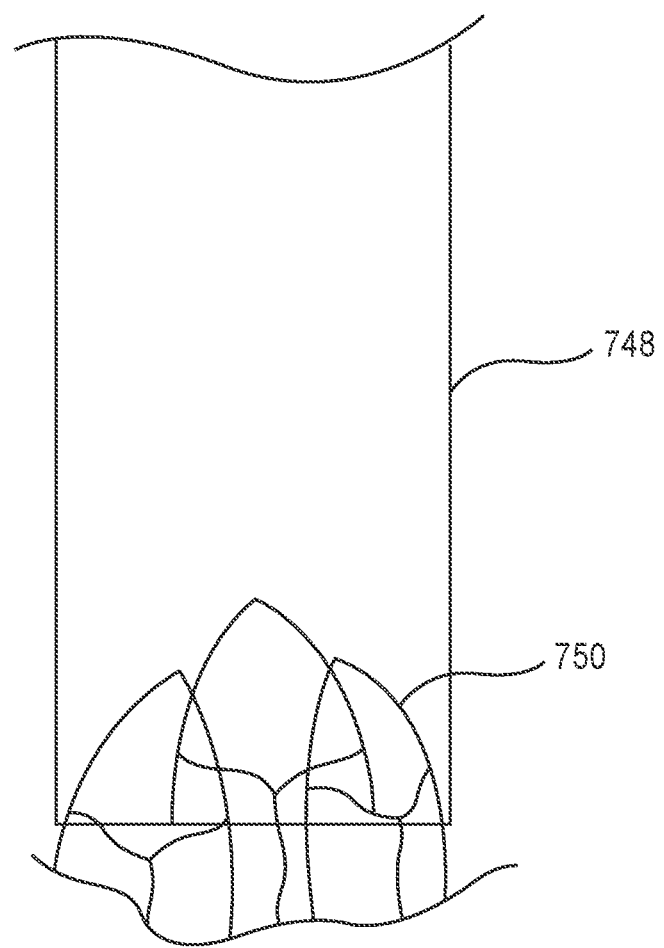
FIG. 31 is a perspective view of an assist member coupled to a portion of a prosthetic mitral valve, according to an embodiment.

FIG. 31 illustrates another optional assist member that can be used during a procedure to deliver a prosthetic heart valve transfemorally. An assist member 748 can be in the form of a tubular member defining a lumen with a diameter sized to receive at least a portion of the inner frame 750 of a valve 700. The valve 700 can be constructed the same as or similar to, and function the same as or similar to, the valves described above for previous embodiments. For example, the valve 700 can include an outer frame (not shown) and the inner frame 750 as described above for previous embodiments.

In use, the assist member 748 can be movably disposed within a delivery sheath (not shown) used to deliver the valve 700 and be disposed over at least a portion of the inner valve assembly 740. As with the wire assist structure 649, the assist member 748 can hold the inner frame 750 in a small compact configuration and allow for positioning control of the valve 700 (i.e., clocking and advancement) while the outer frame of the valve 700 is being expanded. This can in some cases allow the valve 700 to be functioning (or at least partially functioning) during the positioning phase of the valve 700. With the inner frame 750 held in a compact or small diameter form factor, the valve 700 can be more easily positioned to help seal the annulus with the outer frame (not shown) of the valve 700. When the valve 700 is in the desired final position, the assist member 748 can be removed.

Figure 32:
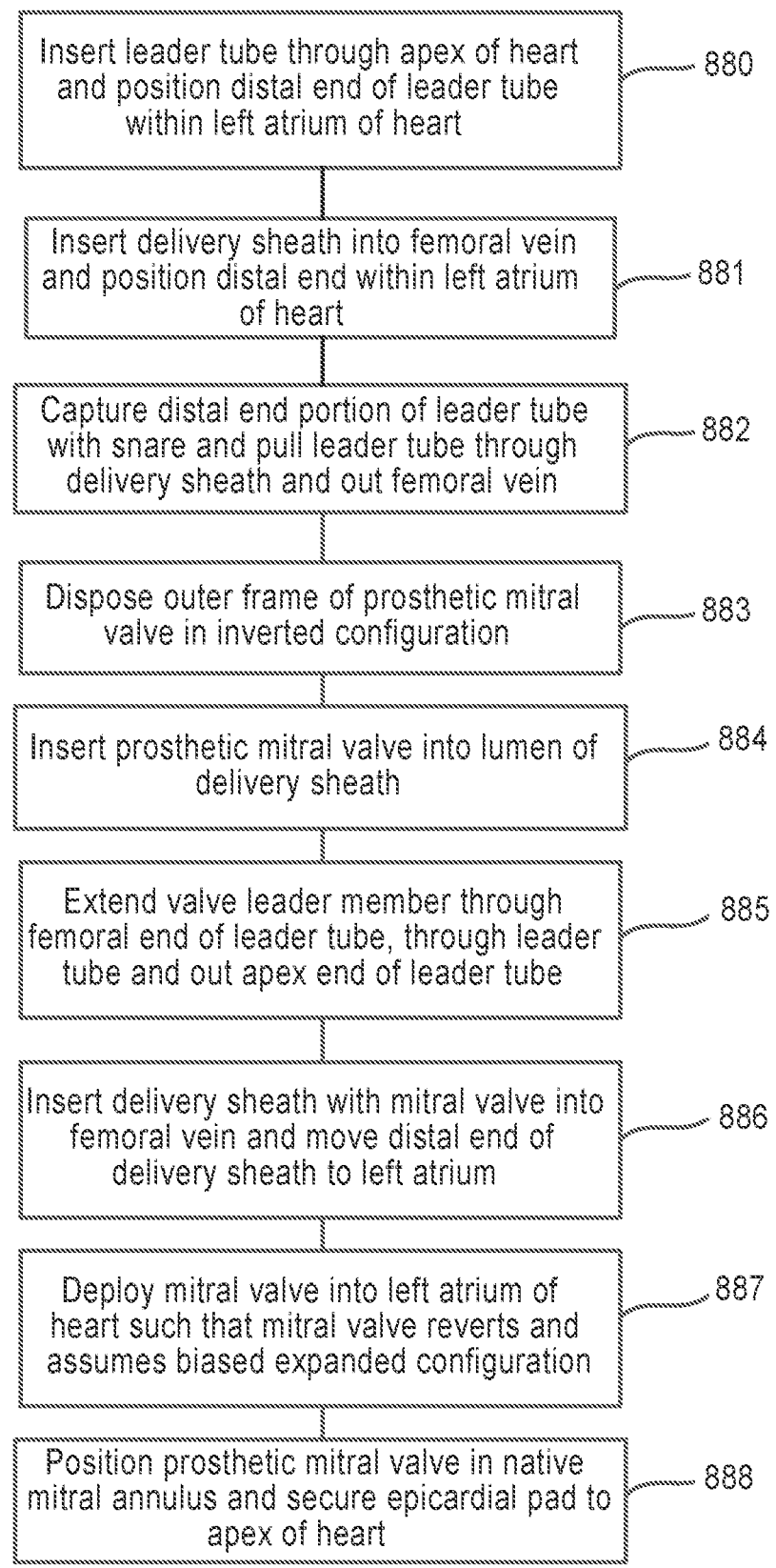
FIG. 32 is a flowchart illustrating a method of delivering a prosthetic mitral valve via a femoral vein, according to an embodiment.

FIG. 32 is a flowchart illustrating a method of deploying a prosthetic mitral valve to a heart using a transfemoral delivery approach. The method includes at 880, inserting a leader tube through an access site on the skin of the patient, through an access puncture site on the apex of the heart, and positioning a distal end portion of the leader tube in the left atrium of the heart. At 881, inserting a delivery sheath with a snare device coupled thereto through an access site into the femoral vein and into the left atrium of the heart. At 882, the leader tube is captured with the snare device, and pulled through the femoral vein such that the leader tube extends between the apex of the heart and the entry to the femoral vein. At 883, an outer frame of a prosthetic mitral valve is disposed in an inverted configuration when the mitral valve is in a biased expanded configuration. For example, the prosthetic mitral valve can be formed with a shape-memory material and have a biased expanded configuration.

At 884, after inverting the outer frame, the prosthetic mitral valve is inserted into a lumen of a delivery sheath such that the prosthetic mitral valve is moved to a collapsed configuration. The delivery sheath can be the same delivery sheath as used with the snare device or a different delivery sheath. At 885, a valve leader member is inserted to the leader tube at the femoral end of the leader tube, and moved through the leader tube until the valve leader member exits the leader tube outside of the apex of the heart. A proximal end of the valve leader member is coupled to a tether line that in turn is coupled to the prosthetic mitral valve and disposed within the delivery sheath. At 886, the delivery sheath is inserted into the femoral vein and moved through the femoral vein and through a septum of a heart until a distal end portion of the delivery sheath is disposed in the left atrium of the heart. At 887, the prosthetic mitral valve is moved distally out of the delivery sheath such that the inverted outer frame of the prosthetic mitral valve reverts, and the prosthetic mitral valve assumes its biased expanded configuration. At 888, the prosthetic mitral valve is positioned within a mitral annulus of the heart and optionally an epicardial pad device can be secured to the apex of the heart to maintain the prosthetic mitral valve in the desired position (e.g., orientation) within the mitral annulus. In some embodiments, rather than securing the prosthetic mitral valve with a tether and epicardial pad, the prosthetic mitral valve can be secured with clips or other coupling methods to a portion(s) of the ventricular wall of the heart.

FIGS. 33-37 illustrate an embodiment of an expandable epicardial pad device that can be used to secure a tether attached to a prosthetic mitral valve to the heart, for example, at the apex of the heart. An epicardial pad device 939 (also referred to herein as "epicardial pad" or "pad") can be used, for example, during a procedure to deliver a prosthetic heart valve as described herein. The epicardial pad 939 can be formed with a small profile such that the epicardial pad 939 can be delivered to the exterior of the heart via a small incision and a small diameter delivery catheter or sheath 963 (see FIGS. 33 and 34). In some embodiments, the delivery sheath 963 can have a diameter, for example, in the range of 3-5 mm. An inner delivery sheath 964 can be movably disposed within a lumen of the delivery sheath 963 and used to hold the tether 936 while the epicardial pad 939 is being deployed as described in more detail below.

Figure 34:
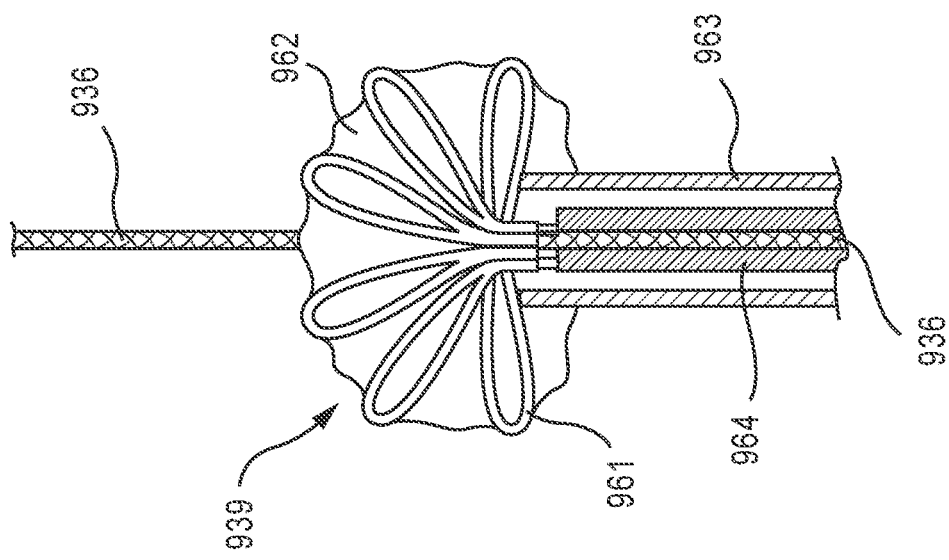
FIG. 34 is a side perspective view of the epicardial pad device of FIG. 33 shown in an expanded configuration.
Figure 33:
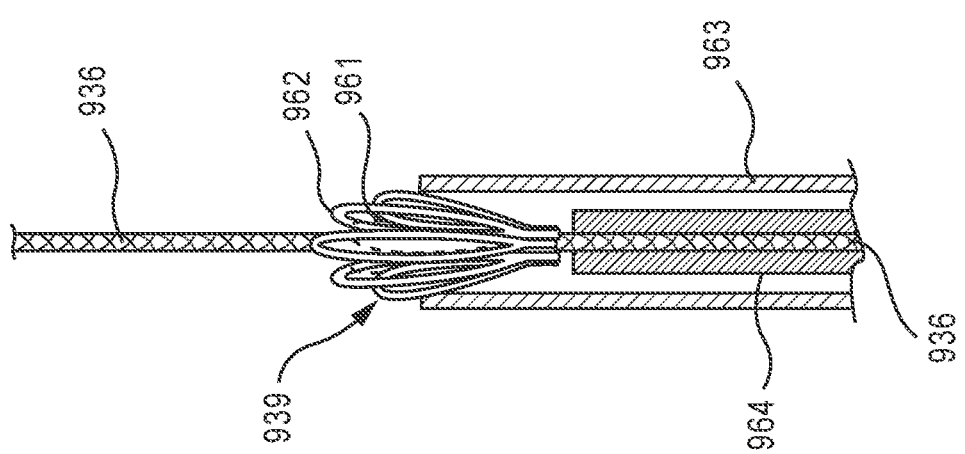
FIG. 33 is a side view of a portion of an epicardial pad device, according to an embodiment, and shown in a collapsed configuration within a delivery sheath.
Figure 35:
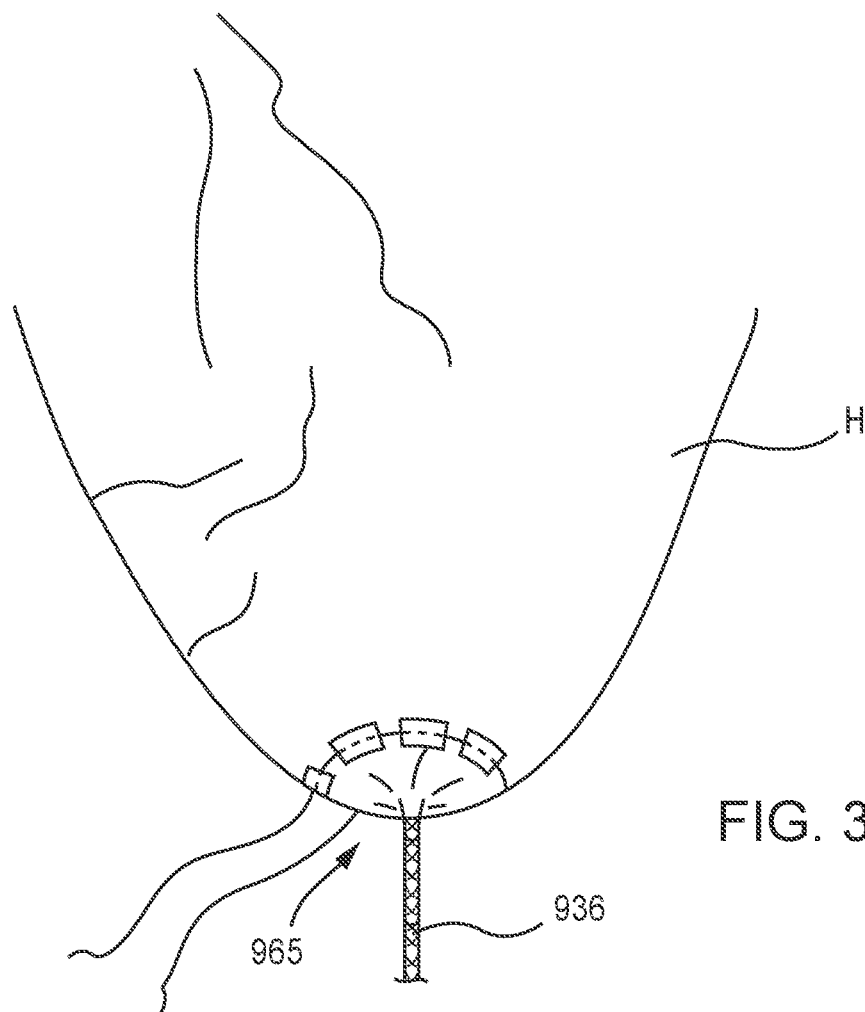
FIG. 35 is a side perspective view of a portion of a heart illustrating purse-string sutures at an apex of the heart prior to securing an epicardial pad device thereto.
Figure 36:
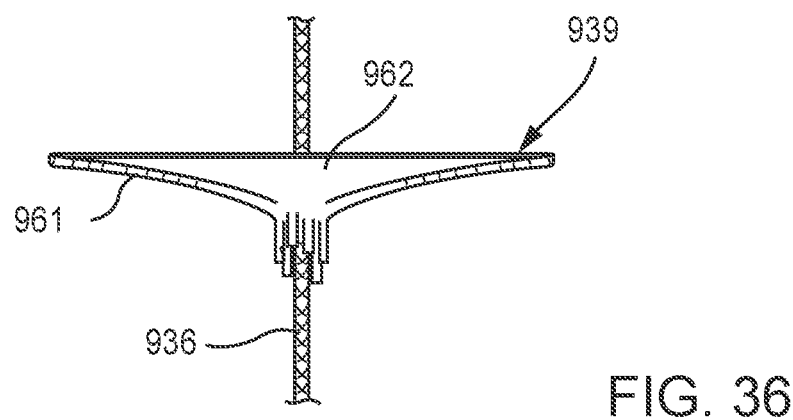
FIG. 36 is a side perspective view of the epicardial pad device of FIG. 33 shown in the expanded configuration.

As shown in FIGS. 33 and 34 the epicardial pad 939 includes a frame member 961 and a fabric cover 962. The frame member 961 can be formed with, for example a shape-memory material such as Nitinol® such that the epicardial pad 939 can have a biased expanded configuration as shown in FIGS. 34 and 36, and can be moved to a collapsed configuration as shown in FIG. 33. For example, as shown in FIG. 33 the epicardial pad 939 can be placed within a lumen of the delivery sheath 963 to move the epicardial pad 939 to the collapsed configuration. The fabric cover 962 can be formed with various suitable material(s) such as, for example, polyester, polyethylene or ePTFE.

In use, after a prosthetic mitral valve has been deployed within the heart H (e.g., via a transfemoral delivery approach as described herein or a transatrial delivery approach), the tether 936 attached to the prosthetic valve (not shown) can extend outside the apex of the heart. The epicardial pad 939 can be used to secure the tether 936 and prosthetic valve in a desired position. With the tether 936 extending outside of the heart, the tether 936 can be threaded through a center opening of the epicardial pad 939 and through a lumen of the inner delivery sheath 964, as shown in FIGS. 33 and 34. The outer delivery sheath 963 can be placed over the inner delivery sheath 964 and the epicardial pad 939 to collapse the epicardial pad 939 as shown in FIG. 33. Although not shown, the epicardial pad 936 can be entirely disposed within the lumen of the outer delivery sheath 963 during delivery. As described above, the outer delivery sheath 963 can have a relatively small outer diameter such that it can be inserted through a small incision in the skin of the patient. When the distal end of the delivery sheath 963 is at a desired location near the apex of the heart, the epicardial pad 939 can be moved outside of the delivery sheath 963 such that the epicardial pad 939 can assume its biased expanded configuration as shown in FIGS. 34 and 36. For example, to move the epicardial pad 939 outside of the lumen of the delivery sheath 963, the delivery sheath 963 can be moved proximally, such that the deliver sheath 963 is removed from epicardial pad 939. Alternatively, the epicardial pad 939 can be moved distally outside of the lumen of the delivery sheath 963. For example, a push rod (not shown) can be used, or the inner delivery sheath 964 in which the tether 936 is disposed can be used to move or push the epicardial pad 939 out of the delivery sheath 963.

Figure 38:
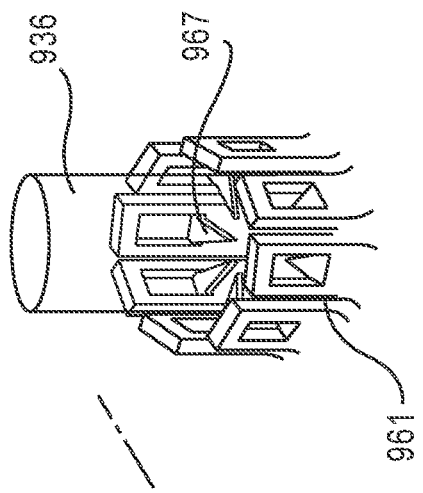
FIG. 38 is an enlarged side perspective view and FIG. 39 is an enlarged bottom view of a portion A in FIG. 37 illustrating an integrated locking mechanism.
Figure 39:
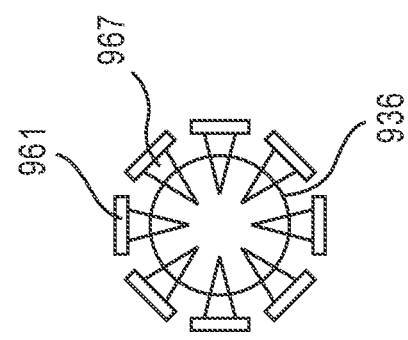
Figure 37:
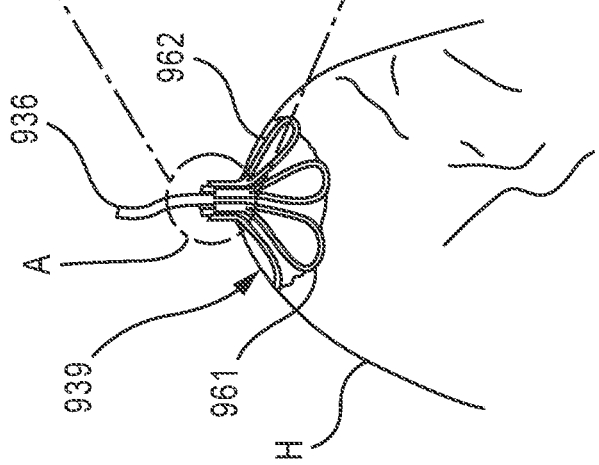
FIG. 37 is a bottom perspective view of a portion of a heart illustrating with the epicardial pad device of FIG. 33 secured thereto.

Prior to moving the expanded epicardial pad 939 into position on the apex of the heart, conventional purse-string sutures 965 at the incision through which the tether 936 extends out of the heart at the apex of the heart can be closed. Although purse-string sutures 965 are illustrated in this embodiment, the epicardial pad 939 can alternatively be implemented without the use of such purse-string sutures 965. The epicardial pad 939, in the expanded configuration, can then be positioned on the apex of the heart. In this embodiment, the epicardial pad 939 includes an integral locking mechanism that includes barbs 967 as shown in FIGS. 37-39. The locking mechanism or barbs 967 can be formed integrally with the frame member 961. As shown in FIGS. 33 and 34, the tether 936 can be inserted through a lumen of the inner delivery sheath 964 such that the delivery sheath 964 can prevent the barbs 967 from contacting the tether 936. For example, the tether 936 can be threaded into the inner delivery sheath 964 prior to the inner delivery sheath 964 and tether 936 being inserted through the center opening of the epicardial pad 939. Thus, the inner delivery sheath 964 can protect the tether 936 from the barbs 967 during deployment of the epicardial pad 939. When the epicardial pad 939 is deployed at the desired position on the apex region of the heart, the inner delivery sheath 964 can be removed uncovering the tether 936 and allowing the barbs 967 to engage or pierce the tether 936 as shown in FIGS. 38 and 39. The barbs 967 can hold or lock the tether 936 and epicardial pad 939 in the desired position. The barbs 967 can be oriented at various different angles relative to a longitudinal axis of the epicardial pad 939, such as, for example, between 45-120 degrees.

In alternative embodiments, other methods of securing the epicardial pad 939 to the heart can be used. For example, in an embodiment in which the epicardial pad 939 does not include an integrated locking mechanism as described above, the distal end portion of the tether 936 can be tied or another securing device such as a clip or locking pin can be used.

Figure 41:
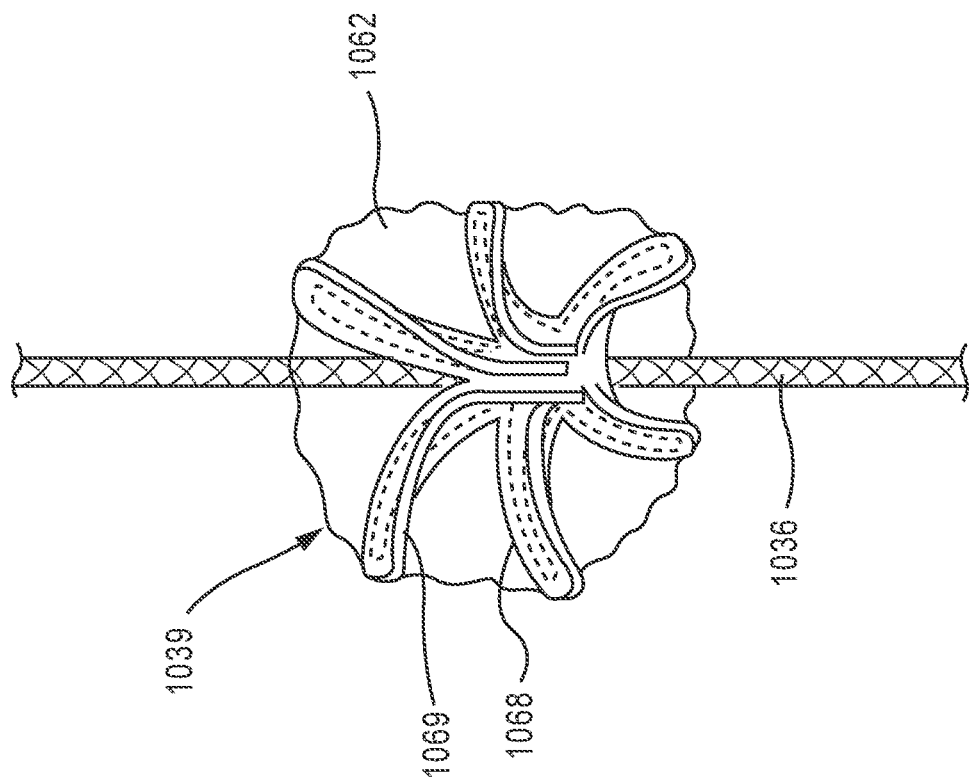
FIG. 41 is a side perspective view of the epicardial pad device of FIG. 40 shown in an expanded configuration.
Figure 40:
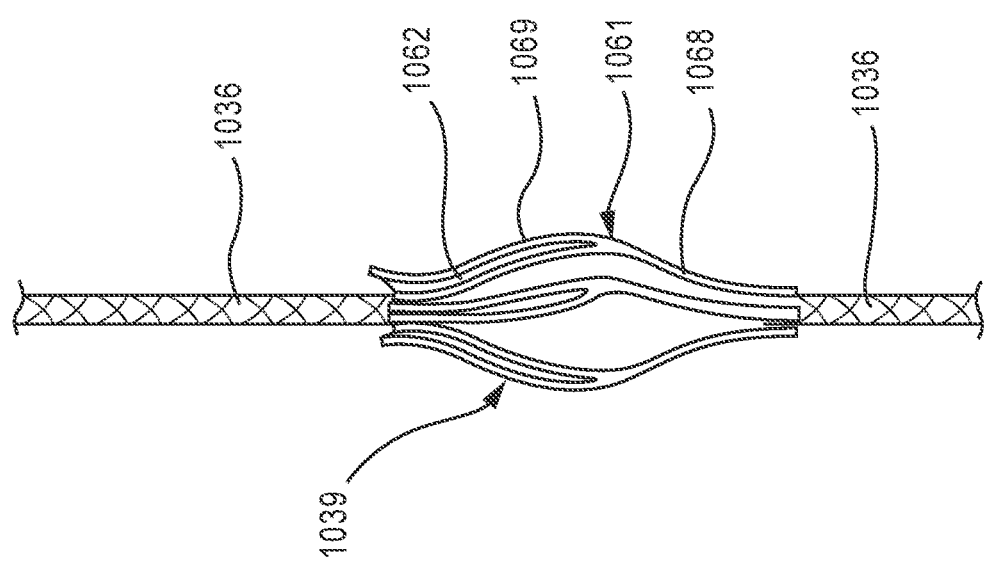
FIG. 40 is a side view of an epicardial pad device, according to another embodiment, and shown in a collapsed configuration.
Figure 42:
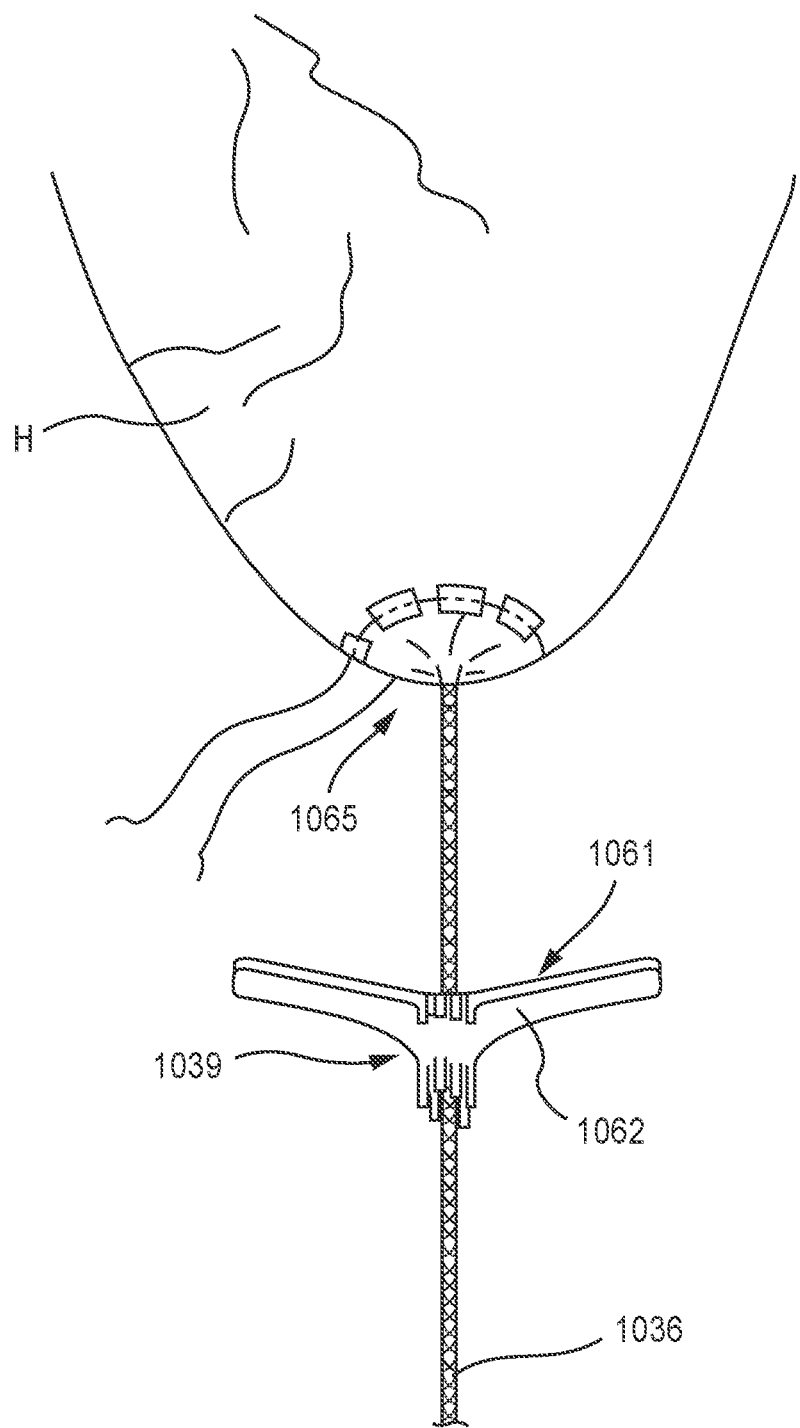
FIG. 42 is a side view of the epicardial device of FIG. 40 shown in the expanded configuration and being deployed near an apex of a heart.

FIGS. 40-42 illustrate another embodiment of an expandable epicardial pad device that can be used to secure a tether attached to a prosthetic mitral valve to the heart, for example, at the apex of the heart. An epicardial pad device 1039 (also referred to herein as "epicardial pad" or "pad") can be used, for example, during a procedure to deliver a prosthetic heart valve as described herein. The epicardial pad 1039 can be formed with a small profile such that the epicardial pad 1039 can be delivered to the exterior of the heart via a small incision and a small diameter delivery catheter or sheath (not shown) as described above for epicardial pad 939.

As shown in FIGS. 40-42, the epicardial pad 1039 includes a frame member 1061 and a fabric cover 1062. In this embodiment, the frame member 1061 includes a first frame portion 1068 and a second frame portion 1069. As with the previous embodiment, the frame member 1061 can be formed with, for example a shape-memory material such as Nitinol®, such that the epicardial pad 1039 can have a biased expanded configuration as shown in FIGS. 41 and 42, and can be moved to a collapsed configuration as shown in FIG. 40. For example, although not shown for this embodiment, the epicardial pad 1039 can be placed within a lumen of a delivery sheath to collapse or move the epicardial pad 1039 to the collapsed configuration. In the expanded configuration, the second frame portion 1069 expands within an interior region defined by the first frame portion 1068 as best shown in FIG. 41. In other words, the second frame portion 1069 and the first frame portion 1068 form a double-layer flower-like shape. The fabric cover 1062 can be formed with, for example, various suitable material(s) such as, for example, polyester, polyethylene or ePTFE, as described above for fabric cover 962.

In use, after a prosthetic mitral valve has been deployed within the heart H (FIG. 42), for example, via a transfemoral delivery approach as described herein, the tether 1036 attached to the prosthetic valve (not shown) can extend outside the apex of the heart. The epicardial pad 1039 can be used to secure the tether 1036 and prosthetic valve in a desired position. With the tether 1036 extending outside of the heart, the tether 1036 can be threaded through a lumen of an inner delivery sheath (not shown), such as inner delivery sheath 964 described above, and through a center opening of the epicardial pad 1039. An outer delivery sheath (not shown) can be placed over the inner delivery sheath to collapse the epicardial pad 1039. As described above, the outer delivery sheath can have a relatively small outer diameter such that it can be inserted through a small incision in the skin of the patient. When the distal end of the delivery sheath is at a desired location near the apex of the heart, the epicardial pad 1039 can be moved outside of the outer delivery sheath such that the epicardial pad 1039 can assume its biased expanded configuration as shown in FIGS. 41 and 42 in a similar manner as described above for epicardial pad 939.

Prior to moving the expanded epicardial pad 1039 into position on the apex of the heart, conventional purse-string sutures 1065 at the incision through which the tether 1036 extends out of the heart at the apex of the heart can be closed. As with the previous embodiment, although purse-string sutures 1065 are illustrated in this embodiment, the epicardial pad 1039 can alternatively be implemented without such purse-string sutures 1065. The epicardial pad 1039, in the expanded configuration, can then be positioned on the apex of the heart. The epicardial pad 1039 can include an integral locking mechanism, similar to or the same as locking mechanism (e.g., barbs) described above to secure or lock the tether 1036 and epicardial pad 1039 in position on the heart. In alternative embodiments, other methods of securing the epicardial pad 1039 to the heart can be used. For example, as described above, the distal end portion of the tether 1036 can be tied or another securing device such as a clip or locking pin can be used.

Figure 43:
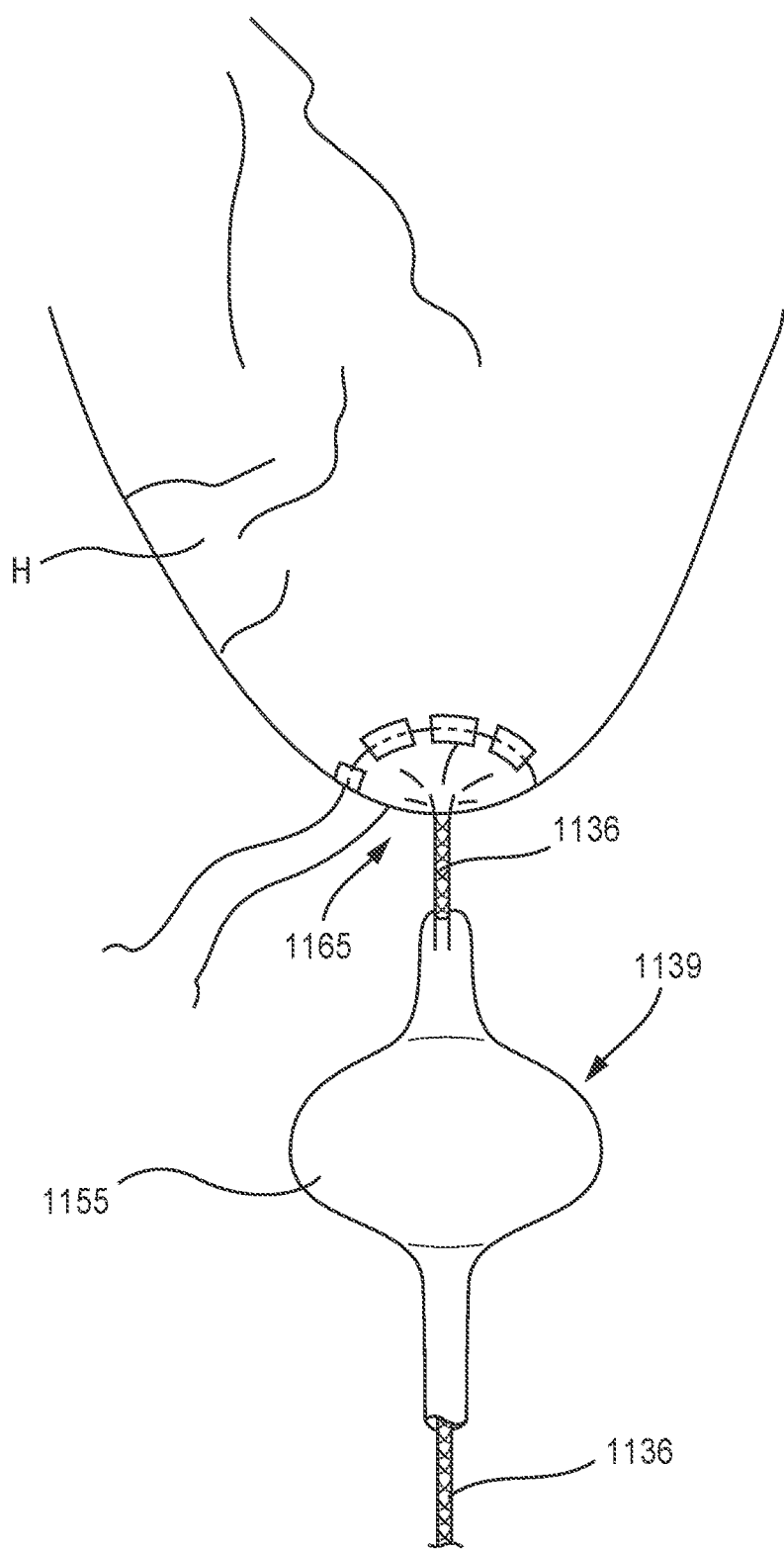
FIG. 43 is a side view of an epicardial pad device, according to another embodiment, and shown in an expanded configuration being deployed near a heart.
Figure 44:
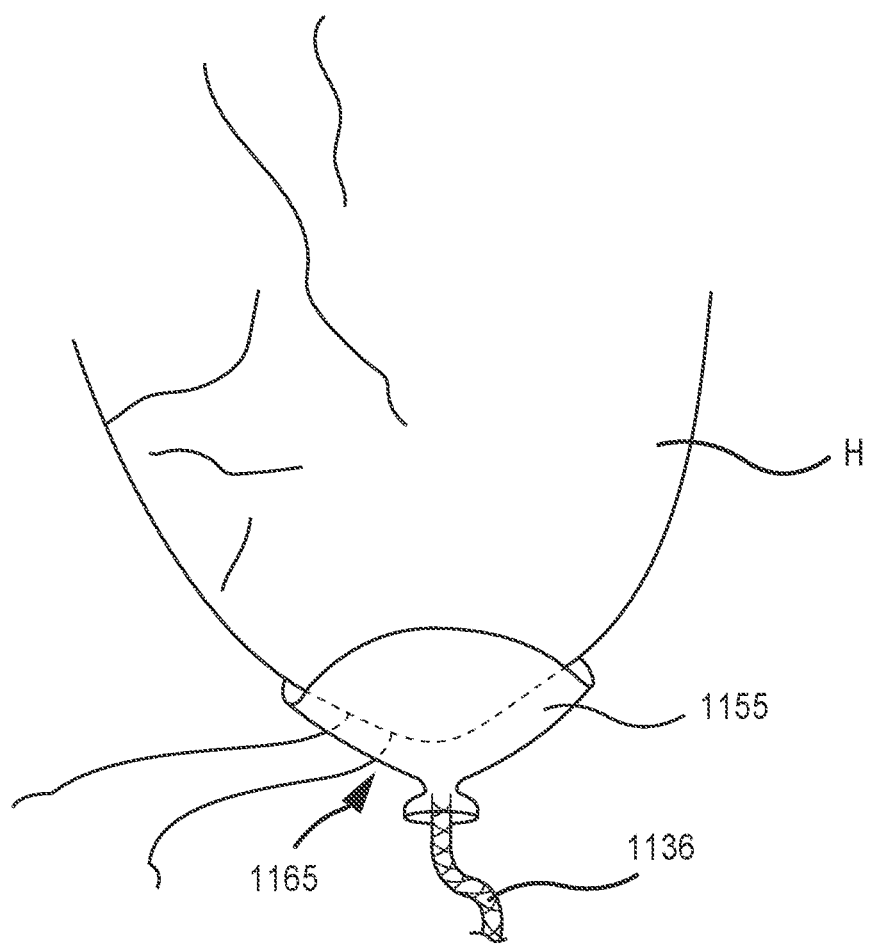
FIG. 44 is a side view of the epicardial pad device of FIG. 43 shown in a collapsed configuration and deployed on the apex of the heart.

FIGS. 43 and 44 illustrate an expandable epicardial pad device 1139 according to another embodiment. The epicardial pad device 1139 can be used in the same or similar manner as described for previous embodiments to secure a tether attached to a prosthetic mitral valve to the heart, for example, at the apex of the heart. The epicardial pad device 1139 (also referred to herein as "epicardial pad" or "pad") can be used, for example, during a procedure to deliver a prosthetic heart valve as described herein. In this embodiment, the epicardial pad device 1139 includes a balloon member 1155. The balloon member 1155 can be small in size such that the balloon member 1155 can be delivered to the exterior of the heart via a small incision and a small diameter delivery catheter or sheath (not shown) as described above for previous embodiments.

The balloon member 1155 can define an inner lumen through which the tether 1136 can be inserted. The epicardial pad 1139 can also include an inflation lumen through which an inflation medium can be communicated to and from the balloon member 1155. For example, the inflation lumen (not shown) can be defined by the balloon member 1155 or by a separate inflation line (not shown) in fluid communication with an interior of the balloon member 1155.

In use, after a prosthetic mitral valve has been deployed within the heart H (FIG. 43), as described herein, the tether 1136 attached the prosthetic valve (not shown) can extend outside the apex of the heart. With the tether 1136 extending outside of the heart, the tether 1136 can be threaded or inserted through the lumen of the balloon member 1155 as described above. The balloon member 1155 can be inflated or deflated when the tether 1136 is inserted into the balloon lumen. The balloon member 1155 can be collapsed or deflated (not shown) and then placed within a lumen of a delivery sheath (not shown). The delivery sheath can be inserted through a small incision in the skin of the patient and a distal end of the delivery sheath disposed at a desired location near the apex of the heart. The epicardial pad 1139 (i.e., balloon member 1155) can be moved outside of the delivery sheath and then can be inflated as shown in FIG. 43.

Purse-string sutures 1165 at the incision through which the tether 1136 extends out of the heart at the apex of the heart can be closed prior to positioning the epicardial pad 1139 on the apex. As with previous embodiments, although purse-string sutures 1165 are illustrated in this embodiment, the epicardial pad 1139 can alternatively be implemented without such purse-string sutures 1165. Prior to positioning the balloon member 1155 on the apex of the heart, the balloon member 1155 can be partially deflated or fully deflated. The balloon member 1155 is then moved distally into contact with the heart where it can collapse inwardly upon itself to form a cup shape as the balloon member 1155 is pushed against the heart, as shown in FIG. 44. The epicardial pad 1139 and tether 1136 can be secured in the desired position with, for example, clip(s) or a locking pin(s) or by tying the tether 1136. In some embodiments, the balloon member 1155 is secured by adhesively coupling the balloon member 1155 to the tether 1136 such that the balloon member 1155 is prevented from moving relative to the tether 1136. In some embodiments, the balloon member 1155 can be adhesively coupled to the tether 1136 and also adhesively coupled to the heart. In some embodiments, the balloon member 1155 is fully deflated and can be filled with an adhesive or a cement material to add strength and rigidity to the balloon member 1155.

Figure 46:
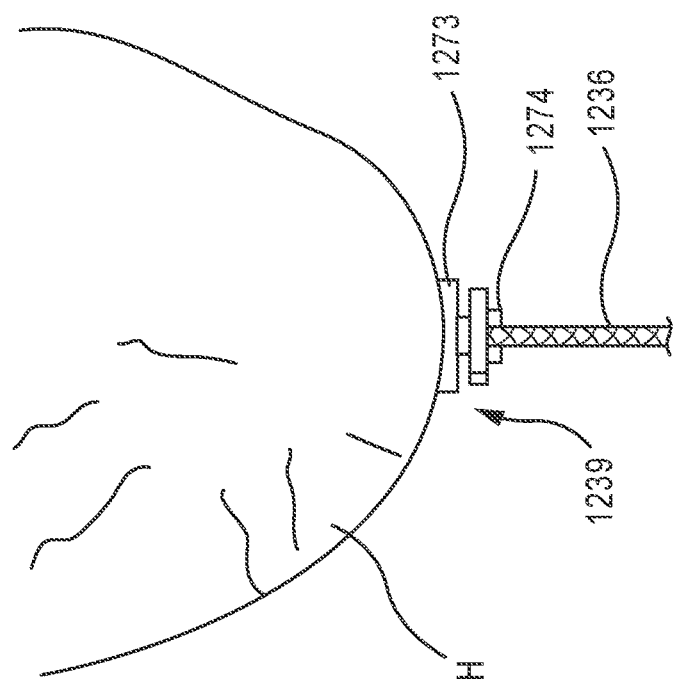
FIGS. 45 and 46 are each a side view of an epicardial pad device, according to another embodiment, and shown being deployed on an apex of a heart.
Figure 45:
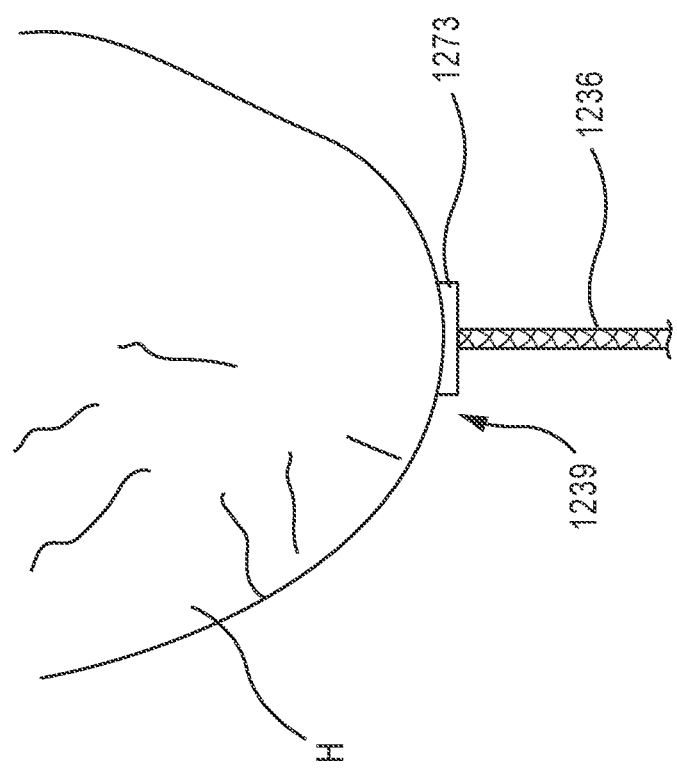
Figure 47:
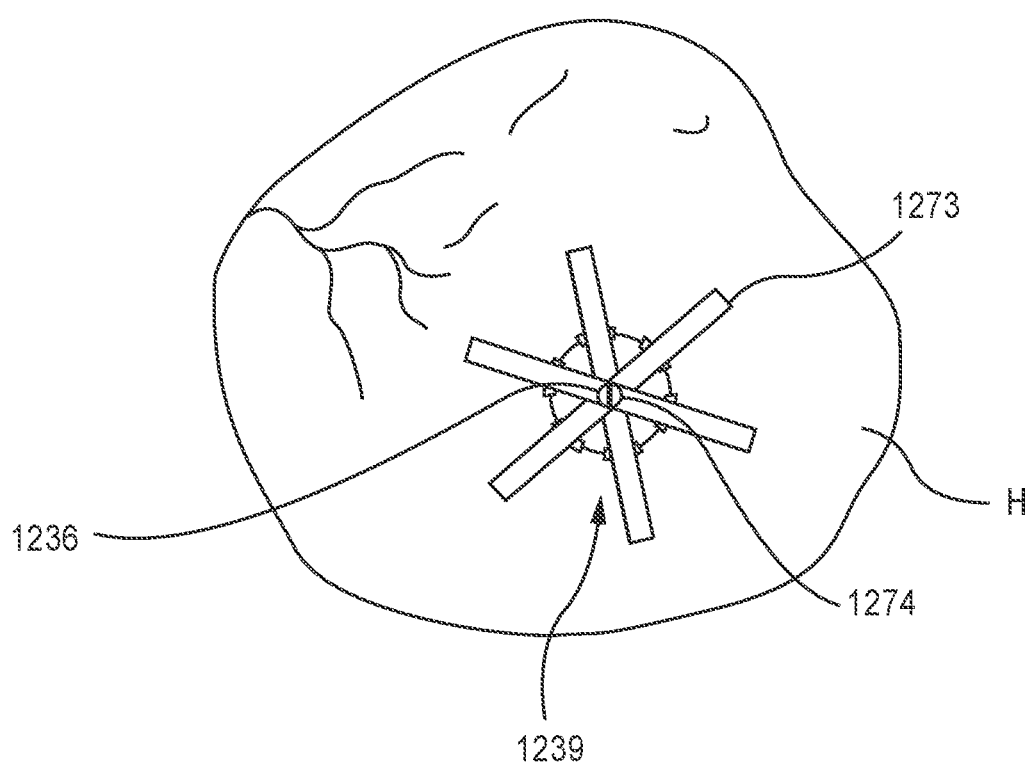
FIG. 47 is a bottom view of a heart with the epicardial pad of FIGS. 45 and 46 secured to the apex of the heart.

FIGS. 45-47 illustrate yet another embodiment of an epicardial pad device that can be used to secure a tether attached to a prosthetic mitral valve to the heart, for example, at the apex of the heart. The epicardial pad device 1239 (also referred to herein as "epicardial pad" or "pad") can be used, for example, during a procedure to deliver a prosthetic heart valve as described herein. In this embodiment, the epicardial pad device 1239 includes multiple stackable pad members 1273 that can be sized such that each stackable pad member 1273 can be delivered separately to the exterior of the heart via a small incision and a small diameter delivery catheter or sheath (not shown). When all of the stackable pad members 1273 are implanted and attached to the heart, the stackable pad members 1273 can define a total surface area of, for example, 2 cm. The stackable pad members 1273 can be formed with, for example, suitable polymer or metal materials such as, for example, PEEK plastic, or stainless steel such as, for example, MP35N stainless steel.

In use, after a prosthetic mitral valve has been deployed within the heart H, for example, via a transfemoral delivery approach as described herein, the tether 1236 attached to the prosthetic valve (not shown) can extend outside the apex of the heart. With the tether 1236 extending outside of the heart, a first stackable pad member 1273 can be slid onto the tether 1236. For example, the stacking members 1273 can define a through-hole in which the tether 1236 can be received. The first stackable pad member 1273 can be slid or moved distally along the tether 1236 until it contacts the surface of the heart H as shown in FIG. 45. A second stackable pad member 1273 can then be slid distally along the tether 1236 until it contacts the first stackable pad member 1273 and then a third stackable pad member 1273 can be slid distally along the tether 1236 until it contacts the second stackable pad member 1273 as shown in FIG. 46. Each stackable pad member 1273 can be oriented at a different angle relative to the tether 1236 as shown in FIG. 47. Using three separate stackable pad members 1273 in this manner can distribute the forces against the surface of the heart more evenly than a single stackable pad member 1273. After the three stackable pad members 1273 have been positioned against the heart, a locking pin 1274 can be inserted laterally through the tether 1236 to secure the stackable pad members 1273 against the surface of the heart. Although three stackable pad members 1273 are shown with respect to epicardial pad device 1239, a different number of stackable pads 1273 can alternatively be used, such as, for example, 2, 4, 5, 6, etc. In some embodiments, it may be desirable to insert a locking pin after each stackable pad member 1273 has been positioned.

Figure 48:
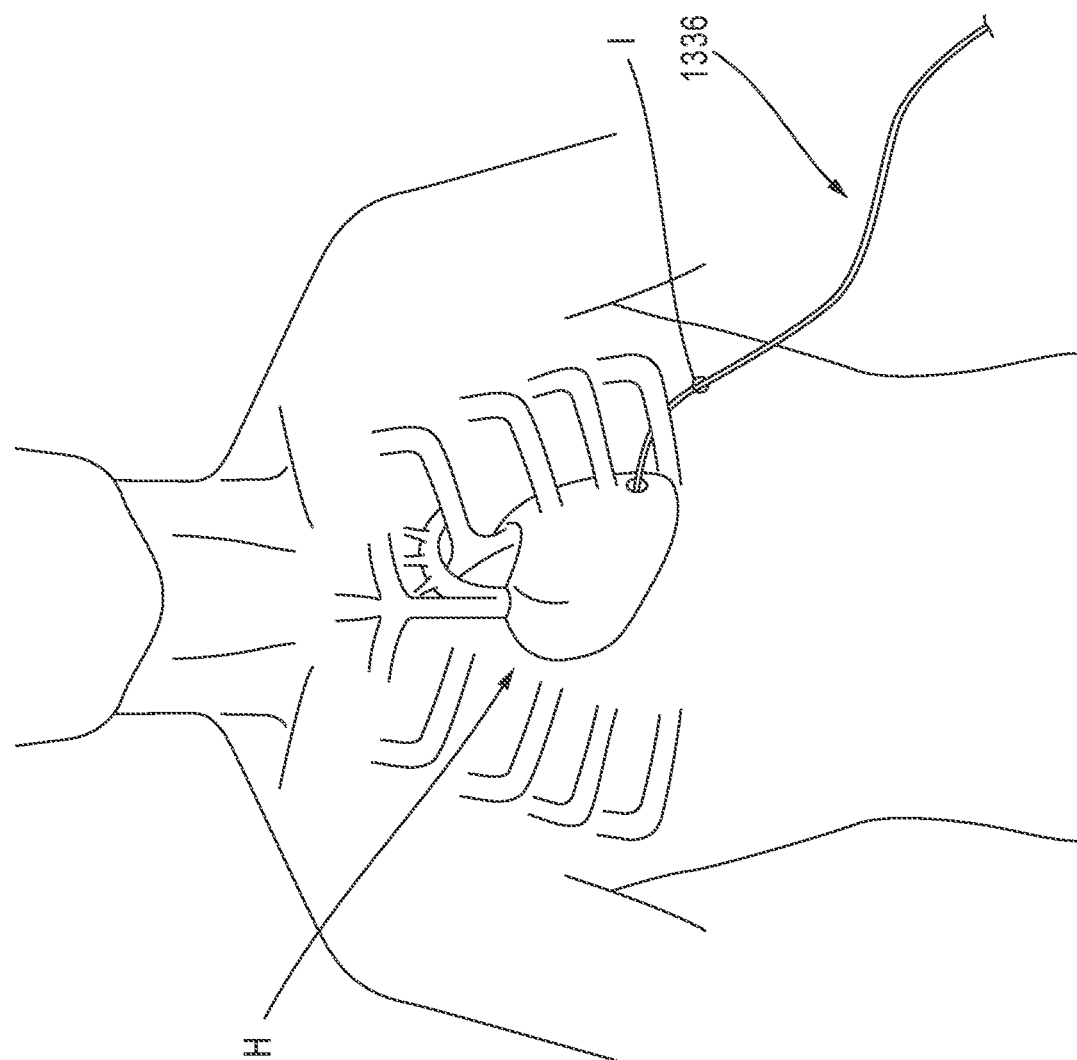
FIG. 48 is an illustration of a patient with a portion of a tether shown extended from within the heart of the patient to outside of the patient, according to an embodiment.
Figure 49:
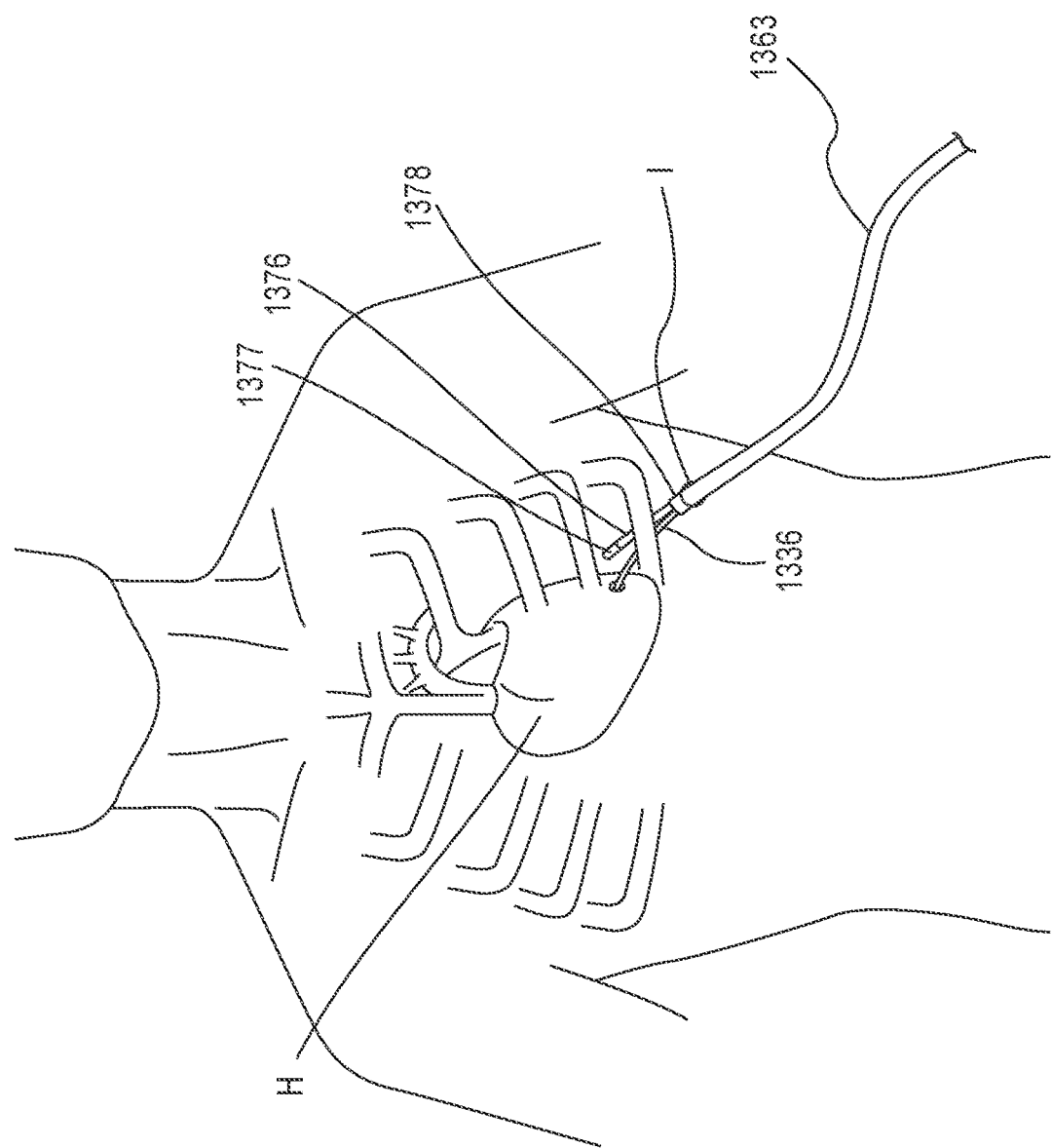
FIG. 49 is an illustration of the patient of FIG. 48 with an expandable tissue dilator device disposed within the patient, shown in a collapsed configuration near the patient's heart, and distal to a distal end of a delivery sheath.
Figure 50:
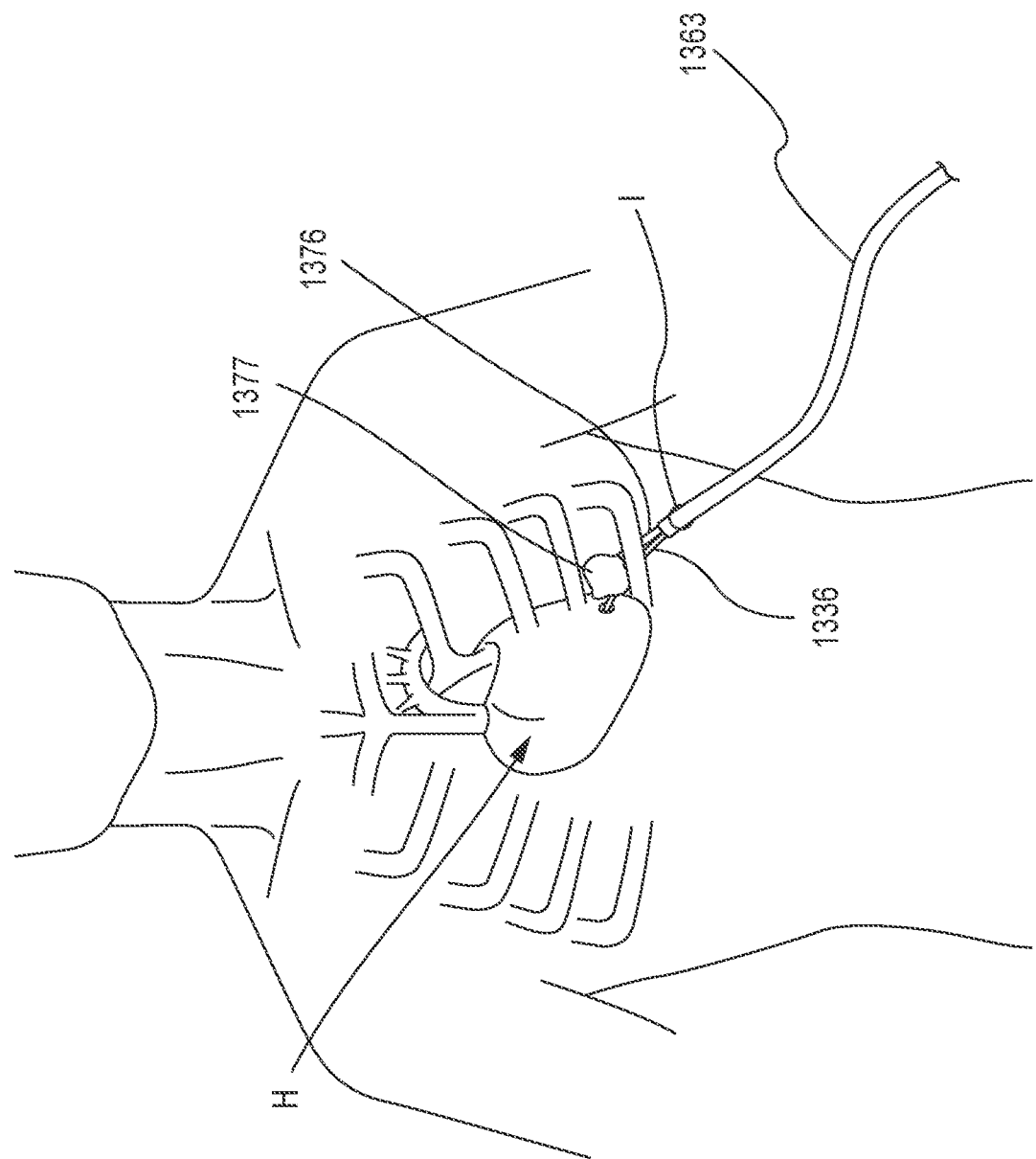
FIG. 50 is an illustration of the expandable tissue dilator device of FIG. 49 in an expanded configuration and disposed within the patient near the patient's heart.
Figure 51:
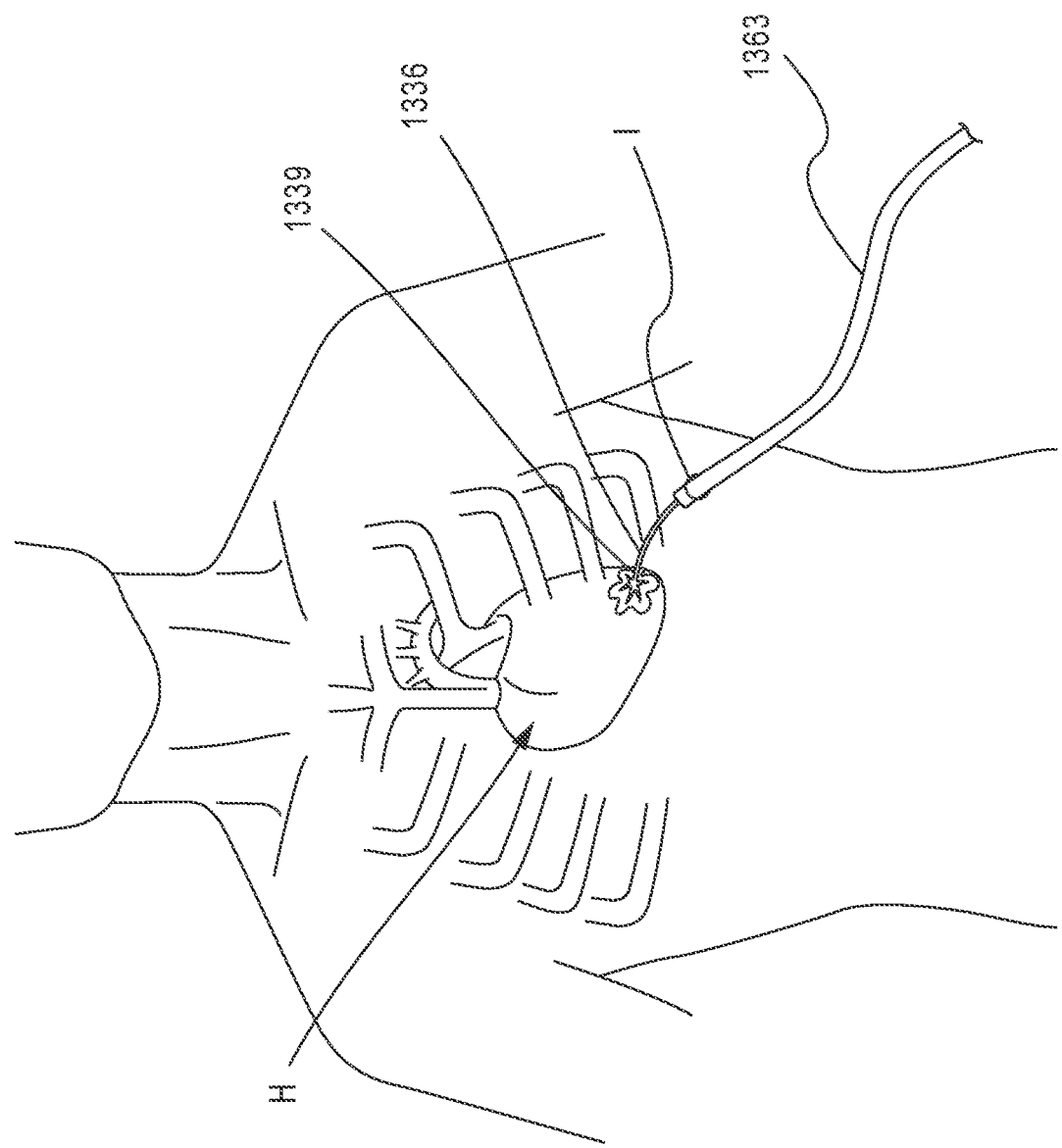
FIG. 51 is an illustration of a portion of an epicardial pad device in an expanded configuration extending from a delivery sheath and disposed near an apex region of the patient's heart.

In some embodiments, prior to deployment of an epicardial pad device to secure a tether and a prosthetic valve in a desired position, as discussed above, for example, with respect to FIGS. 33-37, an expandable tissue dilator device can be used to dilate tissue or otherwise create space suitable for delivery and/or deployment of the epicardial pad device. FIGS. 48-50 illustrate an embodiment of an expandable tissue dilator device 1376 (also referred to herein as "tissue dilator") that can be used to dilate tissue or otherwise create space suitable for delivery and/or deployment of an epicardial pad device 1339 (see FIGS. 51 and 52). The epicardial pad device 1339 can be the same as or similar to any epicardial pad device described herein or in International PCT Application No. PCT/US2014/0049218 (the '218 PCT Application), and can be used in the same or similar manner as described for previous embodiments herein or in the '218 PCT Application to secure a tether attached to a prosthetic mitral valve to the heart, for example, at the apex of the heart.

The tissue dilator 1376 can be used, for example, during a procedure to deliver a prosthetic heart valve transfemorally as described herein or in any other suitable delivery method (e.g., transapical, transatrial, transjugular). In this embodiment the tissue dilator 1376 can include an expandable member 1377 coupled to a distal end of an elongate member (not shown). The expandable member 1377 can be moved between a collapsed configuration for delivery of the expandable member 1377 and an expanded configuration, in which the size (e.g., diameter) of the expandable member 1377 is greater than when in the collapsed configuration. When in the collapsed configuration, the expandable member 1377 can be introduced through a lumen defined by a small profile delivery sheath 1363 and to a desired location within a patient's body (e.g., near a patient's heart H). The expandable member 1377 can be moved to the expanded configuration when at the desired location to dilate surrounding tissue as described in more detail below. In some embodiments, the expandable member 1377 can be a balloon that can be expanded (e.g., inflated) with an inflation medium. For example, the elongate member (not shown) can define a lumen that can communicate an inflation medium to and from the expandable member 1377. The tissue dilator 1376 can be delivered to the exterior of the heart via a small incision I, in which the delivery catheter or sheath 1363 (see FIG. 49) can be inserted. In some embodiments, the delivery sheath 1363 can have a diameter, for example, in the range of 3-5 mm.

In use, after a prosthetic mitral valve has been deployed within the heart H via a transfemoral approach (as described herein), a transapical approach, or other suitable delivery approach, the tether 1336 attached to the prosthetic valve (not shown) can extend outside the apex of the heart H and outside the patient's body via a small incision I (see, e.g., FIG. 48). A proximal end of the tether 1336 can be threaded into and through a distal end of a lumen of the delivery sheath 1363. In this manner, the tether 1336 can provide a guide or otherwise assist in the insertion and movement of the delivery sheath 1363 through the incision I in the skin of the patient. A distal end 1378 of the delivery sheath 1363 can be moved along the tether 1336 and disposed at a desired location near the apex of the heart H (see FIG. 49). The expandable member 1377 of the tissue dilator 1376, when in its collapsed or deflated configuration, can be delivered to the apex region of the heart via the delivery sheath 1363. More specifically, the tissue dilator 1376, with the expandable member 1377 in its collapsed or deflated configuration, can be inserted through the proximal end of the lumen of the delivery sheath 1363, and moved distally towards the distal end of the delivery sheath 1363. In some embodiments, the tissue dilator 1376 can be inserted into the delivery sheath 1363 prior to the delivery sheath 1363 being inserted into the body of the patient. The expandable member 1377 of the tissue dilator 1376 can then be extended outside the distal end of the lumen of the delivery sheath 1363 (see FIG. 49), and moved to its expanded configuration (e.g., inflated), as shown in FIG. 50. For example, to move the expandable member 1377 of the tissue dilator 1376 outside of the lumen of the delivery sheath 1363, the delivery sheath 1363 can be moved proximally, such that the deliver sheath 1363 is removed from the expandable member 1377 of the tissue dilator 1376. Alternatively or additionally, the tissue dilator 1376 can be moved distally such that the expandable member 1377 is moved outside of the lumen of the delivery sheath 1363.

With the expandable member 1377 disposed outside the heart of the patient (e.g., between the patient's ribs and the heart) the expandable member 1377 can be moved to its expanded configuration such that tissue near the expandable member 1377 is dilated by the pressure exerted by the expandable member 1377 on the surrounding tissue. For example, the elongate member of the tissue dilator 1376 can be fluidically coupled directly, or via a fluid line (not shown), to a source of an inflation medium suitable to expand (e.g., inflate) the expandable member 1377. When the expandable member 1377 is disposed at the desired location in the patient near the apex of the heart, the expandable member 1377 can be expanded. In this manner, the tissue dilator 1376 can be used to dilate tissue or otherwise create space suitable for delivery and/or deployment (e.g., expansion and securement to the heart H) of the epicardial pad device 1339, as described in more detail below.

After inflation of the expandable member 1377 of the tissue dilator 1376, and the dilation of the surrounding tissue, the expandable member 1377 of the tissue dilator 1376 can be deflated or collapsed and withdrawn proximally (not shown) through the lumen of the delivery sheath 1363 and outside of the patient. In some embodiments, the delivery sheath 1363 can be removed from the patient's body at the same time or after the tissue dilator 1376 is removed. The tether 1336 extending outside of the patient can be threaded through a center opening of the epicardial pad 1339 and through a lumen of an inner delivery sheath (not shown). The epicardial pad 1339 can be used to secure the tether 1336 and the prosthetic valve (not shown) in a desired position. The delivery sheath 1363 can be placed over the inner delivery sheath and the epicardial pad 1339 to collapse the epicardial pad 1339 in a similar manner as described above for previous embodiments.

The delivery sheath 1363 can then be re-inserted through the small incision I in the skin of the patient and a distal end of the delivery sheath 1363 disposed near the apex of the heart. When the distal end of the delivery sheath 1363 is at the desired location near the apex of the heart, the epicardial pad 1339 can be moved outside the distal end of the delivery sheath 1363 such that the epicardial pad 1339 can assume a biased expanded configuration (see FIG. 51), similar to, for example, the epicardial pad 936 described above, or can be moved to an expanded configuration as described above for epicardial pad 1139. For example, to move the epicardial pad 1339 outside of the lumen of the delivery sheath 1363, the delivery sheath 1363 can be moved proximally, such that the delivery sheath 1363 is removed from epicardial pad 1339. Alternatively, the epicardial pad 1339 can be moved distally outside of the lumen of the delivery sheath 1363. For example, a push rod (not shown) can be used, or the inner delivery sheath (not shown) in which the tether 1336 is disposed can be used to move or push the epicardial pad 1339 out of the delivery sheath 1363. Upon delivery and deployment of the epicardial pad 1339 about the heart H, the delivery sheath 1363 can be removed from the patient and the incision I can be closed with sutures S (see FIG. 52).

In other alternative embodiments, an expandable tissue dilator device can define an inner lumen through which the tether can be inserted. The tissue dilator can also include an inflation lumen through which an inflation medium can be communicated to and from the expandable member of the tissue dilator, as previously described. For example, the inflation lumen can be defined by the tissue dilator or by a separate inflation line that can be disposed within a lumen of the tissue dilator (e.g., a lumen defined by the elongate member of the tissue dilator). In such embodiments, in use, after a prosthetic mitral valve has been deployed within the heart, the tether attached to the prosthetic valve can extend outside the apex of the heart, as described with respect to previous embodiments. With the tether extending outside of the heart, the tether can be threaded or inserted through the lumen of the tissue dilator. As described with respect to previous embodiments, the expandable member of the tissue dilator can be collapsed or deflated and placed within the lumen of the delivery sheath. The delivery sheath can be inserted through a small incision in the skin of the patient and a distal end of the delivery sheath disposed at a desired location near the apex of the heart. The expandable member of the tissue dilator can be moved outside a distal end of the delivery sheath and expanded at or near the heart (e.g., the apex region) as shown and described with respect to the tissue dilator 1376.

After expanding the expandable member of the tissue dilator, and in turn creating space suitable for delivery and/or deployment of an epicardial pad device, the tissue dilator can be collapsed or deflated and withdrawn proximally about the tether and through the lumen of the delivery sheath and outside of the patient. The delivery sheath can be withdrawn from the patient's body through the small incision I. Upon removal of the tissue dilator and the delivery sheath from the tether, the proximal end of the tether can be threaded through a center opening of the epicardial pad and an inner sheath, and the epicardial pad can be delivered to and deployed at the heart using the delivery sheath, as described in previous embodiments.

In alternative embodiments, the tissue dilator can be delivered through a lumen of a delivery sheath separate from the delivery sheath through which the epicardial pad is delivered. Said another way, the tissue dilator can be delivered through a first delivery sheath and the epicardial pad can be delivered through a second delivery sheath.

In yet other alternative embodiments, a delivery sheath can include multiple lumens (e.g., two lumens). In such embodiments, the tether can be routed or threaded through a first lumen of the delivery sheath, and the tissue dilator can be routed and delivered through the second lumen of the delivery sheath. In such an embodiment, after the tissue dilator has been used to dilate the surrounding tissue near the apex of the heart, the tissue dilator can be removed leaving the delivery sheath within the body of the patient. The proximal end of the tether (extending through the first lumen of the delivery sheath) can then be threaded through an epicardial pad and an inner sheath as described above. The epicardial pad and inner sheath can then be inserted into the proximal end of the delivery sheath (e.g., delivery sheath 1363) and moved distally to the distal end of the delivery sheath. For example, the inner sheath can push the epicardial pad distally along the tether. The epicardial pad can then be deployed out the distal end of the delivery sheath and secured to the apex of the heart, as described above for previous embodiments.

In another embodiment, a delivery device can define a lumen that can receive both a dilator device and an expandable epicardial pad. For example, FIGS. 53-57 illustrate an embodiment of an epicardial pad delivery device that can be used to deliver an expandable epicardial pad that can be used to secure a tether attached to a prosthetic mitral valve to the heart, for example, at the apex of the heart. An expandable epicardial pad delivery device 1401 (also referred to herein as "pad delivery device" or "delivery device") can be used, for example, during a procedure to deliver a prosthetic heart valve (e.g., a prosthetic mitral valve) as described herein. The delivery device 1401 can be used to deliver an expandable epicardial pad 1439. The delivery device 1401 can have a small outer diameter such that the delivery device 1401 can be inserted through a small incision in a patient to deliver the epicardial pad 1439 to the exterior of the heart of the patient. The delivery device 1401 includes an outer delivery sheath 1463, an expandable tissue dilator device 1476, and a stopper tube 1489.

The expandable epicardial pad 1439 (also referred to as "epicardial pad" or "pad") can have a collapsed configuration for delivery of the pad 1439 within a body of a patient, and an expanded configuration. When in the collapsed configuration, the pad 1439 can have a small profile such that the pad 1439 can be disposed within a lumen of the delivery device 1401. A tether 1436 attached to a prosthetic mitral valve (not shown) deployed within the heart H can extend through the delivery device 1401 as described in more detail below.

The delivery sheath 1463 includes an elongate member 1411 and at least one retracting element 1479. The delivery sheath 1463 also defines a lumen 1413 that can receive therethrough the dilator device 1476. The elongate member 1411 can have an outer diameter, for example, in the range of 3-5 mm. The retracting element 1479 can be located at or near a distal end of the delivery sheath 1463. The at least one retracting element 1479 can include a lip that extends partially or fully around the circumference of the delivery sheath 1463. The lip can be shaped such that the retracting element 1479 can pull tissue proximally when the delivery sheath 1463 is moved in a proximal direction. For example, in this embodiment, at least a portion of the lip can form an angle relative to the elongate member 1411 such that the lip is capable of catching and pulling tissue. For example, the retracting element 1479 can be used to retract or separate pericardium tissue from epicardial tissue at the surface of the heart as described in more detail below. The angle can be, for example, about 90°. In other configurations, the angle can be greater than or less than 90°.

In some embodiments, the retracting element 1479 can include a threaded feature (not shown). Rotation of the delivery sheath 1463 in a first direction can cause the threaded feature to engage with and/or capture tissue. Rotation of the delivery sheath 1463 in a second direction opposite the first direction can cause the thread feature to release the tissue. For example, depending on the direction of thread or threads in the threaded feature, the threaded feature could be rotated clockwise to capture the tissue (e.g., pericardium) such that the retracting element 1479 can be used to pull the tissue proximally. To release the tissue from the retracting element 1479, the threaded feature can be rotated counter-clockwise. In other embodiments, the retracting element 1479 can be configured to release captured tissue when the retracting element 1479 reaches a predetermined tension. In some embodiments, the retracting element 1479 can be collapsible from an expanded configuration in which the retracting element 1479 engages with and captures tissue to a collapsed configuration in which the retracting element 1479 disengages with the captured tissue.

The expandable tissue dilator device 1476 (also referred to herein as "tissue dilator" or "dilator device") can be movably disposed within the lumen 1413 of the delivery sheath 1463. The tissue dilator 1476 can be used to dilate tissue or otherwise create space suitable for delivery and/or deployment of the epicardial pad device 1439. The tissue dilator 1476 can include an expandable member 1477 coupled to a distal end of an elongate member 1491 and can define a lumen 1415. The expandable member 1477 can be moved between a collapsed configuration for delivery of the expandable member 1477 and an expanded configuration, in which the size (e.g., diameter) of the expandable member 1477 is greater than when in the collapsed configuration. When in the collapsed configuration, the expandable member 1477 can be introduced through the lumen 1413 of the delivery sheath 1463 to a desired location within a patient's body (e.g., near a patient's heart H). The expandable member 1477 can be moved to the expanded configuration when at the desired location to dilate surrounding tissue as described in more detail below. In some embodiments, the expandable member 1477 can be a balloon that can be expanded (e.g., inflated) with an inflation medium. For example, the elongate member 1491 can define an inflation lumen (not shown) that can communicate an inflation medium to and from the expandable member 1477.

Figure 53:
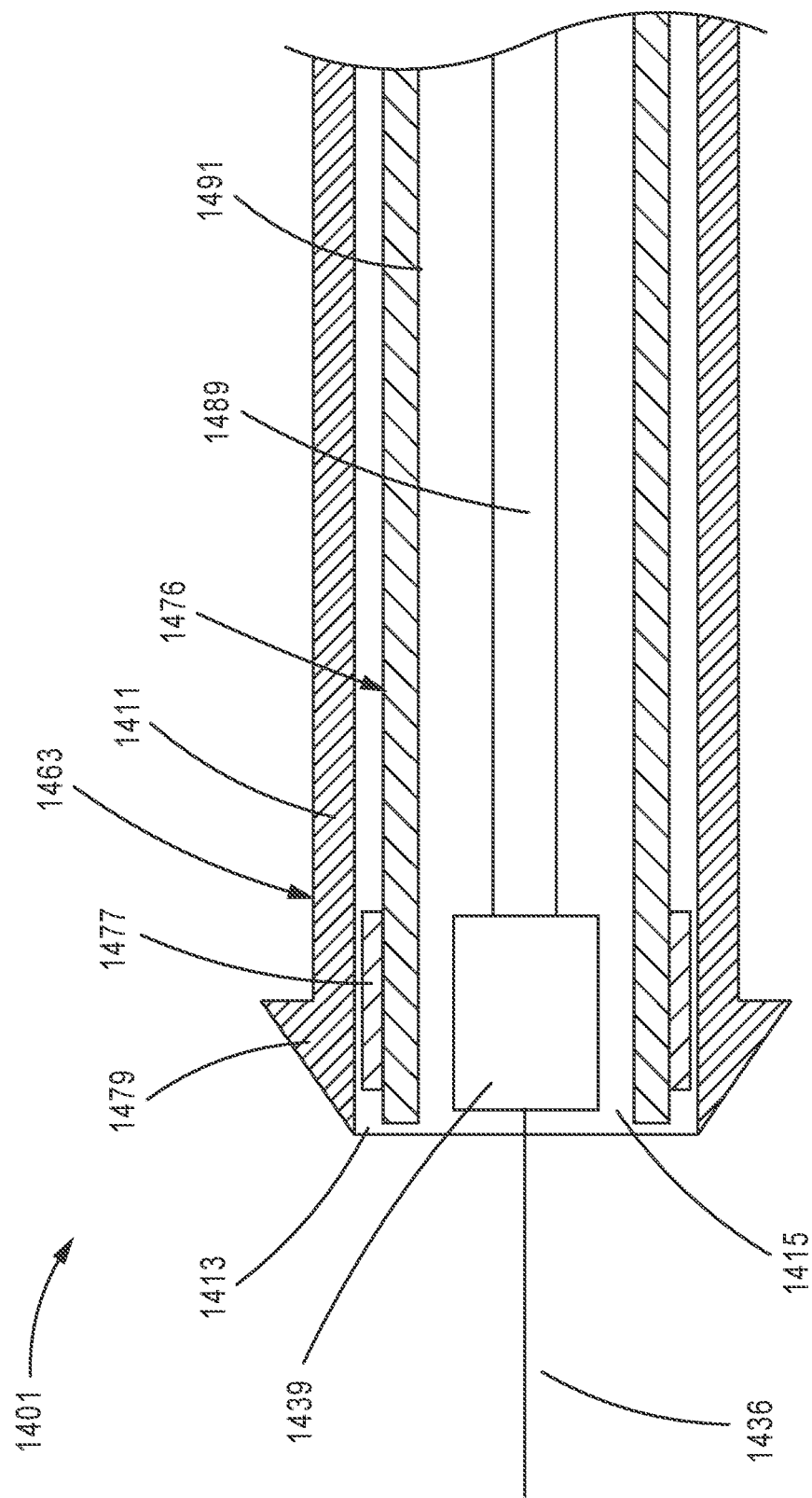
FIG. 53 is a partial cross-sectional side view of a portion of an epicardial pad delivery device, according to an embodiment, in an undeployed configuration.
Figure 54:
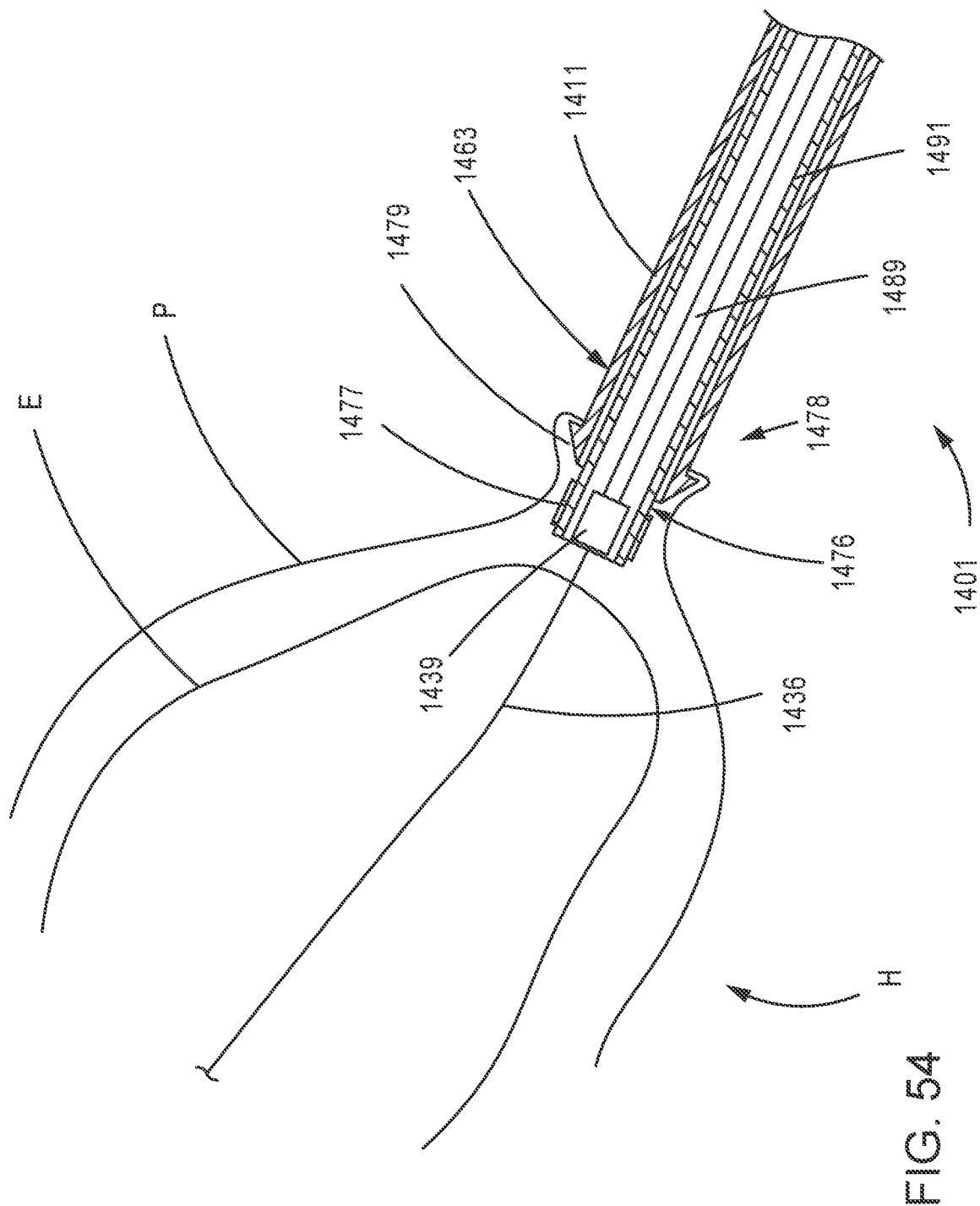
FIG. 54 is a partial cross-sectional side view of the epicardial pad delivery device of FIG. 53 during a stage of a procedure to deliver an epicardial pad device to the apex region of a patient's heart.

As described above, the expandable epicardial pad 1439 can have a collapsed configuration for delivery of the epicardial pad 1439 to the exterior of the heart. As shown in FIGS. 53 and 54, in this embodiment, the epicardial pad 1439 is disposed within a lumen 1415 of the tissue dilator 1476 to deliver the epicardial pad 1439 to the heart. The epicardial pad 1439 can also define an inner lumen (not shown) through which the tether 1436 can be inserted. The epicardial pad 1439 can be the same as or similar to any epicardial pad devices described herein or in International PCT Application No. PCT/US2014/0049218 (the '218 PCT Application), and can be used in the same or similar manner as described for other embodiments herein or in the '218 PCT Application to secure a tether attached to a prosthetic mitral valve to the heart, for example, at the apex of the heart. For example, the epicardial pad 1439 can include an expandable balloon that is the same as or similar to the balloon member 1155 described above with reference to FIG. 43. Alternatively, although not shown, the epicardial pad 1439 can be biased toward an expanded configuration and be movable between a collapsed configuration in which the epicardial pad 1439 is compressed within the tissue dilator 1476 and the expanded configuration when moved out of the tissue dilator 1476.

The stopper tube 1489 can define an inner lumen through which the tether 1436 can be inserted. The tether 1436 can be movably disposed within the stopper tube 1489 such that the stopper tube 1489 can control the movement of the expandable epicardial pad 1439. Said another way, the stopper tube 1489 can be used to prevent proximal movement of the expandable epicardial pad 1439 and to push the expandable epicardial pad 1439 distally relative to the tissue dilator 1476 and/or the outer delivery sheath 1463. The stopper tube 1489 can be releasably attachable to the epicardial pad 1439 such that the stopper tube 1489 is secured to the epicardial pad 1439 during insertion and/or delivery of the epicardial pad 1439. In other embodiments, the stopper tube 1489 is configured to abut a portion of the epicardial pad 1439 such that it can limit proximal movement of the epicardial pad 1439 and push the epicardial pad 1439 distally. The stopper tube 1489 can also include an inflation lumen (not shown) through which an inflation medium can be communicated to and from the epicardial pad 1439. Alternatively, the inflation lumen can be defined by a separate inflation line (not shown) in fluid communication with an interior of the epicardial pad 1439.

In use, after a prosthetic mitral valve (not shown) has been deployed within the heart H via a transfemoral approach (as described herein), a transapical approach, a transjugular approach, or another suitable delivery approach, the tether 1436 attached to the prosthetic valve can extend outside the apex of the heart H and outside the patient's body via a small incision (similar to incision I as shown above in FIG. 48). A proximal end of the tether 1436 can be threaded into and through the delivery device 1401. Specifically, when the delivery device 1401 is in the configuration of FIG. 53 in which the epicardial pad 1439 and stopper tube 1489 are disposed within the lumen 1415 of the tissue dilator 1476 and the tissue dilator 1476 is disposed within the lumen 1413 of the delivery sheath 1463, the proximal end of the tether 1436 can be threaded through the lumen of the epicardial pad 1439 and the lumen of the stopper tube 1489. In this manner, the tether 1436 can provide a guide or otherwise assist in the insertion and movement of the delivery device 1401 through the incision in the skin of the patient. A distal end of the delivery device 1401 can be moved along the tether 1436 and disposed at a desired location near the apex of the heart H. A distal end 1478 of the delivery sheath 1463 can then be inserted through the pericardium P of the heart H such that the retracting element 1479 is between the pericardium P and the epicardium E.

FIG. 54 is a cross-sectional illustration of the delivery device 1401 after insertion of the distal end 1478 of the delivery device 1401 between the pericardium P and the epicardium E. As shown in FIG. 54, the delivery sheath 1463 can be pulled proximally such that the pericardium P is pulled proximally by the retracting element 1479 relative to the epicardium E, creating a space between the pericardium P and the epicardium E. The proximal movement of the delivery sheath 1463 relative to the tissue dilator 1476 results in the expandable member 1477 being disposed distally of the distal end 1478 of the delivery sheath 1463. Alternatively or additionally, the tissue dilator 1476 can be moved distally such that the expandable member 1477 is moved outside of the lumen of the delivery sheath 1463.

Alternatively, rather than arranging the tissue dilator 1476, the epicardial pad 1439, and the stopper tube 1489 within the delivery sheath 1463 prior to insertion of the delivery device 1401, in some embodiments, the components of the delivery device 1401 can be inserted in stages. The tether 1436 can be threaded into and through the lumen 1413 of the delivery sheath 1463 and the delivery sheath 1463 can then be moved along the tether 1436 and inserted through the pericardium P of the heart H such that the retracting element 1479 is disposed between the pericardium P and the epicardium E. The tissue dilator 1476 can then be delivered to the apex region of the heart H via the delivery sheath 1463. More specifically, the tissue dilator 1476, with the expandable member 1477 in its collapsed or deflated configuration, can be inserted through the proximal end of the lumen 1413 of the delivery sheath 1463, and moved distally towards the distal end 1478 of the delivery sheath 1463. The tether 1436 extending outside of the patient can then be threaded through a center opening of the epicardial pad 1439. Before insertion, the delivery sheath 1463 and the tissue dilator 1476 can be placed over the epicardial pad 1439 to collapse the epicardial pad 1439 in a similar manner as described above for previous embodiments. Alternatively, the epicardial pad 1439 can be threaded over the tether 1436 and into the lumen 1413 of the tissue dilator 1476.

Figure 55:
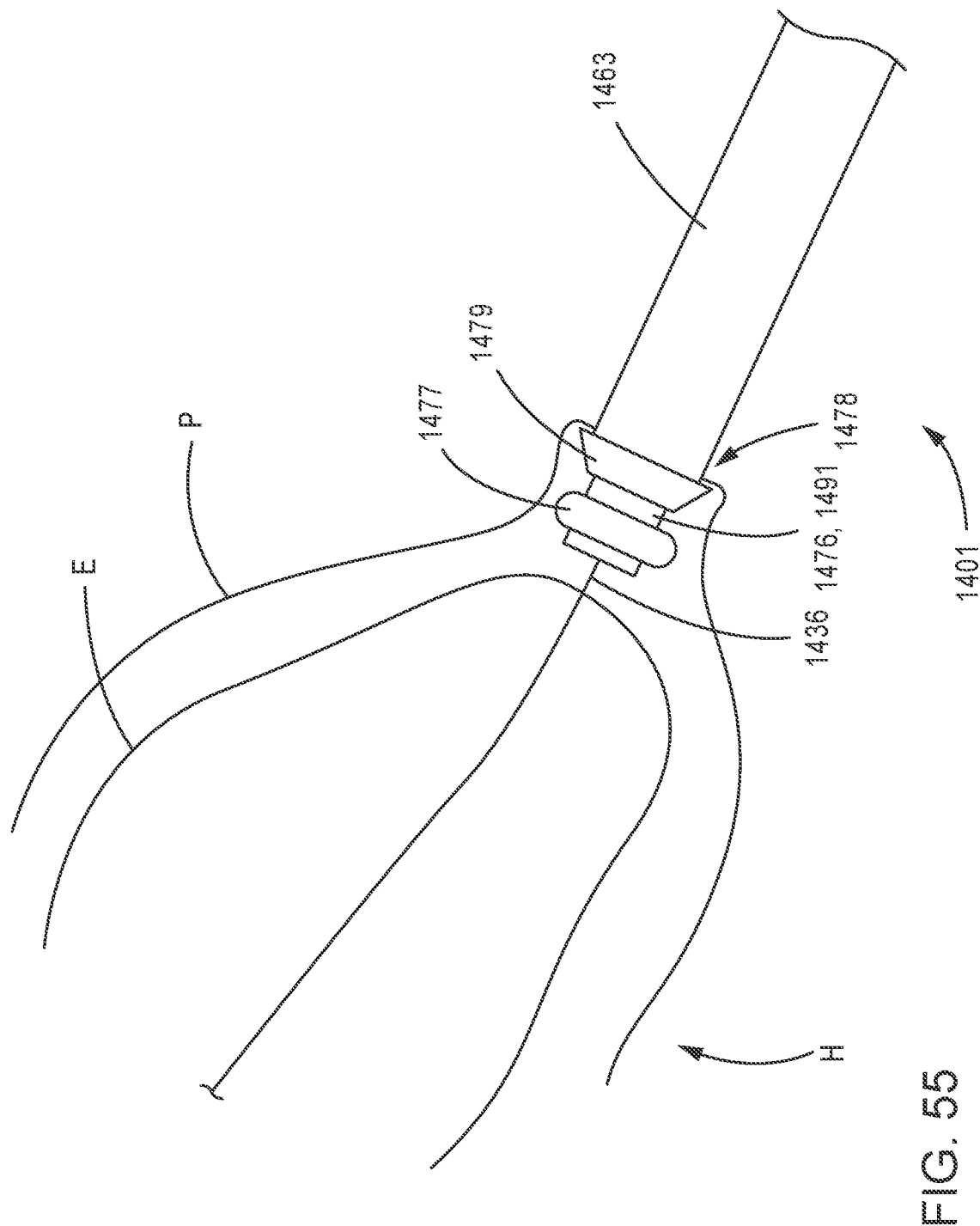
FIG. 55 is a side view illustration of the epicardial pad delivery device of FIG. 53 during another stage of a procedure to deliver an epicardial pad device to the apex region of a patient's heart.

FIG. 55 is a side view illustration of the delivery device 1401 after the expandable member 1477 has been expanded. As shown in FIG. 55, after the delivery sheath 1463 has been retracted and the expandable member 1477 is positioned distally of the distal end of the delivery sheath 1463 between the pericardium P and the epicardium E, the expandable member 1477 can be moved to its expanded configuration such that tissue near the expandable member 1477 is dilated by the pressure exerted by the expandable member 1477 on the surrounding tissue. For example, the elongate member 1491 of the tissue dilator 1476 can be fluidically coupled directly or via a fluid line (not shown) to a source of an inflation medium suitable to expand (e.g., inflate) the expandable member 1477. When the expandable member 1477 is disposed at the desired location in the patient, the expandable member 1477 can be expanded. In this manner, the tissue dilator 1476 can be used to dilate tissue or otherwise create space suitable for delivery and/or deployment (e.g., expansion and securement to the heart H) of the epicardial pad device 1439, as described in more detail below.

Figure 56:
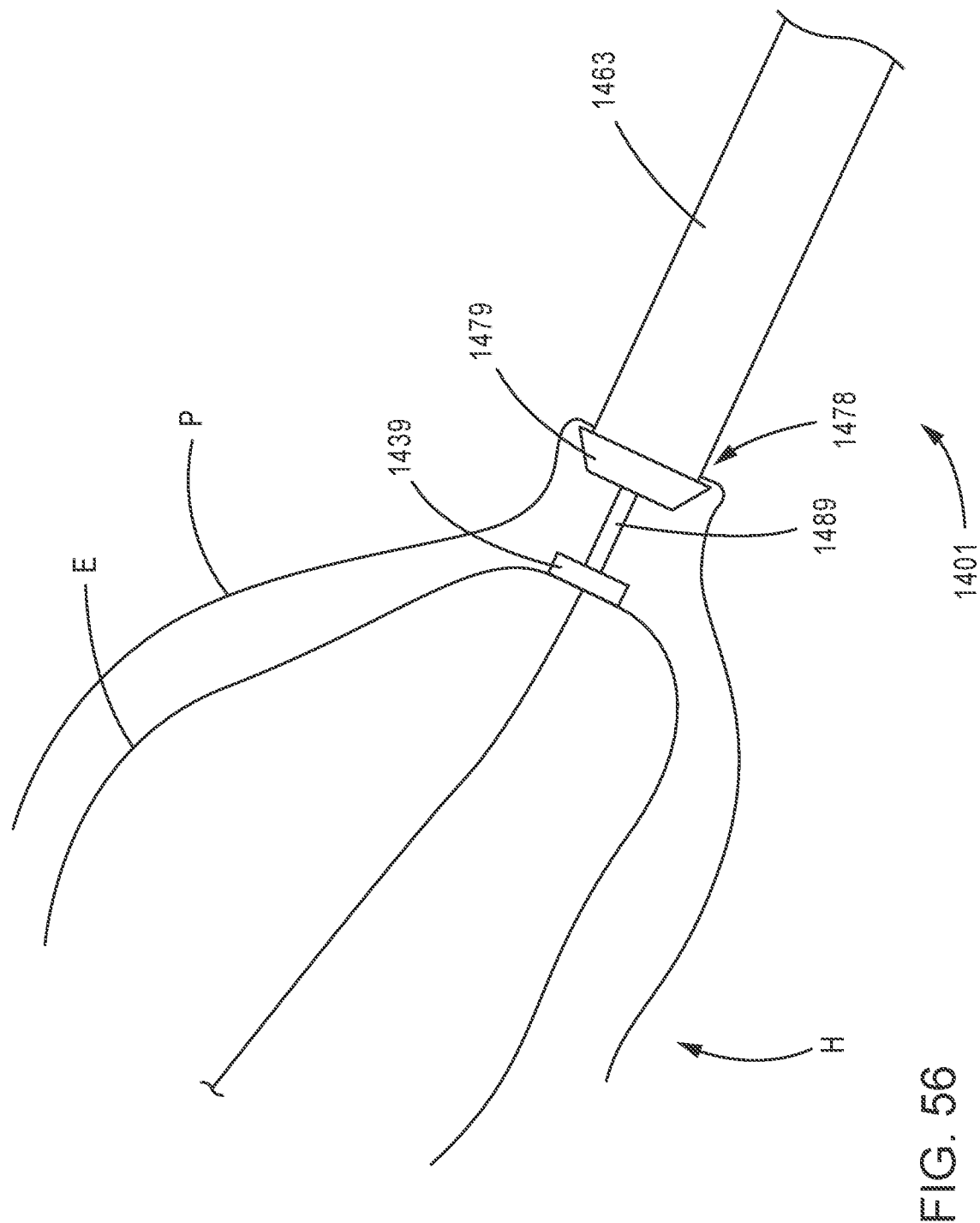
FIG. 56 is a side view illustration of the epicardial pad delivery device of FIG. 53 during another stage of a procedure to deliver an epicardial pad device to the apex region of a patient's heart.

After inflation of the expandable member 1477 of the tissue dilator 1476, and the dilation of the surrounding tissue, the expandable member 1477 of the tissue dilator 1476 can be deflated or collapsed and withdrawn proximally into the lumen 1413 of the delivery sheath 1463 or through the lumen 1413 of the delivery sheath 1463 and outside of the patient. The proximal movement of the tissue dilator 1476 relative to the epicardial pad 1439 causes the epicardial pad 1439 to be disposed distally of the distal end of both the delivery sheath 1463 and the tissue dilator 1476. The stopper tube 1489 can prevent undesired proximal movement of the epicardial pad 1439. Alternatively or additionally, the epicardial pad 1439 can be moved distally outside of the lumen of the delivery sheath 1463 and the lumen of the tissue dilator 1476. For example, the stopper tube 1489 can be used to move or push the epicardial pad 1439 out of the delivery sheath 1463. When the epicardial pad 1439 has been moved distally relative to the delivery sheath 1463 and the tissue dilator 1476, the epicardial pad 1439 can assume a biased expanded configuration, similar to, for example, the epicardial pad 936 described above, or can be moved to an expanded configuration as described above for epicardial pad 1139. The stopper tube 1489 can then be moved distally to position the epicardial pad 1439 against the apex of the heart H as shown in FIG. 56. When the epicardial pad 1439 is in the desired position, the stopper tube 1489 can release or be detached from the epicardial pad 1439.

Figure 52:
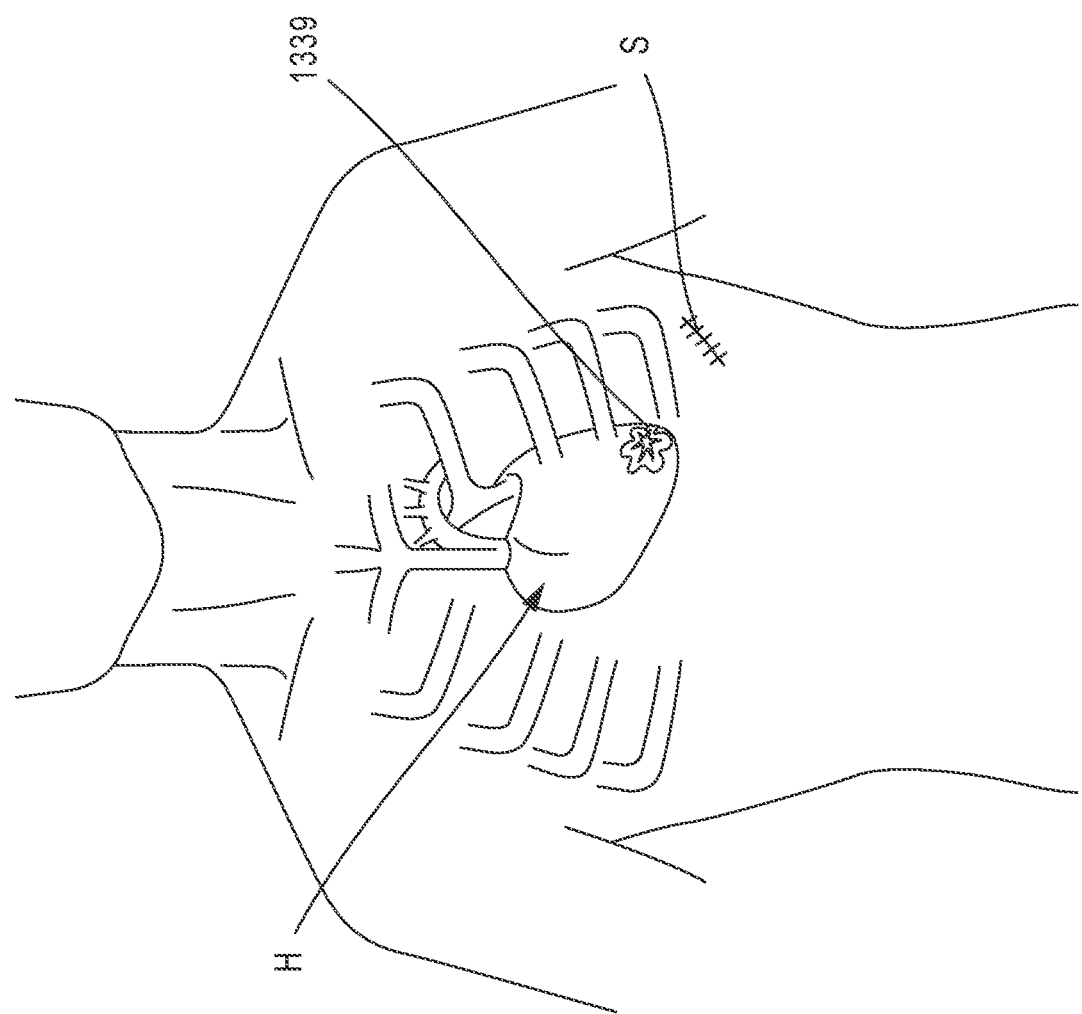
FIG. 52 is an illustration of the epicardial pad device of FIG. 51 delivered and deployed at the apex region of the patient's heart.

Upon delivery and deployment of the epicardial pad 1439 at the apex of the heart H, the delivery sheath 1463, tissue dilator 1476, and stopper tube 1489 can be removed from the patient and the incision can be closed with sutures (similar to above with reference to FIG. 52). The retracting element 1479 can be disengaged from the tissue of the pericardium P. The delivery sheath 1463, the tissue dilator 1476, and the stopper tube 1489 can be removed from the patient's body at the same time or in stages. The epicardial pad 1439 and tether 1436 can be secured in the desired position with, for example, one or more clips or one or more locking pins or by tying the tether 1436.

Figure 57:
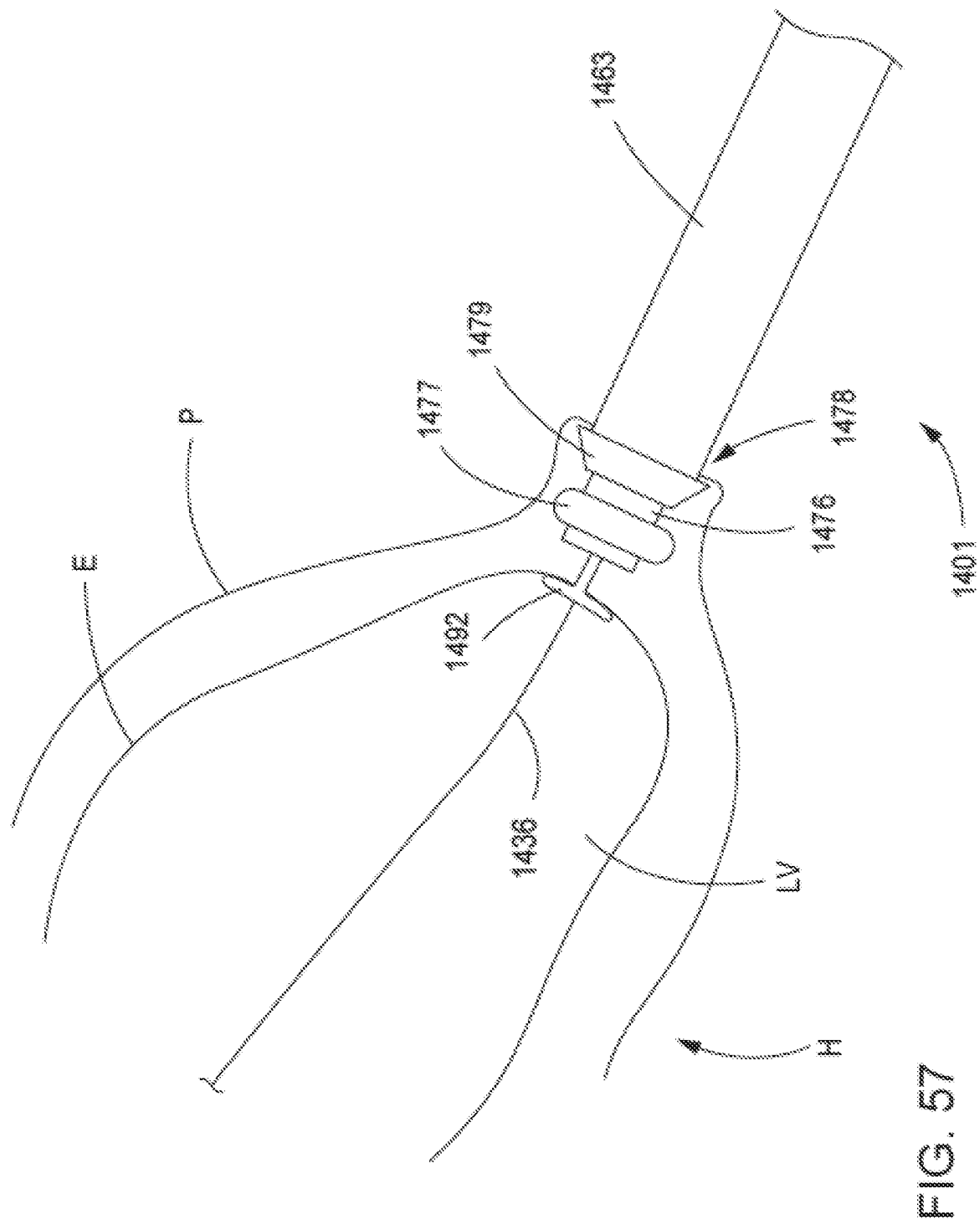
FIG. 57 is a side view illustration of the epicardial pad delivery device of FIG. 53 during another stage of a procedure to deliver an epicardial pad device to the apex region of a patient's heart.
Figure 58:
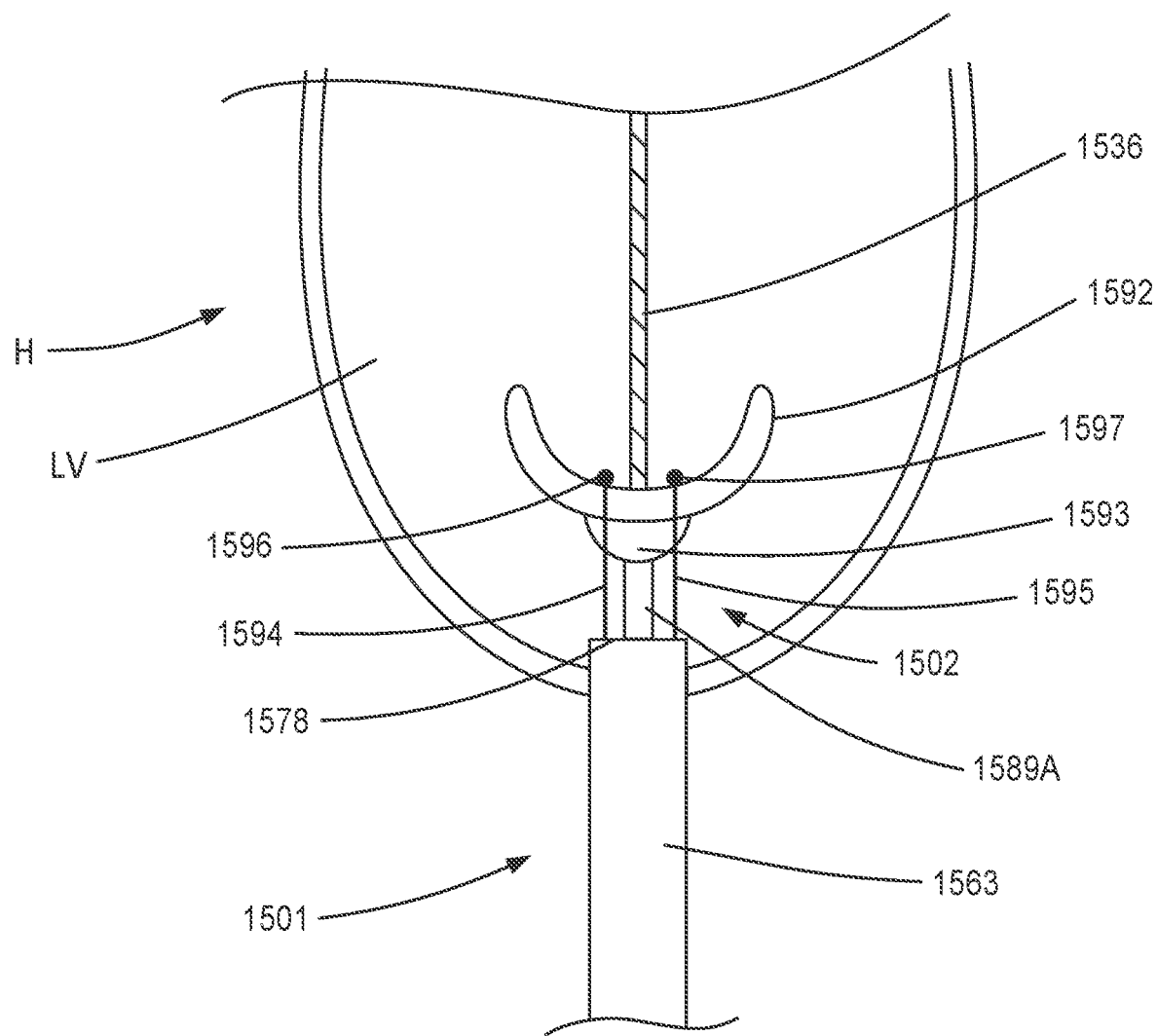
FIG. 58 is a side view illustration of a portion of an epicardial pad assembly and an epicardial pad delivery device, according to an embodiment, during a stage of a procedure to deliver the epicardial pad assembly to the apex region of a patient's heart.

In some embodiments, the delivery device 1401 can include an anchoring member in the form of an internal balloon that can be disposed inside the heart during the delivery of the epicardial pad 1439. For example, FIG. 57 is an illustration of the embodiment of FIGS. 53-56 including an optional expandable anchoring member 1492. The expandable anchoring member 1492 includes an elongate member and a locating balloon on the distal end of the elongate member. The elongate member can define an inflation lumen through which the locating balloon can be expanded (e.g., inflated) with an inflation medium. Said another way, the elongate member can define an inflation lumen that can communicate an inflation medium to and from the locating balloon. Additionally, the elongate member and the locating balloon can define a tether lumen (not shown).

In use, the tether 1436 can be threaded through the tether lumen of the expandable anchoring member 1492. With the locating balloon in an unexpanded configuration, the expandable anchoring member 1492 can be pushed or moved distally through the lumen of the stopper tube 1489 and the epicardial pad 1439. When the delivery device 1401 is positioned in the desired location near the apex of the heart H, the elongate member of the expandable anchoring member 1492 can be pushed distally, pushing the locating balloon through the puncture site in the apex of the heart H through which the tether 1436 extends.

With the locating balloon disposed within the left ventricle LV, the locating balloon can be transitioned from an unexpanded configuration (not shown) to an expanded configuration, as shown in FIG. 57. With the locating balloon in its expanded configuration, the elongate member of the expandable anchoring member 1492 can be pulled proximally. The proximal movement of the elongate member of the expandable anchoring member 1492 pulls the locating balloon toward the apex of the heart H, helping to stabilize the location of the tissue surrounding the puncture site for placement of the epicardial pad 1439. After the epicardial pad 1439 is positioned against the outside of the heart H, the locating balloon can be deflated and withdrawn through the apex of the heart H and the epicardial pad 1439 by pulling proximally on the elongate member of the expandable anchoring member 1492.

FIGS. 58-61 illustrate an embodiment of an expandable epicardial pad assembly. The expandable epicardial pad assembly can be used to secure a tether attached to a prosthetic mitral valve to the heart, for example, at the apex of the heart. An expandable epicardial pad assembly 1502 (also referred to herein as "pad assembly") can be used, for example, during a procedure to deliver a prosthetic heart valve as described herein. The epicardial pad assembly 1502 can be formed with a small profile, or can be moved between a collapsed configuration for delivery in which the pad assembly 1502 has a small profile, and an expanded configuration for deployment/implantation within a patient's body. For example, as described above for previous embodiments, the epicardial pad assembly 1502 can be delivered to the heart H via a delivery device 1501 including a small diameter delivery catheter or sheath 1563 that can be inserted through a small incision in the patient. In some embodiments, the delivery sheath 1563 can have a diameter, for example, in the range of 3-5 mm.

Figure 59:
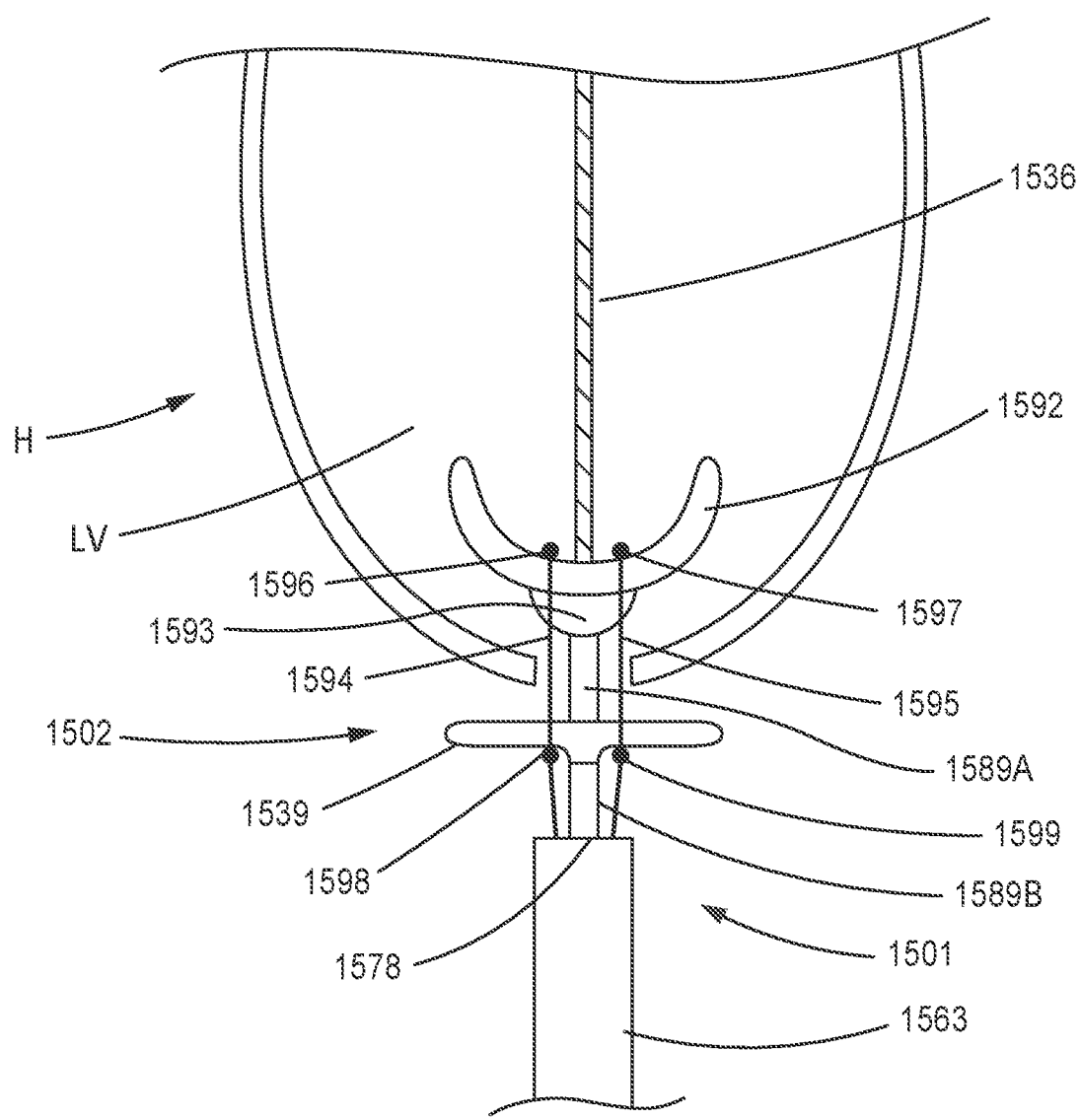
FIG. 59 is a side view illustration of the epicardial pad assembly and the epicardial pad delivery device of FIG. 58 during another stage of a procedure to deliver the epicardial pad assembly to the apex region of a patient's heart.
Figure 60:
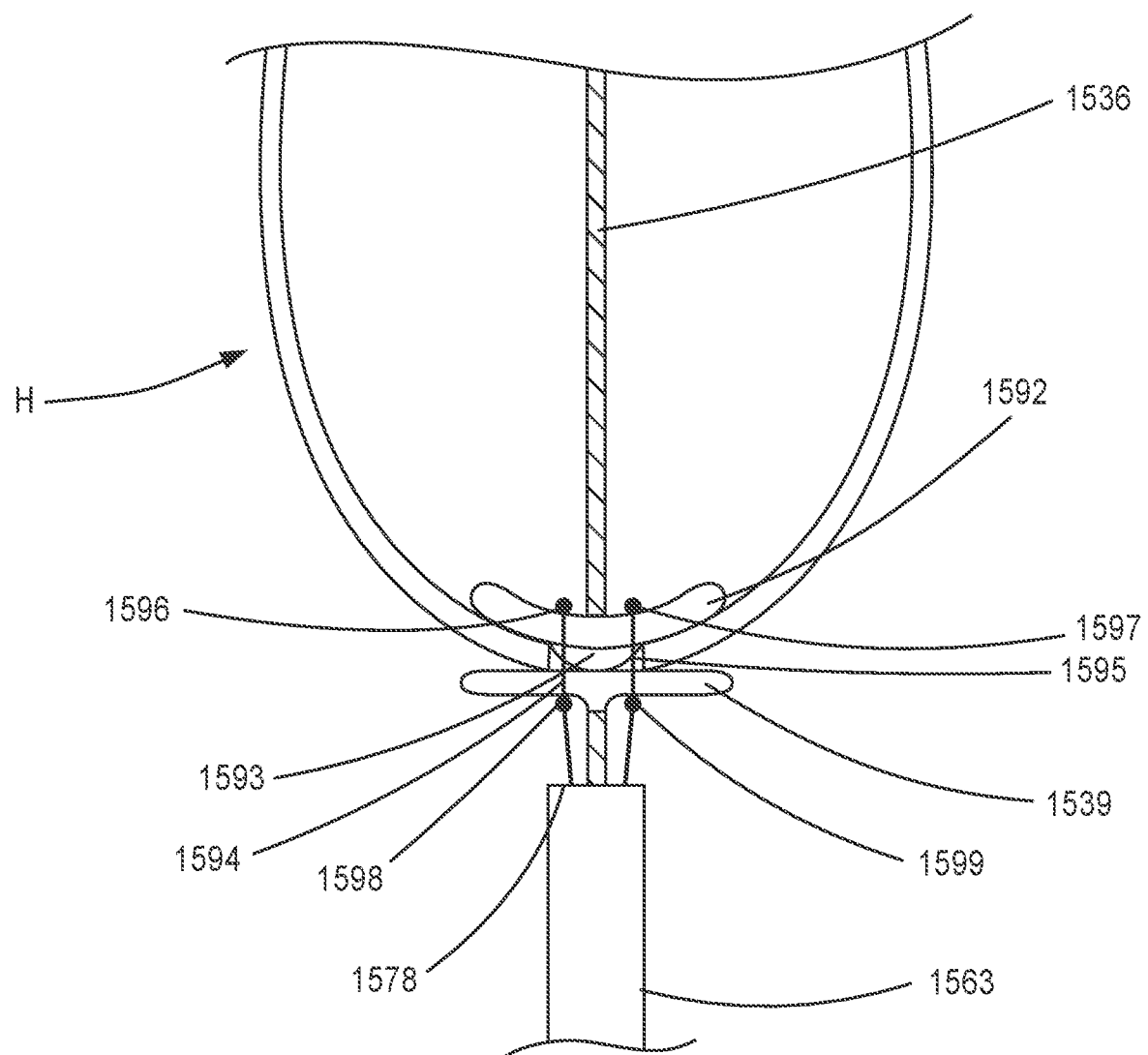
FIG. 60 is a side view illustration of the epicardial pad assembly and the epicardial pad delivery device of FIG. 58 during another stage of a procedure to deliver the epicardial pad assembly to the apex region of a patient's heart.
Figure 61:
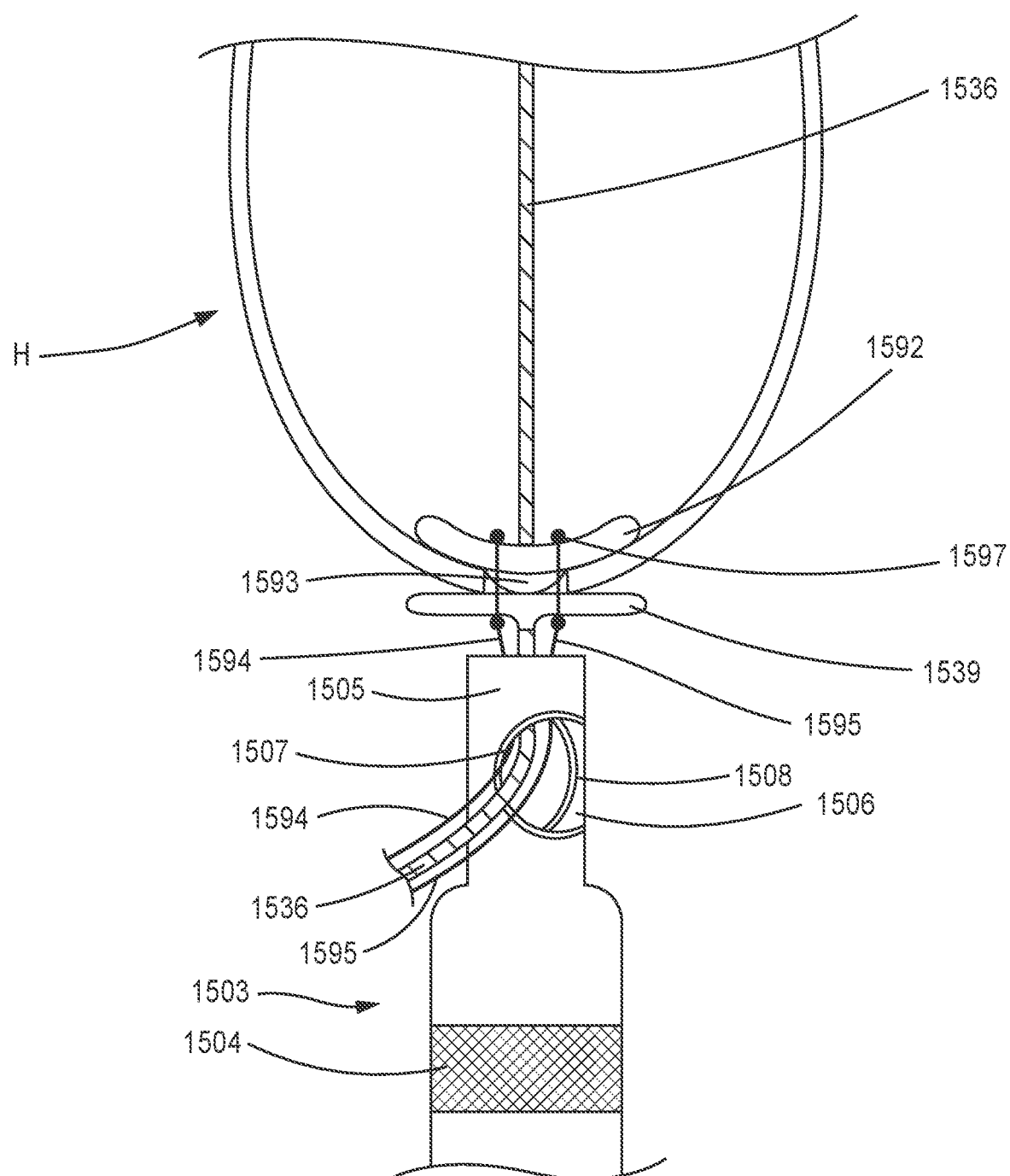
FIG. 61 is an illustration of a cutter assembly, according to an embodiment, used during a stage of a procedure to deliver the epicardial pad assembly of FIGS. 58-60 to the apex region of a patient's heart.

In this embodiment, the pad assembly 1502 can include an inner anchor 1592 and an expandable epicardial pad 1539 (shown in FIGS. 59-61). The inner anchor 1592 includes a protrusion 1593. The protrusion 1593 can be shaped and sized to fill the puncture site in the apex of the heart H through which a tether 1536 coupled to a prosthetic heart valve (not shown) extends. The expandable epicardial pad 1539 can be the same as or similar to any epicardial pad device described herein or in International PCT Application No. PCT/US2014/0049218 (the '218 PCT Application), and can be used in the same or similar manner as described for previous embodiments herein or in the '218 PCT Application to secure a tether attached to a prosthetic mitral valve to the heart, for example, at the apex of the heart. The epicardial pad 1539 can be used to secure the tether 1536 and the prosthetic valve (not shown) in a desired position.

The expandable epicardial pad 1539 and the inner anchor 1592 are attached via a first suture 1594 and a second suture 1595. The first suture 1594 is attached to the inner anchor 1592 via a first suture knot 1596 and the second suture 1595 is attached to the inner anchor 1592 via a second suture knot 1596. The first suture 1594 also includes a third knot 1598 and a fourth knot 1599. The third knot 1598 and the fourth knot 1599 are sliding knots configured to be tightened to secure the expandable epicardial pad 1539 against the heart H as described in more detail below.

In addition to the delivery sheath 1563, the delivery device 1501 includes an inner stopper tube 1589A and an outer stopper tube 1589B. The outer stopper tube 1589B is movably disposed within a lumen of the delivery sheath 1563, and the inner stopper tube 1589A is movably disposed within a lumen of the outer stopper tube 1589A. The inner stopper tube 1589A can define an inner lumen through which the tether 1536 can be inserted. The inner stopper tube 1589A can be coupled to the inner anchor 1592 and control the movement of the inner anchor 1592. For example, the inner stopper tube 1589A can be used to prevent proximal movement of the inner anchor 1592 and to push the inner anchor 1592 distally relative to the delivery sheath 1563 and/or the outer stopper tube 1589B. The inner stopper tube 1589A can be releasably coupled to the inner anchor 1592 such that the inner stopper tube 1589A is secured to the inner anchor 1592 during insertion and/or delivery of the epicardial pad assembly 1501. In other embodiments, the inner stopper tube 1589A is configured to abut a portion of the inner anchor 1592 such that it can limit proximal movement of the inner anchor 1592 and push the inner anchor 1592 distally.

Similarly, the outer stopper tube 1589B can define an inner lumen through which the inner stopper tube 1589A can be inserted. The outer stopper tube 1589B can be coupled to and can control movement of the epicardial pad 1539. For example, the outer stopper tube 1589B can be used to prevent proximal movement of the epicardial pad 1539 and to push the epicardial pad 1539 distally relative to the delivery sheath 1563 and/or the inner stopper tube 1589A. The outer stopper tube 1589B can be releasably coupled to the epicardial pad 1539 such that the outer stopper tube 1589B is secured to the epicardial pad 1539 during insertion and/or delivery of the epicardial pad assembly 1501. In other embodiments, the outer stopper tube 1589B is configured to abut a portion of the epicardial pad 1539 such that it can limit proximal movement of the epicardial pad 1539 and push the epicardial pad 1539 distally.

The inner anchor 1592 can be formed with, for example, suitable medical-grade polymer or metal materials such as, for example, PEEK plastic, or stainless steel such as, for example, MP35N stainless steel. The inner anchor 1592 can also be formed with, for example, purified terephthalic acid (PTA), polylactic acid (PLA), or Nitinol®. In some embodiments, the inner anchor 1592 can be configured to remain in the heart. In other embodiments, the inner anchor 1592 can be formed of a bioabsorbable material or a bioresorbable material such that initially, the inner anchor 1592 can contribute to the stability of the epicardial pad 1539, and after a period of time, the inner anchor 1592 can be absorbed into the body. For example, in some cases, the inner anchor 1592 can be absorbed or at least partially absorbed when ingrowth of the epicardial pad 1539 to the heart has at least partially begun.

In use, after a prosthetic mitral valve has been deployed within the heart H via a transfemoral approach (as described herein), a transapical approach, or another suitable delivery approach, the tether 1536 attached to the prosthetic valve (not shown) can extend outside the apex of the heart H and outside the patient's body via a small incision (similar to incision I as shown above in FIG. 48). The delivery sheath 1563 can be placed over the inner anchor 1592 and the epicardial pad 1539 to collapse the inner anchor 1592 and the epicardial pad 1539 in a similar manner as described above for previous embodiments. A proximal end of the tether 1536 can be threaded into and through a distal end of a lumen of the outer delivery sheath 1563 and through a center opening of the inner anchor 1592 and a center opening of the epicardial pad 1539. In this manner, the tether 1536 can provide a guide or otherwise assist in the insertion and movement of the delivery sheath 1563 through the incision in the skin of the patient. A distal end 1578 of the delivery sheath 1563 can be moved along the tether 1536 and disposed at a desired location near the apex of the heart H. The distal end 1578 of the delivery sheath 1563 can then be inserted through the apex of the heart H such that the distal end 1578 is positioned in the left ventricle LV. Alternatively, the tether 1536 can be threaded into the delivery sheath 1563 and the delivery sheath 1563 can be positioned in the left ventricle LV prior to the pad assembly 1502 being inserted into the lumen of the delivery sheath 1563. In such a case, the inner anchor 1592 and epicardial pad 1539 can be moved at least partially through the distal end 1578 of the delivery sheath 1563 via the inner stopper tube 1589A and the outer stopper tube 1589B, respectively.

With the distal end 1578 of the delivery sheath 1563 positioned in the left ventricle LV, the inner anchor 1592 can be extended outside the distal end of the lumen of the delivery sheath 1563 and moved to its expanded configuration in the left ventricle LV, as shown in FIG. 59. For example, to move the inner anchor 1592 outside of the lumen of the delivery sheath 1563, the delivery sheath 1563 can be moved proximally relative to the inner stopper tube 1589A, such that the delivery sheath 1563 is removed from the inner anchor 1592. Alternatively or additionally, the inner anchor 1592 can be pushed distally via a distal movement of the inner stopper tube 1589A such that the inner anchor 1592 is moved outside of the lumen of the delivery sheath 1563.

When the inner anchor 1592 is positioned in the left ventricle LV, the delivery sheath 1563 can be moved proximally such that the delivery sheath 1563 is withdrawn from the left ventricle LV through the apex of the heart H. As shown in FIG. 60, when the distal end 1578 of the delivery sheath 1563 is at the desired location near the apex of the heart H outside of the left ventricle LV, the epicardial pad 1539 can be moved outside the distal end 1578 of the delivery sheath 1563 such that the epicardial pad 1539 can assume a biased expanded configuration, similar to, for example, the epicardial pad 936 described above, or can be moved to an expanded configuration as described above for epicardial pad 1139. For example, to move the epicardial pad 1539 outside of the lumen of the delivery sheath 1563, the delivery sheath 1563 can be moved proximally relative to the outer stopper tube 1589B, such that the delivery sheath 1563 is removed from the epicardial pad 1539. Alternatively, the epicardial pad 1539 can be pushed distally via a distal movement of the outer stopper tube 1589B such that the epicardial pad 1539 is moved outside of the lumen of the delivery sheath 1563.

As shown in FIG. 60, after the epicardial pad 1539 has moved to its expanded configuration, the third knot 1598 and the fourth knot 1599 can be slid distally along the first suture 1594 and the second suture 1595, respectively, to secure the epicardial pad 1539 and the inner anchor 1592 in position. In some embodiments, the third knot 1598 and the fourth knot 1599 can be tightened against the epicardial pad 1539 by pulling on the first suture 1594 and the second suture 1595. In other embodiments, the delivery assembly 1501 can include a first suture tube (not shown) and a second suture tube (not shown). The first suture 1594 can be threaded through the first suture tube and the second suture 1595 can be threaded through the second suture tube. The first suture tube and the second suture tube can be slid along the first suture 1594 and the second suture 1595, respectively, to push the third knot 1598 and the fourth knot 1599 against the epicardial pad 1539 to secure the epicardial pad 1539 and the inner anchor 1592 against the apex of the heart H.

Upon delivery and deployment of the epicardial pad 1539 at the apex of the heart H, the delivery sheath 1563, the inner stopper tube 1589A and the outer stopper tube 1589B can be removed from the patient. The epicardial pad 1539 and tether 1536 can be secured in the desired position with, for example, clip(s) or a locking pin(s) or by tying the tether 1536.

FIG. 61 is an illustration of a cutting assembly 1503 that can optionally be used to cut or sever the tether 1536, the first suture 1594, and/or the second suture 1595. The cutting assembly 1503 includes an outer tube 1505, an inner tube 1506, and a rotational knob 1504. The outer tube 1505 and the inner tube 1506 each define a distal end opening and a side opening. A first sharp edge 1507 surrounds the side opening of the outer tube 1505 and a second sharp edge 1508 surrounds the side opening of the inner tube 1506. The outer tube 1505 and the inner tube 1506 are arranged such that the inner tube 1506 is movably disposed within the outer tube 1505. For example, the inner tube 1506 can be rotationally movable relative to the outer tube 1505 and vice versa. Additionally, the distal end opening of the inner tube 1506 and the distal end opening of the outer tube 1505 can be coaxial.

In use, the side openings of the outer tube 1505 and the inner tube 1506 can be aligned such that the side openings at least partially overlap to collectively define an opening between the first sharp edge 1507 and the second sharp edge 1508. The tether 1536, the first suture 1594, and the second suture 1595 can be inserted through the distal end opening in the inner tube 1506 and threaded through the combined opening defined between the first sharp edge 1507 and the second sharp edge 1508. The rotational knob 1504 can rotate the inner tube 1506 relative to the outer tube 1507 (or vice versa) such that the second sharp edge 1508 rotates toward the first sharp edge 1507 and pinches the tether 1536, the first suture 1594, and/or the second suture 1595 between the first sharp edge 1507 and the second sharp edge 1508. The inner tube 1506 and the outer tube 1507 can be further rotated relative to each other such that the first sharp edge 1507 and the second sharp edge 1508 cut the tether 1536, the first suture 1594, and/or the second suture 1595.

In some embodiments, the cutting assembly 1503 can be used to cut the tether 1536 at a first time and be used to cut the first suture 1594 and/or the second suture 1595 at a second time before or after the first time. In other embodiments, the cutting assembly 1503 can be used to cut the tether 1536, the first suture 1594, and the second suture 1595 in one motion. In some embodiments, a first cutting assembly can be used to cut the tether 1536 and a second cutting assembly can be used to cut the first suture 1594 and/or the second suture 1595. The first cutting assembly can be a different size than the second cutting assembly depending on the size of the tether 1536, the first suture 1594 and/or the second suture 1595. In still other embodiments, the tether 1536, the first suture 1594 and/or the second suture 1595 can be trimmed using scissors, cauterization, or any other suitable cutting methods. Additionally, in some embodiments, the cutting assembly 1503 can be used to slide the third knot 1598 and the fourth knot 1599 distally along the first suture 1594 and the second suture 1595, respectively, to secure the epicardial pad 1539 and the inner anchor 1592 against the apex of the heart H.

Figure 62:
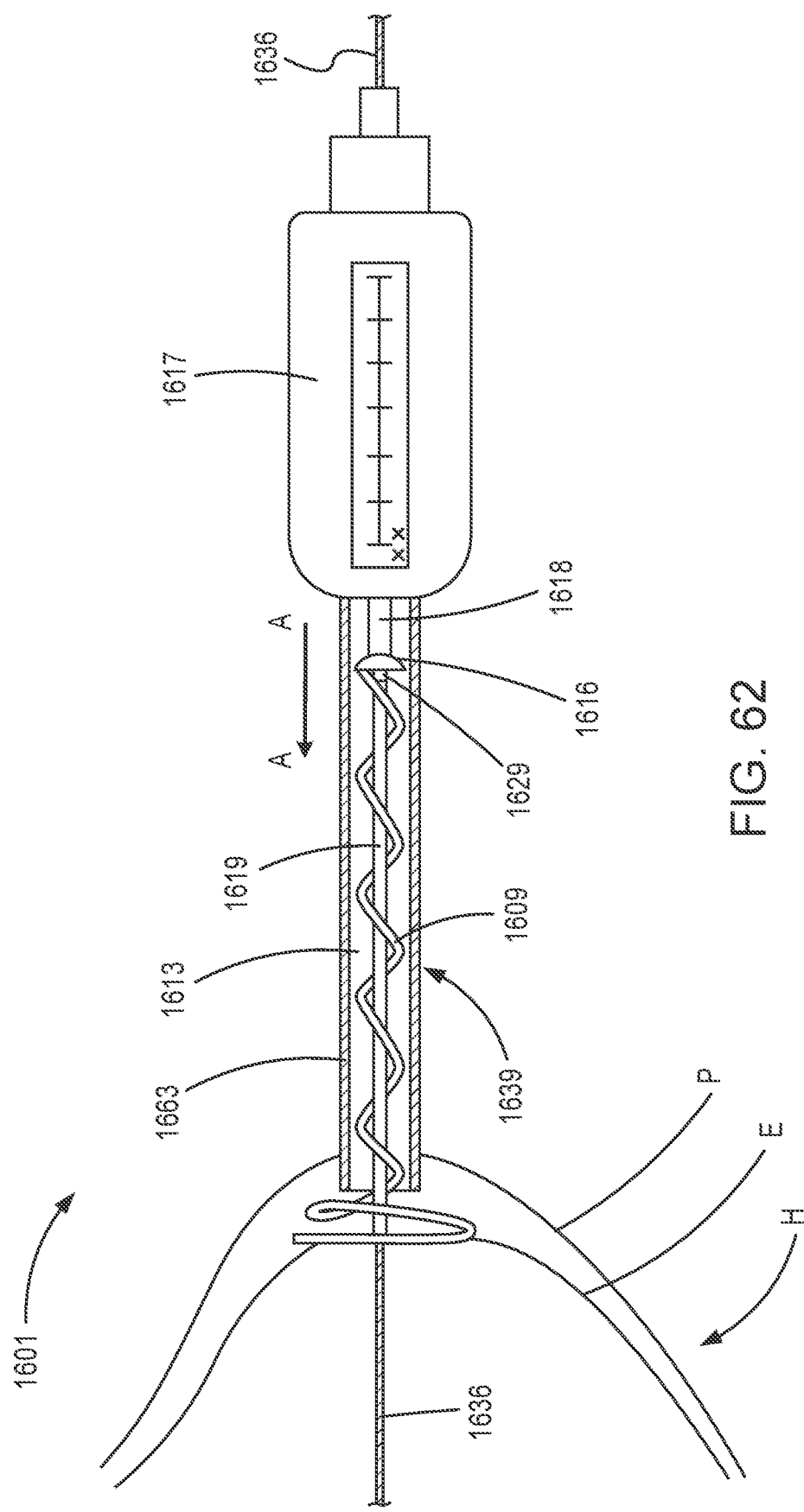
FIG. 62 is a side view illustration shown partially in cross-section of an epicardial pad assembly and an epicardial pad delivery device, according to an embodiment, during a stage of a procedure to deliver the epicardial pad assembly to the apex region of a patient's heart.
Figure 64:
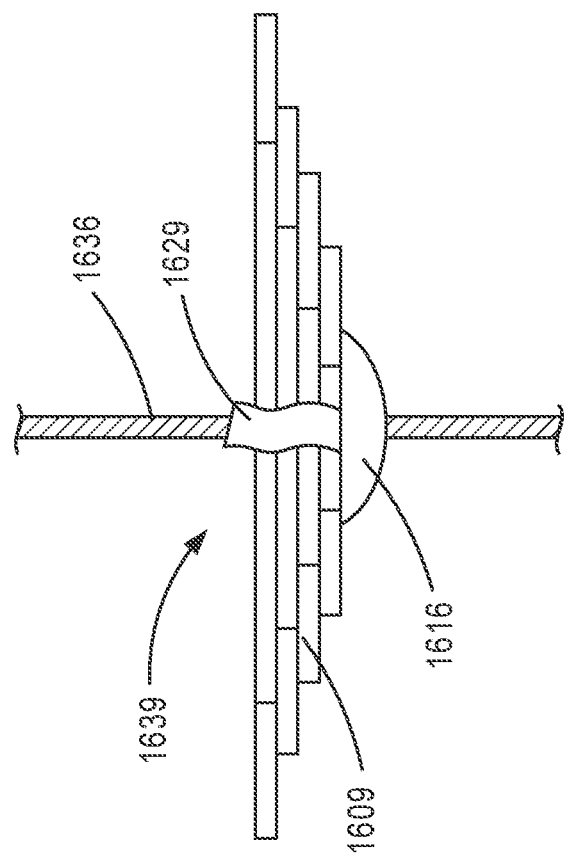
FIG. 64 is a side view illustration of the epicardial pad assembly of FIG. 62 in a collapsed configuration.
Figure 63:
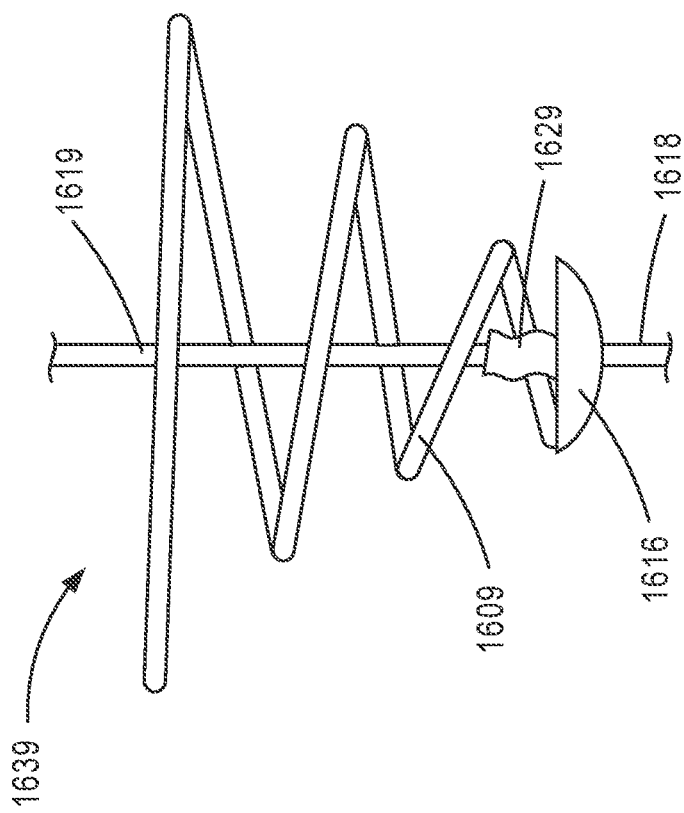
FIG. 63 is a side view illustration of the epicardial pad assembly of FIG. 62 in an expanded configuration.

FIGS. 62-64 illustrate another embodiment of an expandable epicardial pad delivery device that can be used to deliver an expandable epicardial pad. The expandable epicardial pad can be used to secure a tether attached to a prosthetic mitral valve to the heart, for example, at the apex of the heart. An expandable epicardial pad delivery device 1601 (also referred to herein as "pad delivery device" or "delivery device") can be used, for example, during a procedure to deliver a prosthetic heart valve as described herein. The delivery device 1601 can be used to deliver an expandable epicardial pad 1639. The expandable epicardial pad 1639 includes a spiral member 1609 and a locking member 1616 at a proximal end portion of the spiral member 1609. The spiral member 1609 can be formed such that the spiral member 1609 can have a small profile for delivery of the spiral member 1609 within a delivery sheath of the delivery device 1601. The delivery device 1601 can include an outer delivery sheath 1663 that has a small outer diameter such that the epicardial pad 1639 can be delivered within the delivery device 1601 to the exterior of the heart via a small incision. The delivery device 1601 also includes an inner tube 1619, and a handle assembly 1617. The delivery device 1601 can also include a push rod 1618 to control the location of the locking member 1616 relative to the inner tube 1619 and outer delivery sheath 1663.

The outer delivery sheath 1663 extends from the handle 1617 and defines a lumen 1613. The outer delivery sheath 1663 can have an outer diameter, for example, in the range of 3-5 mm. The inner tube 1619 can be moveably disposed within the lumen 1613 of the outer delivery sheath 1663. The inner tube 1619 defines a lumen (not shown) configured to receive a portion of the tether 1636. The push rod 1618 can be movably disposed within the lumen 1613 such that the push rod 1618 can control the movement of the locking member 1616 and the spiral member 1609. For example, the push rod 1618 can be used to push the locking member 1616 until most or all of the spiral member 1609 and/or the locking member 1616 has been pushed out of the distal end of the outer delivery sheath 1663.

The spiral member 1609 is configured to be manipulated and/or deformed (e.g., compressed and/or expanded) and, when released, return to its original (undeformed) shape. To achieve this, the spiral member 1609 can be formed of various materials, such as biocompatible metals or plastics, that have shape memory properties. For example, the spiral member 1609 can be formed with, for example, a suitable polymer, such as, for example, PEEK plastic. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used. The spiral member 1609 can also optionally be covered at least in part with a polyester material to promote ingrowth.

The spiral member 1609 can be moved from a first configuration when the spiral member 1609 is disposed within the outer delivery sheath 1663 to a second, expanded configuration when the spiral member 1609 is unconstrained (e.g., outside the lumen of the delivery sheath 1663). In the first configuration, the spiral member 1609 is radially compressed and placed into an elongated, stretched shape within the lumen 1613 of the outer delivery sheath 1663 as partially shown in FIG. 62. For example, the spiral member 1609 may be shaped as an elongated spiral or coil. In the second, expanded configuration, as shown in FIG. 63, the coils of the spiral member 1609 are unconstrained by the delivery sheath 1663 and collectively have a larger diameter than when in the first configuration. The spiral member 1609 can then be moved to a third configuration in which the spiral member 1609 is compressed axially such that the coils of the spiral member 1609 are collapsed upon each other and form a collapsed, flattened spiral shape (as shown in FIG. 64).

In some embodiments, the spiral member 1609 can be biased toward the second expanded configuration shown in FIG. 63. The spiral member 1609 can then be moved by the locking member 1616 into the third configuration of FIG. 64. In other embodiments, the spiral member 1609 can be biased toward the third configuration shown in FIG. 64 such that the spiral member 1609 automatically moves into the third configuration after being moved outside the distal end of the outer delivery sheath 1663.

The locking member 1616 can include a collapsible sock portion 1629 that can be used to lock the spiral member 1609 in the third configuration as described in more detail below. More specifically, the locking member 1616 can define a lumen (not shown) configured to receive the inner tube 1619 such that the locking member 1616 can move distally along the inner tube 1619 as the push rod 1618 pushes the locking member 1616 distally relative to the outer delivery sheath 1663. Additionally, the push rod 1618 can define a lumen configured to receive the inner tube 1619 such that the push rod 1618 can travel over the inner tube 1619 as the push rod 1618 pushes the locking member 1616 and the spiral member 1609 distally through the outer delivery sheath 1663. The sock portion 1629 can be formed of, for example, a mesh or fabric material. The sock portion 1629 can be, for example, a Dacron sock. The sock portion 1629 is tubular shaped and can be moved from a first configuration during delivery of the epicardial pad 1639 in which the sock portion 1629 has a first length, to a second configuration in which the sock portion 1629 is at least partially collapsed upon itself and has a second shorter length than the first length. In the second configuration, the sock portion 1629 can engage at least some of the coils of the spiral member 1609 to maintain the spiral member 1609 in the third configuration (as shown in FIG. 64). Further, the material of the sock portion 1629 can maintain the sock portion 1629 in its second, collapsed configuration.

As described above for previous embodiments, a tether locking mechanism (not shown) can be used to lock the tether 1636 to the epicardial pad 1639. For example, when the tether 1636 is taut (e.g., when a desired tension on the tether has been achieved), the tether locking mechanism can be configured to pin or lock the tether 1636 to the epicardial pad 1639. In some embodiments, the tether locking mechanism can be incorporated into the locking member 1616. Alternatively, the delivery device 1601 can include an extension element (not shown). The tether 1636 can be extended through the extension element. The extension element can be, for example, a tube, coil, or spring. The extension element can abut the locking member 1616 on the side of the locking member 1616 opposite the spiral member 1609 and extend proximally from the locking member 1616. The tether locking mechanism can be located on the proximal end of the extension element. In embodiments including the extension element, the tether locking mechanism can be located close to the skin of the patient after delivery of the spiral member 1609, providing easier access to the tether locking mechanism if a user (e.g., physician) desires to release the tether and remove the spiral member 1609 from the patient.

In some embodiments, the delivery device 1601 includes an inner delivery sheath (not shown). The spiral member 1609 in the first configuration can be movably disposed within the inner delivery sheath. The inner delivery sheath can be moved distally relative to the outer delivery sheath 1663 by rotating the inner delivery sheath such that the distal end of the inner delivery sheath extends beyond the distal end of the outer delivery sheath 1663. The rotation of the inner delivery sheath can assist in shaping the spiral member 1609 as it is being moved to the second and/or third configuration.

As shown in FIG. 62, the handle assembly 1617 can include a window with a scale. The window can be used to view the tether 1636. For example, the tether 1636 can extend through the handle assembly 1617 and include markings (not shown). For example, in some embodiments, the inner tube 1619 can be clear or transparent and extend through the handle assembly 1617 such that the markings on the tether 1636 are visible through the inner tube 1619. In some embodiments, the inner tube 1619 can include markings that are viewable through the window of the handle assembly 1617. The markings can be used to indicate the tautness or length of the tether 1636. The user can view the markings through the window to determine a condition of the tether 1636, such as the tautness. In some embodiments, the handle assembly 1617 can also include a tether locking device, such as for example a locking pin or vise type mechanism that can be used to hold the tether 1636 to the handle assembly 1617 during the delivery procedure. The handle assembly 1617 can also include a mechanism that can be used to increase or decrease the tension on the tether 1636.

In use, after a prosthetic mitral valve has been deployed within the heart H via a transfemoral approach (as described herein), a transapical approach, or another suitable delivery approach, the tether 1636 attached to the prosthetic valve (not shown) can extend outside the apex of the heart H and outside the patient's body via a small incision (similar to incision I as shown above in FIG. 48). The epicardial pad 1639 can be loaded into the outer delivery sheath 1663 to place the spiral member 1609 in the first configuration. A proximal end of the tether 1636 can be threaded into and through a distal end of the lumen of the inner tube 1619. The tether 1636 and the inner tube 1619 can then be threaded through the lumen 1613 of the outer delivery sheath 1663, through the center opening of the locking member 1616, and through the lumen of the stopper tube 1618. In this manner, the tether 1636 can provide a guide or otherwise assist in the insertion and movement of the outer delivery sheath 1663 through the incision in the skin of the patient. A distal end of the delivery sheath 1663 and a distal end of the inner tube 1619 can be moved along the tether 1636 and disposed at a desired location near the apex of the heart H. The distal end of the outer delivery sheath 1663 can be inserted through the apex of the heart H such that the distal end is positioned between the epicardium E and the pericardium P of the heart H.

When positioned between the epicardium E and the pericardium P, the distal end of the delivery sheath 1663 can be pulled proximally slightly to make room for the delivery of the epicardial pad 1639 (as shown in FIG. 62). The stopper tube 1618 can then be moved relative to the outer delivery sheath 1663 to move the locking member 1616 distally relative to the outer delivery sheath 1663, causing the locking member 1616 to move a portion of the spiral member 1609 out of the distal end of the outer delivery sheath 1663. For example, the stopper tube 1618 can be moved distally along arrow AA relative to the outer delivery sheath 1663, pushing the locking member 1616 and the spiral member 1609 distally. Alternatively, the outer delivery sheath 1663 can be pulled proximally relative to the stopper tube 1618 such that the distal end of the spiral member 1609 is released from the outer delivery sheath 1663.

After the stopper tube 1618 has pushed the epicardial pad 1639 far enough distally, the spiral member 1609 can transition to its second configuration outside the apex of the heart H, as shown in FIG. 63. The inner tube 1619 can then be retracted and the locking member 1616 can be pushed distally by the stopper tube 1618 such that the spiral member 1609 is moved into the third configuration (as shown in FIG. 64), against the apex of the heart H. To secure the spiral member 1609 in its third configuration, the locking member 1616 can be moved to its second configuration (e.g., collapsed upon itself) to engage the coils of the spiral member 1609 as described above. The tether 1636 can be pulled taut (or to a desired tension) and secured to the epicardial pad 1639. For example, one or more clips or one or more locking pins associated with the locking member 1616 can be used to secure the locking member 1616 to the tether 1636. Alternatively, the tether 1636 can be tied such that the spiral member 1609 and the locking member 1616 are secured against the apex of the heart H. The stopper tube 1618 can then be disengaged from the locking member 1616 and retracted. In embodiments where the spiral member 1609 is biased towards the collapsed configuration, the stopper tube 1618 can be retracted prior to securing the spiral member 1609 and the tether 1636 in position relative to the tether 1636.

Figure 65:
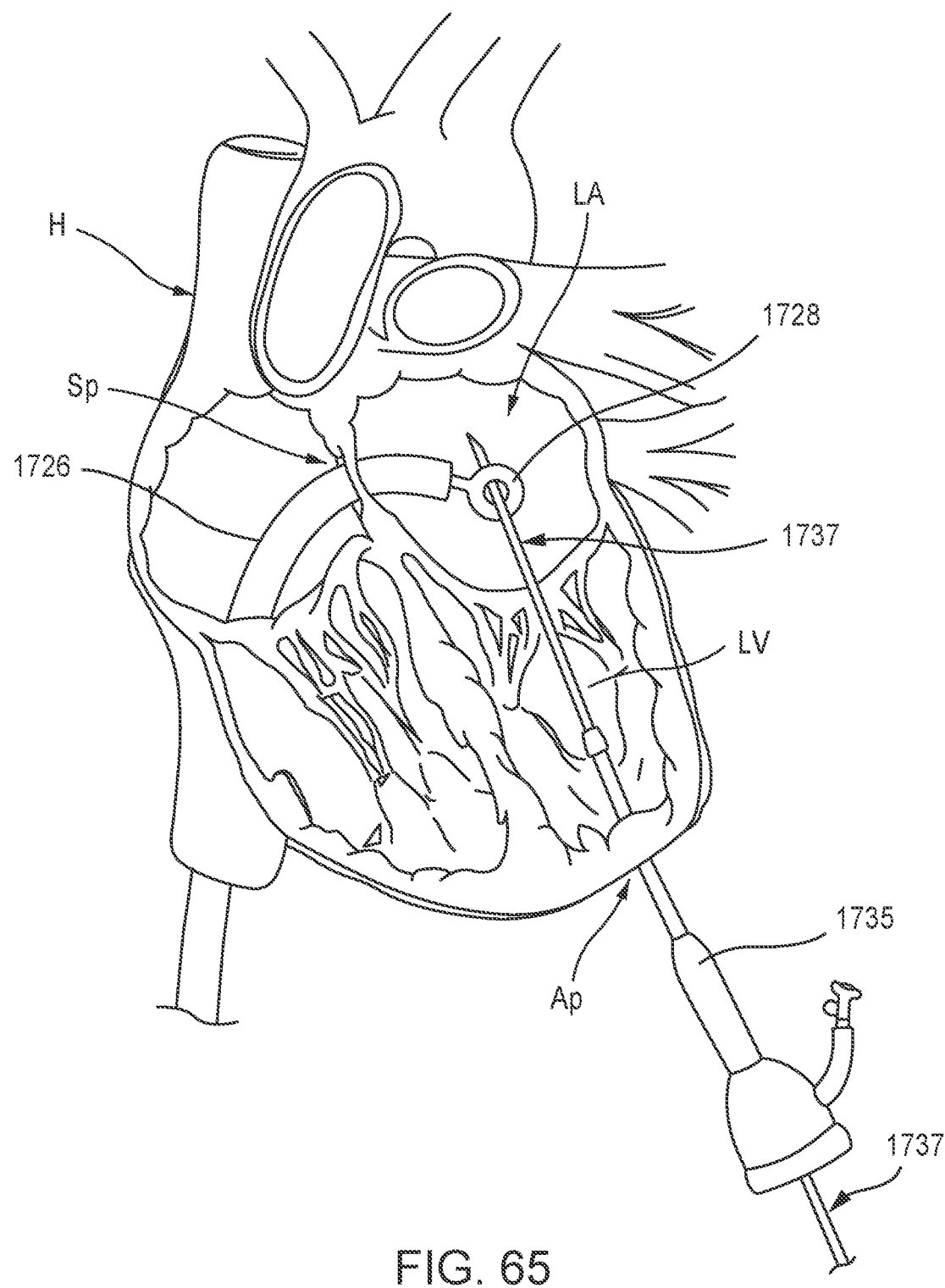
FIGS. 65-70 are each a cross-sectional illustration of a heart with devices used during various stages in a procedure to transfemorally deliver and deploy a prosthetic mitral valve.
Figure 66:
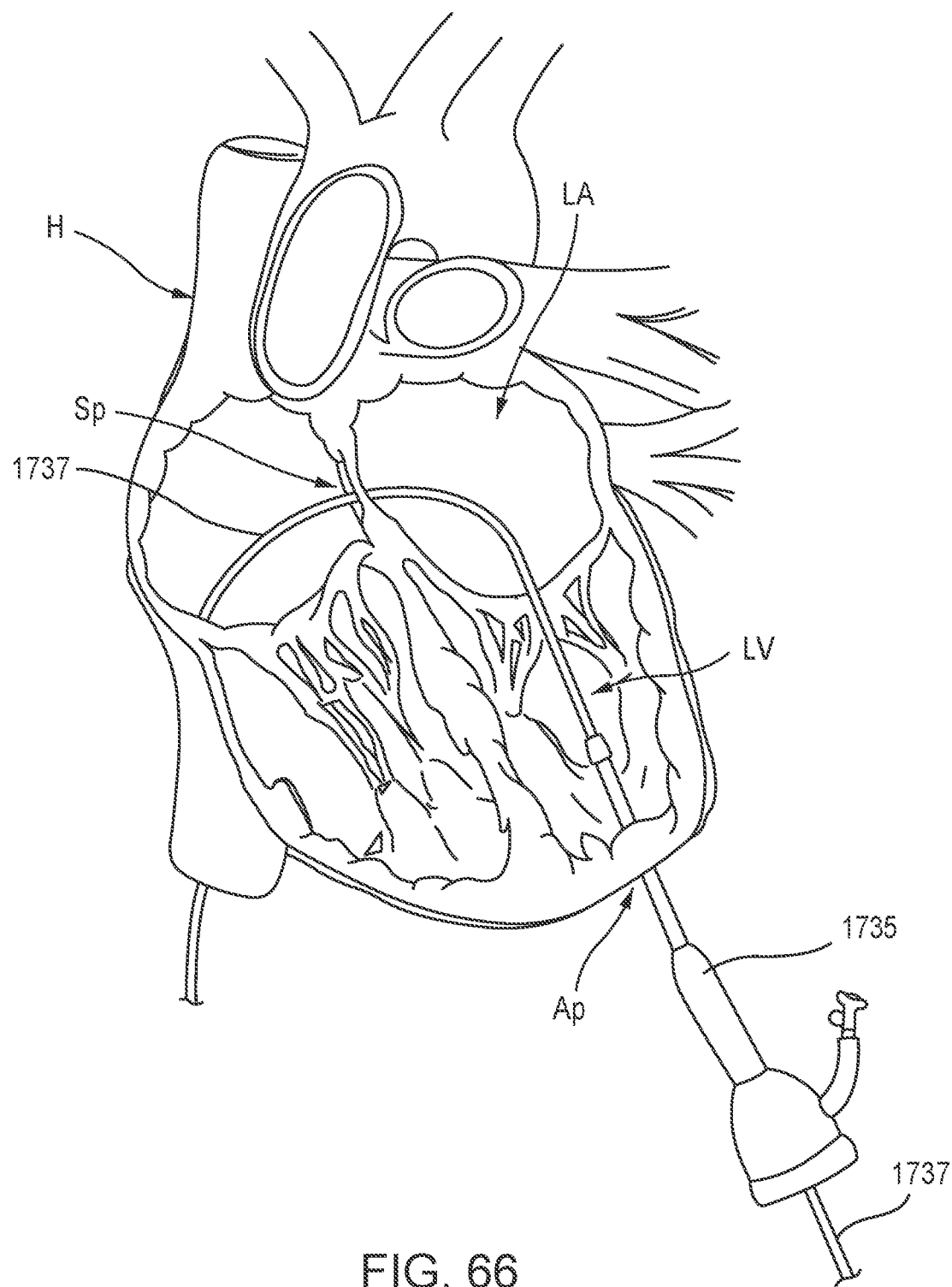
Figure 67:
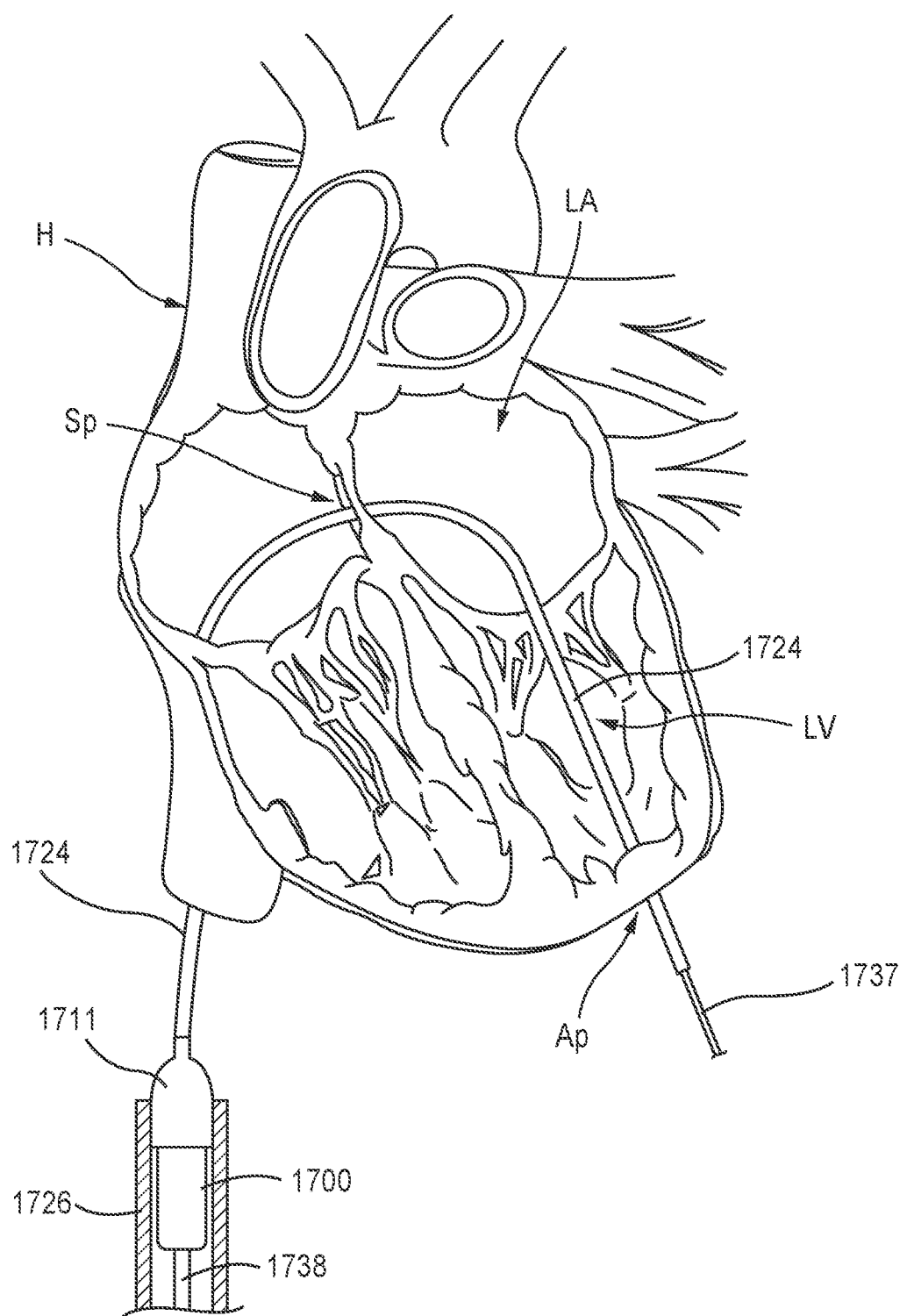
Figure 68:
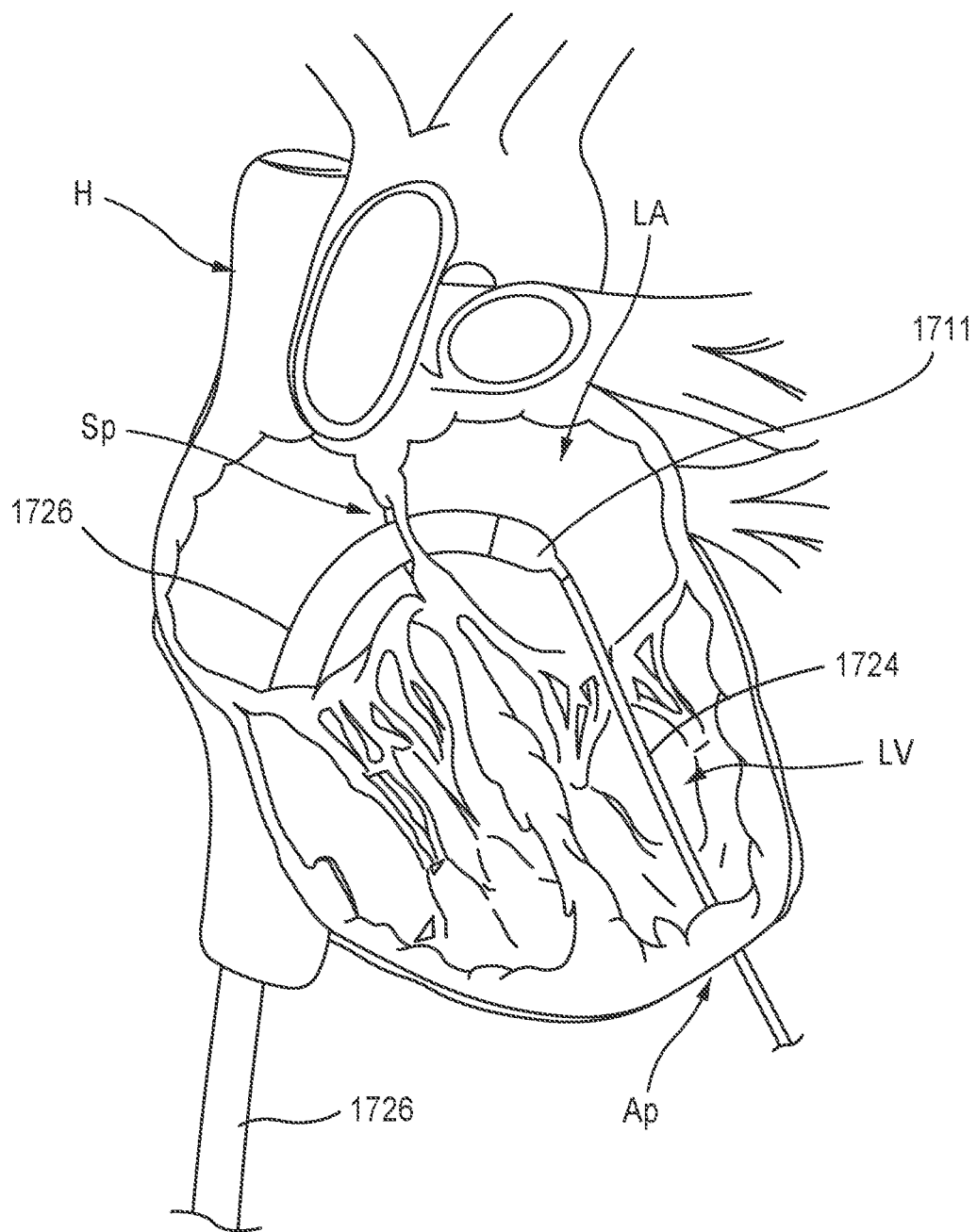
Figure 69:
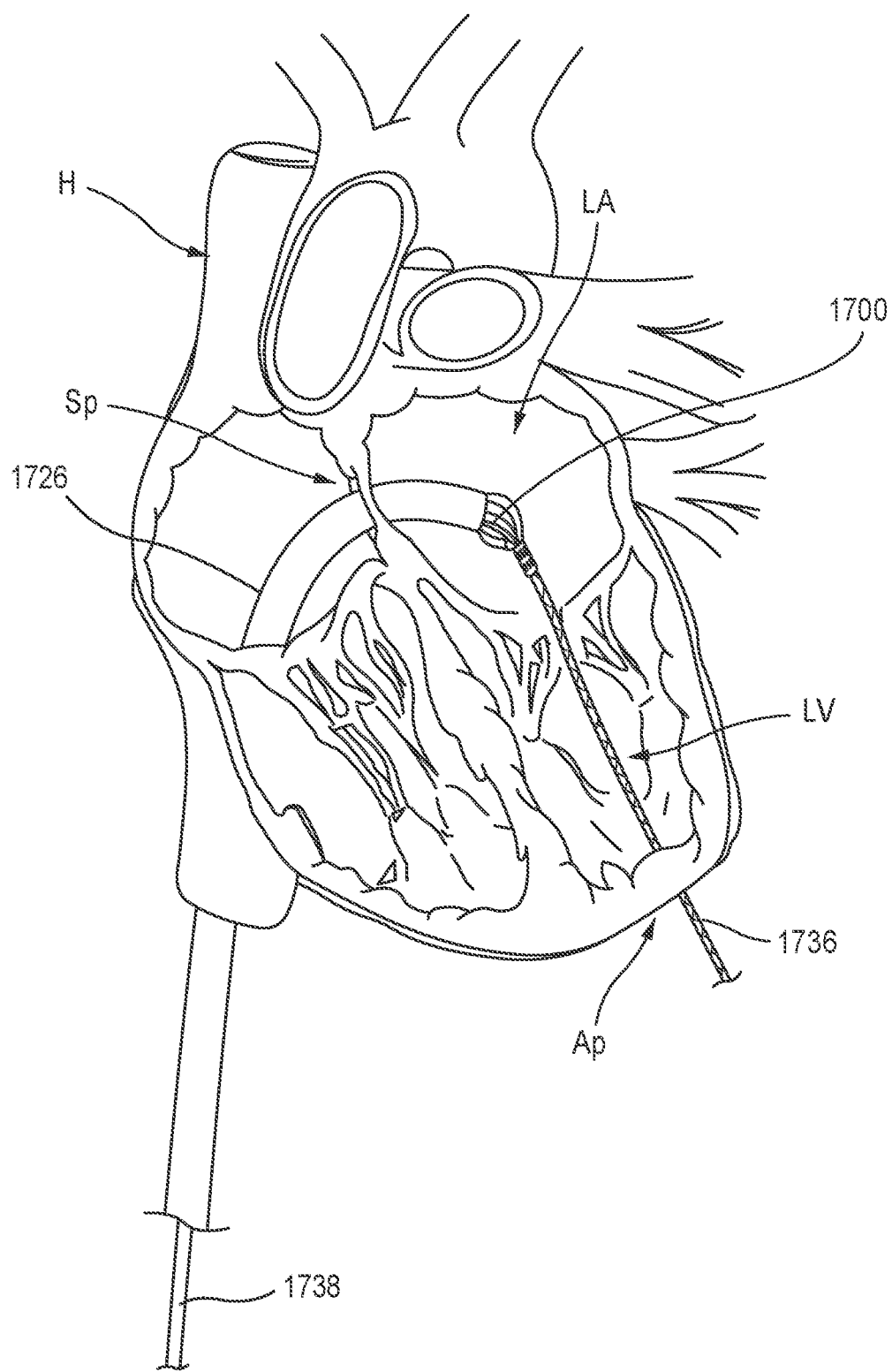
Figure 70:
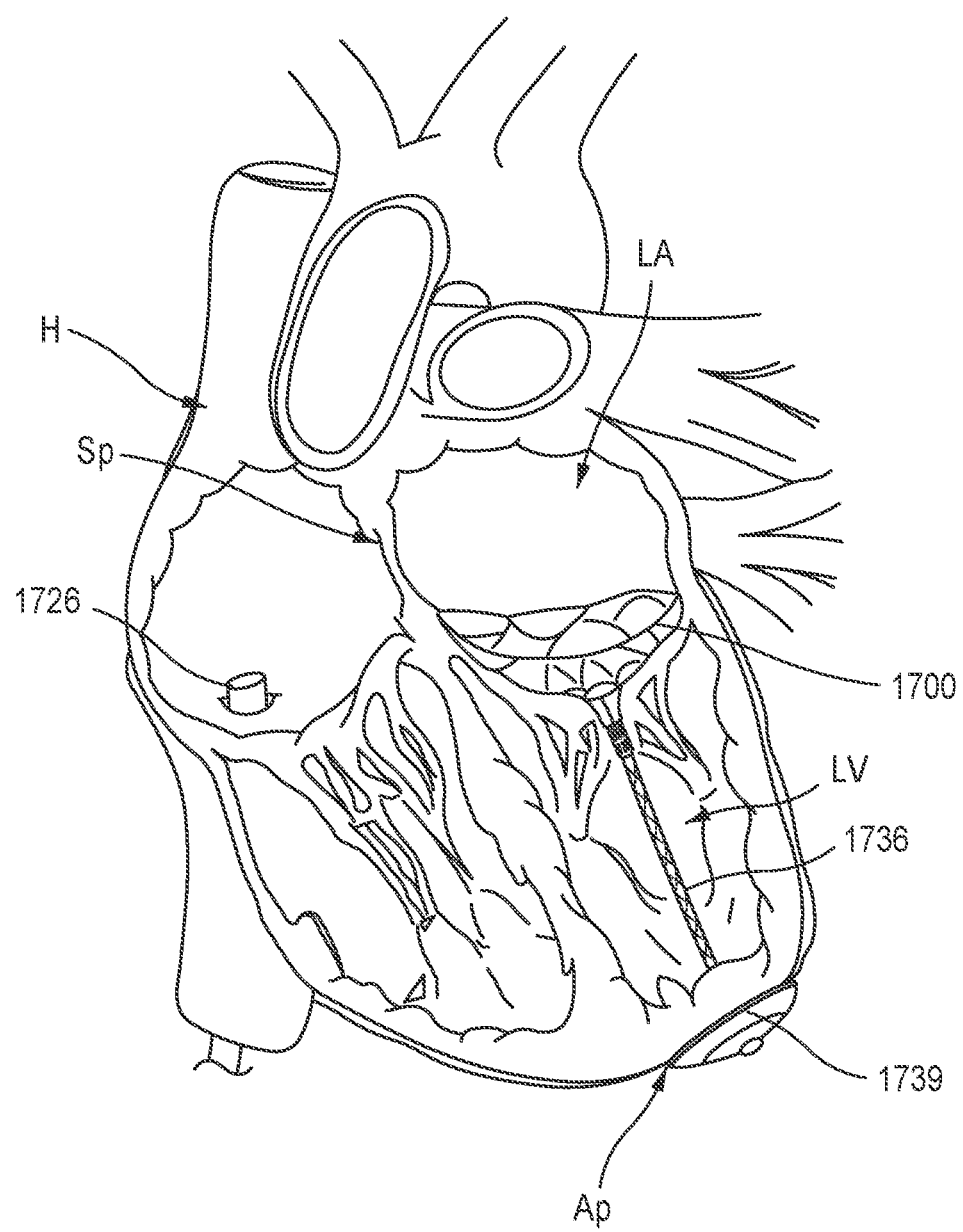

FIGS. 65-70 illustrate an alternative method of delivering a prosthetic valve within an annulus of a heart via a transfemoral delivery approach. As shown in FIG. 65, a procedural catheter 1735 is inserted through an apical puncture (e.g., a 5F apical puncture) in a ventricular wall at the apex Ap of the heart H. A guide wire 1737 is inserted through a lumen (not shown) of the procedural catheter 1735 and extended through the left ventricle LV, through a mitral valve gap and into the left atrium LA. A delivery sheath 1726 is introduced through a femoral vein puncture and extended through the inferior vena cava, into the right atrium, and then through a transseptal puncture of the septum Sp of the heart H, and into the left atrium LA of the heart H. A snare device 1728 is movably disposed within the delivery sheath 1726 and used to grab or snare a distal end portion of the guide wire 1737, as shown in FIG. 65. The snare device 1728 can be used to pull the guide wire 1737 through the delivery sheath 1726 such that the distal end portion of the guide wire 1737 extends outside the femoral vein and a proximal end of the guide wire 1737 is disposed through the ventricular wall at the apex Ap of the heart H, as shown in FIG. 44. Although not shown in FIGS. 43 and 44, the procedural catheter 1735 is disposed outside the patient's body, the distal end of the guide wire 1737 extends outside the femoral vein and outside the patient's body, and the proximal end of the guide wire 1737 extends outside the apex Ap and outside the patient's body. Although the above described snare process describes delivering the guide wire 1737 to the left atrium of the heart and then snaring the guide wire 1737 using the snare device 1728, in alternative embodiments, the guide wire 1737 can be delivered to the left ventricle LV and the snare device 1728 and delivery sheath 1726 can be inserted through the mitral annulus and into the left ventricle LV to grab or snare the guide wire 1737 as described above.

After the guide wire 1737 has been extended between the apex Ap and the access site to the femoral vein, the delivery sheath 1726 can be removed. A leader tube 1724 is loaded over the guide wire 1737 starting outside the heart (and outside the procedural catheter 1735) and exiting the femoral vein at the femoral puncture site as shown in FIG. 45. As shown in FIG. 45, the leader tube 1724 includes a balloon dilator member 1711 that is inserted into a distal end of the delivery sheath 1726 and disposed partially over a distal end portion of the prosthetic valve 1700. For example, the balloon dilator member 1711 can have a collapsed or uninflated configuration (not shown) for delivery over the guide wire 1737 and can then be inflated or otherwise moved to an expanded configuration as shown in FIG. 45. Also shown in FIG. 45, a pusher 1738 is disposed within the lumen of the delivery sheath 1726 and can be used to move or push the prosthetic valve 1700 into the left atrium LA, as described in more detail below. With the leader tube 1724 disposed between the femoral puncture site and the apex of the heart, the guide wire 1737 can be removed. Although not shown in FIGS. 45-47, the procedural catheter 1735 remains inserted into the left ventricle LV of the heart as shown in FIGS. 43 and 44.

The prosthetic valve 1700 can be configured the same as or similar to the prosthetic valves described herein. The prosthetic valve 1700 (shown schematically within the delivery sheath 1726 in FIG. 45) can be disposed in an inverted configuration within the delivery sheath 1726 to reduce the overall outer perimeter of the prosthetic valve 1700. A tether 1736 is coupled to a distal end portion of the prosthetic valve 1700 (see FIGS. 47 and 48). The tether 1736 can be threaded through the leader tube 1724 prior to the leader tube 1724 being disposed within the distal end of the delivery sheath 1726. For example, as previously described, the tether 1736 can include a valve leader member (not shown). The valve leader member can have a tapered distal end to aid in the insertion and maneuvering of the valve leader member through the leader tube 1724. The valve leader member can be attached at a proximal end portion of the tether 1736, which is attached to the valve 1700. The tether 1736 can be formed, for example, as a braided rope or cord. The tether 1736 can be threaded through the leader tube 1724 with the valve leader member extended out the apex of the proximal end of the leader tube 1724 outside the apex of the heart. Thus, the tether 1736 extends between the apex Ap and the femoral puncture site where it is coupled to the valve 1700.

The delivery sheath 1726 can then be inserted through the femoral puncture site and moved through the femoral vein, through the inferior vena cava, into the right atrium, and then through the septum Sp until a distal end portion of the delivery sheath 1726 (with the valve 1700) is disposed within the left atrium LA, as shown in FIG. 46. The dilator balloon member 1711 can provide a smooth lead-in to assist in maneuvering the distal end of the delivery sheath 1726 through the femoral vein and within the heart. Although the delivery sheath 1726 is used to deliver both the snare device 1728 and the valve 1700, in other embodiments, a different delivery sheath can be used to deliver the snare device 1728 than is used to deliver the valve 1700.

With the distal end of the delivery sheath 1726 within the left atrium LA, the leader tube 1724 can be removed through the apex Ap, leaving the tether 1736 extended between the valve 1700 and outside the apex Ap of the heart (see FIG. 47). For example, the balloon dilator member 1711 can be moved back to a collapsed configuration for removal through the procedural catheter 1735. The procedural catheter 1735 can then also be removed. The pusher 1738 can be used to push or move the valve 1700 out the distal end of the delivery sheath 1726 and within the left atrium LA of the heart as shown in FIG. 47. As the valve exits the distal end of the delivery sheath 1726 the valve 1700 can revert and return to its original undeformed shape as described above, for example, for valve 200. For example, the valve 1700 can be formed with a shape-memory material and can have a biased undeformed shape and can be manipulated and/or deformed (e.g., compressed and/or expanded) and, when released, return to its original undeformed shape. The valve can be, for example, a valve constructed the same as or similar to, and function in the same or similar manner as, the prosthetic heart valve 200, described above.

As shown in FIG. 47, the tether 1736 extends from the valve 1700 through the apical puncture and outside the patient's body. As the delivery sheath 1726 is advanced, the tether 1736 can optionally be pulled at the apex end to help move the delivery sheath 1726, with the valve 1700 disposed therein, through the femoral vein, through the septal puncture and into the left atrium LA. The valve 1700 can then be fully deployed within the left atrium LA, as shown in FIG. 48, by using the pusher 1738 described above and/or by pulling the apex end portion of the tether 1736 until the valve 1700 is pulled out of the lumen of the delivery sheath 1726 and disposed within the left atrium LA.

In some embodiments, the pusher 1738 can also be used to aid in positioning the valve 1700 in a desired radial orientation within the left atrium LA. For example, the pusher device 1738 can define an internal lumen (not shown) that can be placed over an inner frame portion of the valve 1700 to hold the inner frame portion in a small diameter, which can help enable the valve 1700 to be positioned in a desired radial orientation and be seated within the annulus of the mitral valve. Further examples of such a valve assist device are described below with reference to FIGS. 49-51.

As shown in FIG. 48, as the valve 1700 is deployed within the left atrium LA, the valve 1700 is allowed to assume its biased expanded or deployed configuration. The delivery sheath 1726 can then be removed from the patient and the valve 1700 can be positioned and tensioned using the tether 1736 to obtain the desired or optimal location in the native mitral annulus and minimize perivalvular leaks. An epicardial pad device 1739 (as described above) can be used to secure the tether 1736 and valve 1700 in position within the mitral annulus. In some embodiments, rather than securing the prosthetic mitral valve with a tether and epicardial pad, the prosthetic mitral valve can be secured with clips or other coupling methods to a portion(s) of the mitral valve apparatus and/or the ventricular wall of the heart.

Although not shown for all embodiments, any of the embodiments of a delivery device or system can include a handle or handle assembly to which the various delivery sheaths and components can be operatively coupled and which a user (e.g., physician) can grasp and use to manipulate the delivery device or system. For example, the handle assembly can include controls to move the various delivery sheaths and other components.

In addition, the systems and methods described herein can also be adapted for use with a prosthetic tricuspid valve. For example, in such a case, a procedural catheter can be inserted into the right ventricle of the heart, and the delivery sheath delivered to the right atrium of the heart either directly (transatrial), or via the jugular or femoral vein. In such a case, the delivery devices to deliver an epicardial pad can be disposed outside the heart below the right ventricle and/or be inserted within the right ventricle depending on the particular embodiment of the epicardial pad being delivered.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

What is claimed is:

1. An apparatus, comprising:
an epicardial pad configured to engage an outside surface of a heart to secure a prosthetic heart valve in position within the heart, the prosthetic heart valve having a tether extending therefrom and outside the heart when the prosthetic heart valve is disposed within the heart, the epicardial pad defining a lumen configured to receive the tether therethrough,
the epicardial pad being movable between a first configuration in which the epicardial pad has a first outer perimeter and is configured to be disposed within a lumen of a delivery sheath and a second configuration in which the epicardial pad has a second outer perimeter greater than the first outer perimeter,
the epicardial pad configured to be disposed against the outside surface of the heart when in the second configuration to secure the prosthetic valve and tether in a desired position within the heart,
wherein the epicardial pad is a balloon.

2. The apparatus of claim 1, wherein the balloon is configured to be inflated by an inflation medium to move the epicardial pad to the second configuration.

3. The apparatus of claim 1, wherein the balloon is configured to be inflated by an inflation medium to move the epicardial pad to a third configuration in which the epicardial pad is expanded, the epicardial pad configured to be moved from the third configuration to the second configuration in which the epicardial pad is collapsed inwardly to form a cup shape.

4. The apparatus of claim 1, wherein the balloon includes an inflation lumen through which an inflation medium can be communicated to and from the balloon.

5. The apparatus of claim 4, wherein the inflation lumen is defined by the balloon.

6. The apparatus of claim 4, wherein the inflation lumen is defined by an inflation line separate from the balloon and in fluid communication with an interior of the balloon.

\* \* \* \* \*